United States Patent
Liang et al.

(10) Patent No.: US 10,428,327 B2
(45) Date of Patent: Oct. 1, 2019

(54) COMPOSITIONS AND METHODS FOR ENHANCING HOMOLOGOUS RECOMBINATION

(71) Applicant: LIFE TECHNOLOGIES CORPORATION, Carlsbad, CA (US)

(72) Inventors: Xiquan Liang, Escondido, CA (US); Robert Potter, San Marcos, CA (US); Namritha Ravinder, San Diego, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 15/605,586

(22) Filed: May 25, 2017

(65) Prior Publication Data
US 2018/0023075 A1    Jan. 25, 2018

Related U.S. Application Data

(60) Provisional application No. 62/342,504, filed on May 27, 2016.

(51) Int. Cl.
*C12N 15/10* (2006.01)
*C12N 15/113* (2010.01)
*C12N 15/90* (2006.01)

(52) U.S. Cl.
CPC ....... *C12N 15/1082* (2013.01); *C12N 15/102* (2013.01); *C12N 15/1024* (2013.01); *C12N 15/1034* (2013.01); *C12N 15/113* (2013.01); *C12N 15/907* (2013.01); *A01K 2217/07* (2013.01); *C12N 2310/152* (2013.01); *C12N 2310/153* (2013.01); *C12N 2310/20* (2017.05); *C12N 2310/533* (2013.01); *C12Q 2600/156* (2013.01)

(58) Field of Classification Search
CPC .................. C12N 15/902–907; C12N 2310/20
See application file for complete search history.

(56) References Cited

U.S. PATENT DOCUMENTS 9,005,973 B2 * 4/2015 Cost .......................... C12N 9/22
435/440

FOREIGN PATENT DOCUMENTS

| WO | WO-2003/012036 | 2/2003 |
|---|---|---|
| WO | WO-2009/131632 | 10/2009 |
| WO | WO-2011/100058 | 8/2011 |
| WO | WO-2014/102688 | 7/2014 |
| WO | WO-2016/073990 | 5/2016 |
| WO | WO-2017/096041 | 6/2017 |

OTHER PUBLICATIONS

Ran et al. Double nicking by RNA-guided CRISPR Cas9 for enhanced genome editing specificity. Cell, vol. 154, pp. 1380-1389, Sep. 12, 2013, including pp. S1-S5 of Supplemental Information. (Year: 2013).*
Renaud et al. Improved genome editing efficiency and flexibility using modified oligonucleotides with TALEN and CRISPR-Cas9 nucleases. Cell Reports, vol. 14, pp. 2263-2272, Mar. 8, 2016, including pp. 1/21-21/21 of Supplemental Information. (Year: 2016).*
Brown, D. et al., "Effect of Phosphorothioate Modification of Oligodeoxynucleotides on Specific Protein Binding", *The Journal of Biological Chemistry*, vol. 269, No. 43, Oct. 28, 1994, 26801-26805.
Igoucheva, O. et al., "Targeted gene correction by small single-stranded oligonucleotides in mammalian cells", *Gene Therapy*, vol. 8, No. 5, Mar. 2001, 391-399.
Kan, Y. et al., "The Mechanism of Gene Targeting in Human Somatic Cells", *PLOS Genetics*, vol. 10, No. 4, Apr. 2014, e1004251.
Liang, X. et al., "Enhanced CRISPR/Cas9-mediated precise genome editing by improved design and delivery of gRNA, Cas9 nuclease, and donor DNA", *Journal of Biotechnology*, vol. 241, Nov. 11, 2016, 136-146.
Lin, S. et al., "Enhanced homology-directed human genome engineering by controlled timing of CRISPR/Cas9 delivery", *eLIFE*, vol. 3, Dec. 15, 2014, e04766.
PCT/US2017/034520, "International Search Report dated", Nov. 6, 2017, 11 Pages.
Richardson, C et al., "Enhancing homology-directed genome editing by catalytically active and inactive CRISPR-Cas9 using asymmetric donor DNA", *Nature Biotechnology*, vol. 34, No. 3, Mar. 2016, 339-344
Richardson, C et al., "Supplemental Material to "Enhancing homology-directed genome editing by catalytically active and inactive CRISPR-Cas9 using asymmetric donor DNA"", *Nature Biotechnology*, vol. 34, No. 3, Mar. 2016, 1-108.
Rong, Z. et al., "Homologous recombination in human embryonic stem cells using CRISPR/CAS9 nickase and a long DNA donor template", *Protein & Cell*, vol. 5, No. 4, Mar. 14, 2014, 258-260.
Song, F. et al., "Optimizing the DNA Donor TEmplate for Homology-Directed Repair of Double-Strand Breaks", *Molecular Therapy—Nucleic Acids*, vol. 7, Jun. 2017, 53-60.

* cited by examiner

*Primary Examiner* — Jennifer Dunston
(74) *Attorney, Agent, or Firm* — Life Technologies Corporation; Stephen G. Whiteside

(57) ABSTRACT

The present disclosure generally relates to compositions and methods for improving the efficiency of homologous recombination. In particular, the disclosure relates to reagents and the use of such reagents.

12 Claims, 16 Drawing Sheets

Specification includes a Sequence Listing.

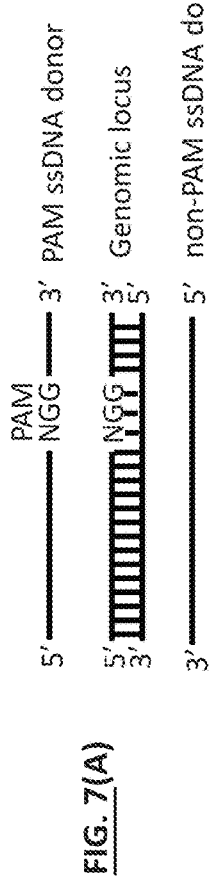
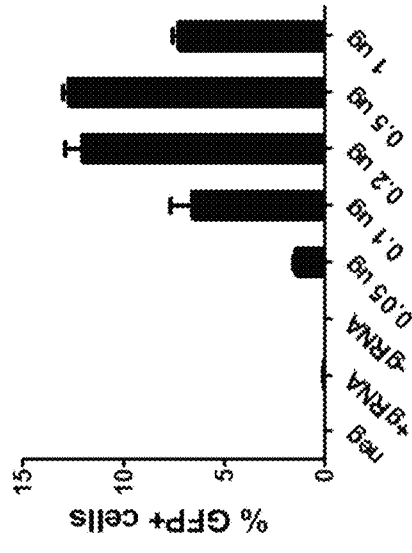
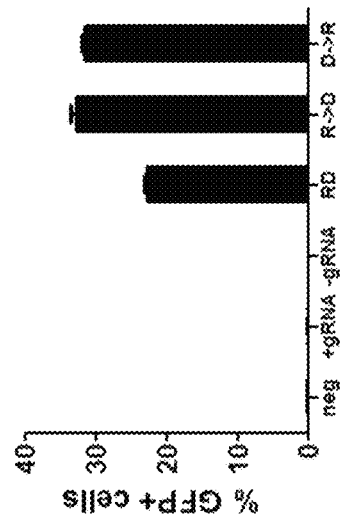
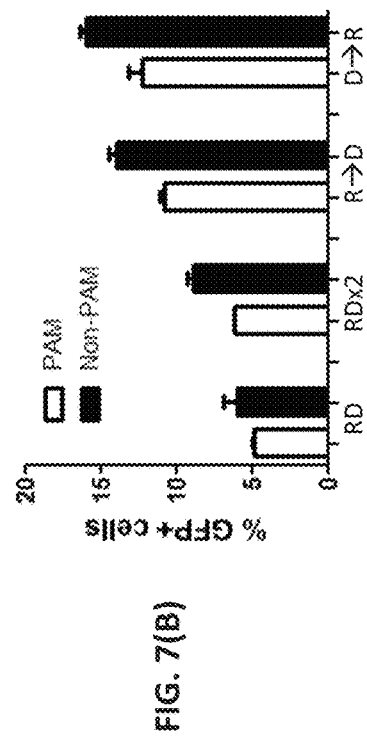
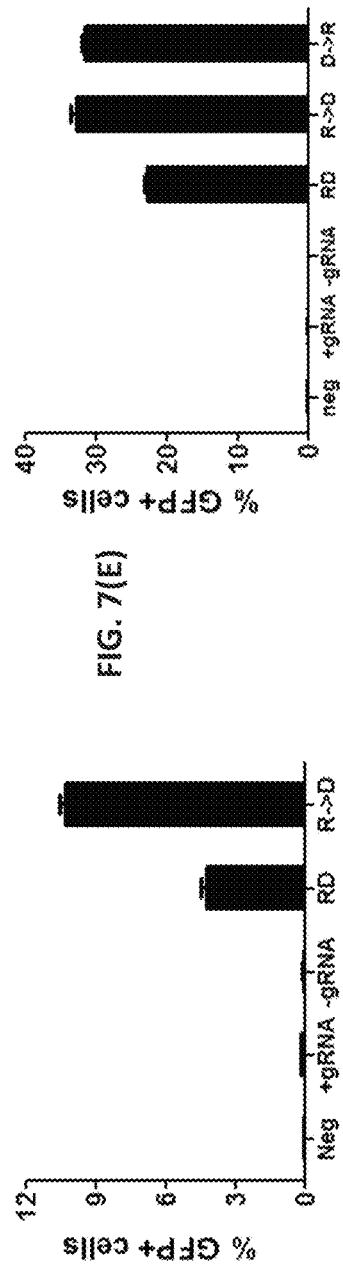
FIG. 7(A)
FIG. 7(B)
FIG. 7(C)
FIG. 7(D)
FIG. 7(E)

FIG. 8(A)
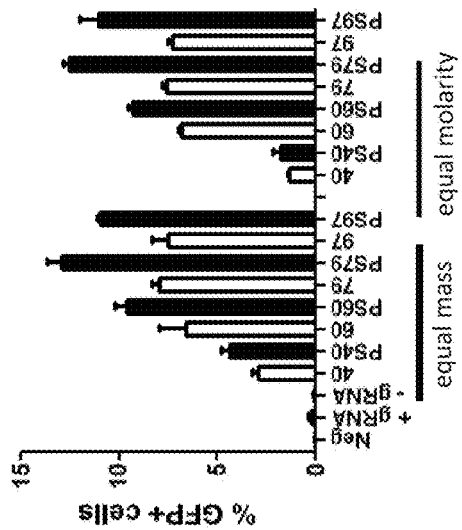
FIG. 8(B)
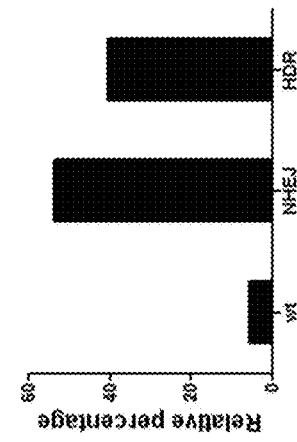
FIG. 8(C)
FIG. 8(D)

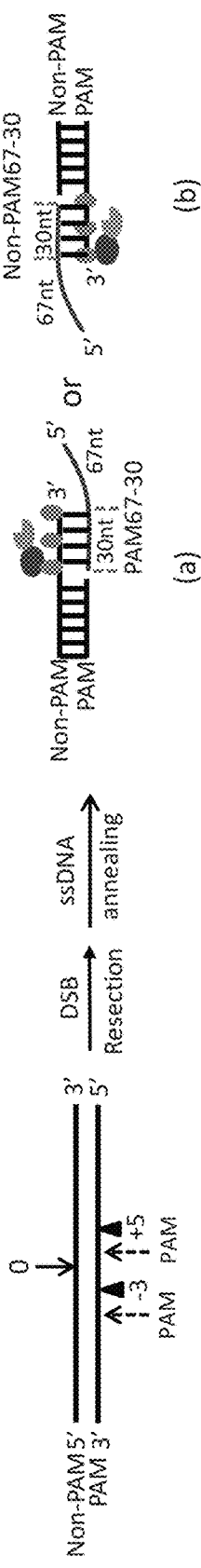
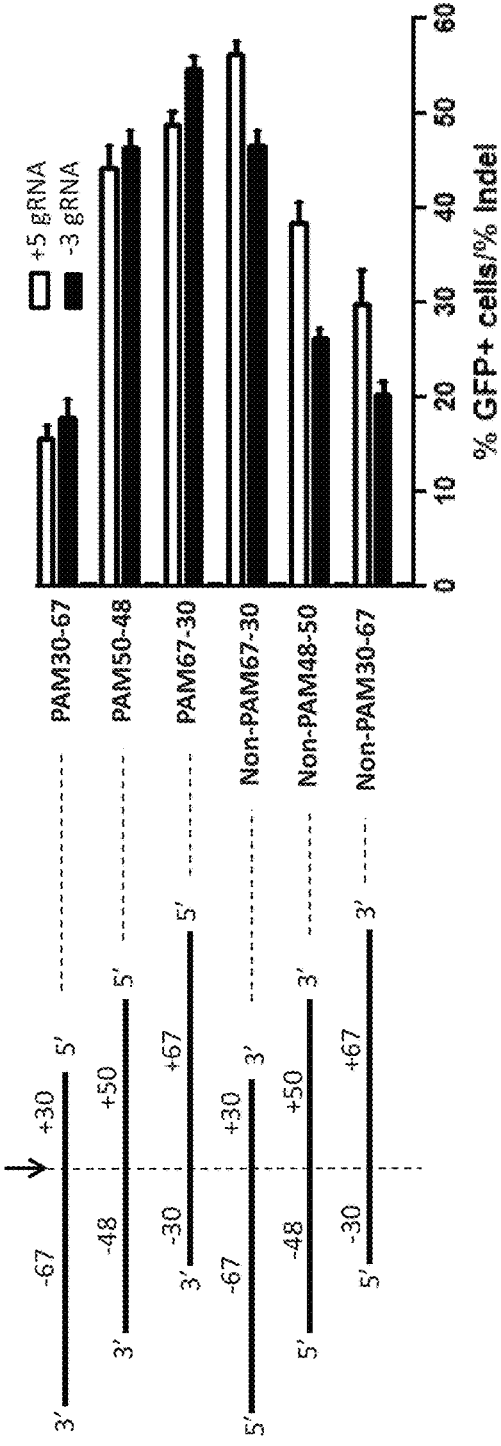
FIG. 10(A)
FIG. 10(B)
FIG. 10(C)

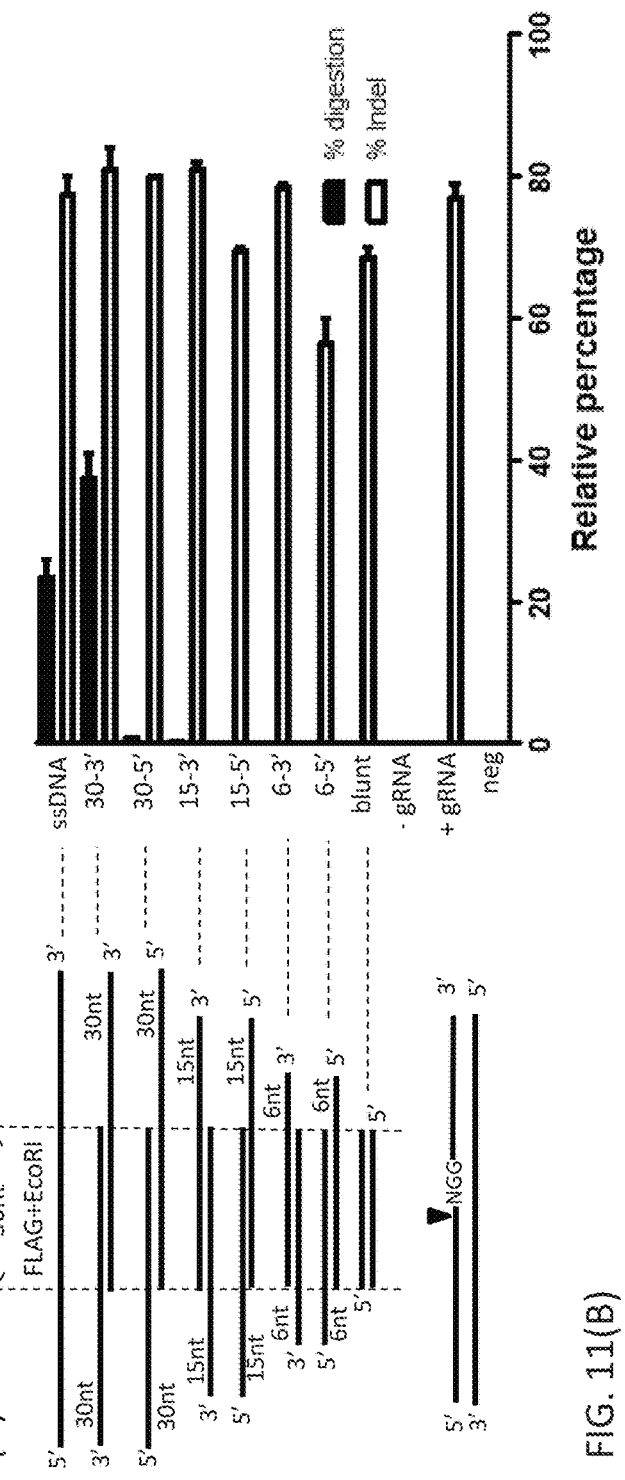
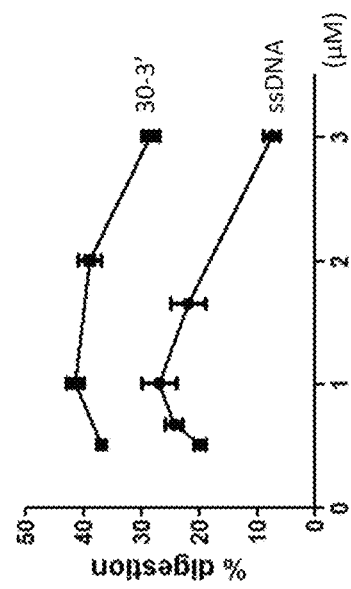
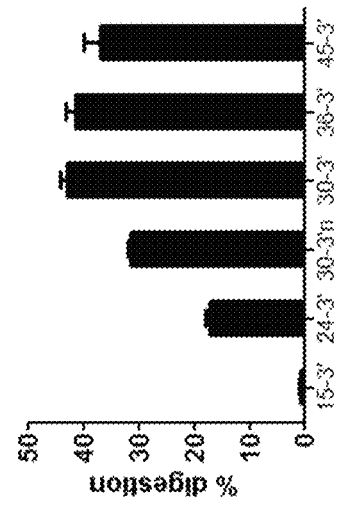
FIG. 11(A)
FIG. 11(B)
FIG. 11(C)

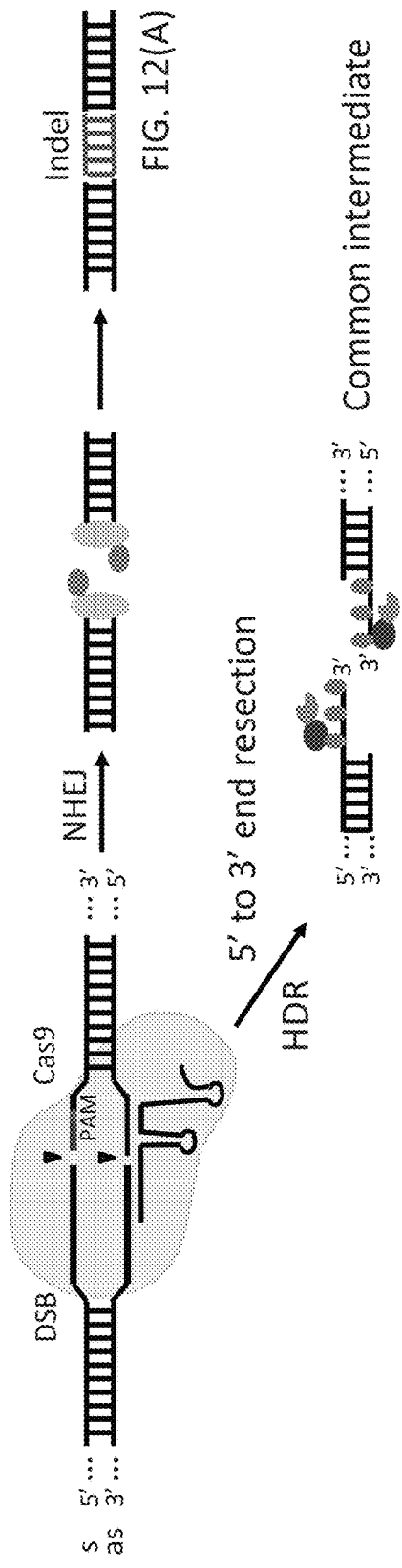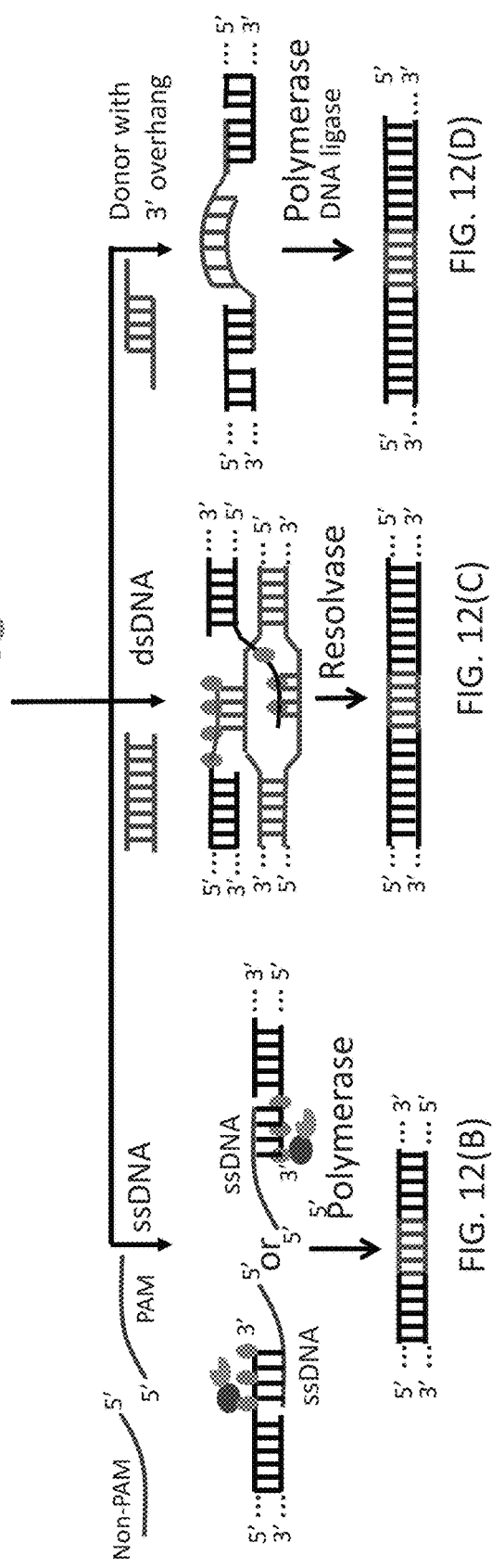

FIG. 13(A)

| Residue# | 61 | 62 | 63 | 64 | 65 | 66 | 67 | |
|---|---|---|---|---|---|---|---|---|
| Wild type | Val<br>...GTG | Thr<br>ACC | Thr<br>ACC | Phe<br>TTC | Thr<br>ACC | Tyr<br>TAC | Gly<br>GGC... | (SEQ ID No: 26)<br>(SEQ ID No: 27) |
| Mutant | Val<br>...GTG | Thr<br>ACC | Thr<br>ACC | | Thr<br>ACC | Tyr<br>TAC | Gly<br>GGC... | (SEQ ID No: 28)<br>(SEQ ID No: 29) |

FIG. 13(B)

| Residue# | 64 | 65 | 66 | 67 | |
|---|---|---|---|---|---|
| eBFP | Leu<br>...CTG | Thr<br>ACC | His<br>CAC | Gly<br>GGC... | (SEQ ID No: 30)<br>(SEQ ID No: 31) |
| GFP | Leu<br>...CTG | Thr<br>ACC | Tyr<br>TAC | Gly<br>GGC... | (SEQ ID No: 32)<br>(SEQ ID No: 33) |

SEQUENCE LISTING

```
<160> NUMBER OF SEQ ID NOS: 127

<210> SEQ ID NO 1
<211> LENGTH: 104
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 1
gcauuucggu augcauauga augaguuuua gagcuagaaa uagcaaguua aaauaaggcu      60
aguccguuau caacuugaaa aaguggcacc gagucggugc uuuu                     104

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgtaaagcca tacgtatact acc                                             23

<210> SEQ ID NO 3
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 3
gcatttcggt atgcatatga ngg                                             23

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcgtgaccac cctgacccac ggcgtgcagt gcttcagccg ctaccccg                  48

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tcgtgaccac cctgacctac ggcgtgcagt gcttcagccg ctaccccg                  48

<210> SEQ ID NO 6
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tcgtgaccac cctgacctac ggcgtgcagt gcttcagcgg cgtgcagtgc ttcagccgct     60
accccg                                                                66

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcgtgactac ggcgtgcagt gcttcagccg ctaccccg                             38

<210> SEQ ID NO 8
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tcgtgaccac cctgaccacg gcgtgcagtg cttcagccgc taccccg                   47
```

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tcgaggccac ggcgtgcagt gcttcagccg ctaccccg                          38

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tctacggcgt gcagtgcttc agccgctacc ccg                               33

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tcgtggcgtg cagtgcttca gccgctaccc cg                                32

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tcgtgcgtgc agtgcttcag ccgctacccc g                                 31

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tcgtgaccaa gccgctaccc cg                                           22

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tcgtgaccac cccg                                                    14

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gaccaccctg acccacggcg                                                20

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gaccaccctg accgactaca aagacgatga cgacaagaat tcttacggcg               50

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gaccaccctg cccgactaca aagacgatga cgacaagaat tcttacggcg               50

<210> SEQ ID NO 18
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gaccaccctg ccgactacaa agacgatgac gacaagaatt cttacggcg                49

<210> SEQ ID NO 19
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gaccaccctg gcctgcaccc tcgtgacacc ctgaccgact acaaagacga tgacgacaag    60
tattcttacg gcg                                                       73

<210> SEQ ID NO 20
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gaccaccctg accgactaca aagacgacaa gaattcttac ggcg                     44

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gaccgactac aaagacgaca agaattctta cggcg                           35

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gaccgacgat gacgacaaaa ttcttacggc g                               31

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gaccacggcg                                                       10

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gaccccacgg cg                                                    12

<210> SEQ ID NO 25
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25 cacctt                                                            6

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Val Thr Thr Phe Thr Tyr Gly
1               5

```
<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(21)

<400> SEQUENCE: 27 gtg acc acc ttc acc tac ggc                                          21
Val Thr Thr Phe Thr Tyr Gly
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Thr Thr Tyr Gly
1               5

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(15)

<400> SEQUENCE: 29 gtg acc acc tac ggc                                                  15
Val Thr Thr Tyr Gly
1               5

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Thr His Gly
1

<210> SEQ ID NO 31
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(12)

<400> SEQUENCE: 31
```

```
ctg acc cac ggc                                                          12
Leu Thr His Gly
1
```

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Leu Thr Tyr Gly
1
```

<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(12)

<400> SEQUENCE: 33

```
ctg acc tac ggc                                                          12
Leu Thr Tyr Gly
1
```

<210> SEQ ID NO 34
<211> LENGTH: 887
<212> TYPE: PRT
<213> ORGANISM: Natronobacterium gregoryi

<400> SEQUENCE: 34

```
Met Thr Val Ile Asp Leu Asp Ser Thr Thr Ala Asp Glu Leu Thr
1               5                   10                  15

Ser Gly His Thr Tyr Asp Ile Ser Val Thr Leu Thr Gly Val Tyr Asp
                20                  25                  30

Asn Thr Asp Glu Gln His Pro Arg Met Ser Leu Ala Phe Glu Gln Asp
            35                  40                  45

Asn Gly Glu Arg Arg Tyr Ile Thr Leu Trp Lys Asn Thr Thr Pro Lys
        50                  55                  60

Asp Val Phe Thr Tyr Asp Tyr Ala Thr Gly Ser Thr Tyr Ile Phe Thr
65                  70                  75                  80

Asn Ile Asp Tyr Glu Val Lys Asp Gly Tyr Glu Asn Leu Thr Ala Thr
                85                  90                  95

Tyr Gln Thr Thr Val Glu Asn Ala Thr Ala Gln Glu Val Gly Thr Thr
            100                 105                 110

Asp Glu Asp Glu Thr Phe Ala Gly Gly Glu Pro Leu Asp His His Leu
        115                 120                 125

Asp Asp Ala Leu Asn Glu Thr Pro Asp Asp Ala Glu Thr Glu Ser Asp
    130                 135                 140

Ser Gly His Val Met Thr Ser Phe Ala Ser Arg Asp Gln Leu Pro Glu
145                 150                 155                 160

Trp Thr Leu His Thr Tyr Thr Leu Thr Ala Thr Asp Gly Ala Lys Thr
                165                 170                 175

Asp Thr Glu Tyr Ala Arg Arg Thr Leu Ala Tyr Thr Val Arg Gln Glu
            180                 185                 190
```

```
Leu Tyr Thr Asp His Asp Ala Ala Pro Val Ala Thr Asp Gly Leu Met
    195                 200                 205

Leu Leu Thr Pro Glu Pro Leu Gly Glu Thr Pro Leu Asp Leu Asp Cys
    210                 215                 220

Gly Val Arg Val Glu Ala Asp Glu Thr Arg Thr Leu Asp Tyr Thr Thr
225                 230                 235                 240

Ala Lys Asp Arg Leu Leu Ala Arg Glu Leu Val Glu Glu Gly Leu Lys
                245                 250                 255

Arg Ser Leu Trp Asp Asp Tyr Leu Val Arg Gly Ile Asp Glu Val Leu
                260                 265                 270

Ser Lys Glu Pro Val Leu Thr Cys Asp Glu Phe Asp Leu His Glu Arg
            275                 280                 285

Tyr Asp Leu Ser Val Glu Val Gly His Ser Gly Arg Ala Tyr Leu His
        290                 295                 300

Ile Asn Phe Arg His Arg Phe Val Pro Lys Leu Thr Leu Ala Asp Ile
305                 310                 315                 320

Asp Asp Asp Asn Ile Tyr Pro Gly Leu Arg Val Lys Thr Thr Tyr Arg
                325                 330                 335

Pro Arg Arg Gly His Ile Val Trp Gly Leu Arg Asp Glu Cys Ala Thr
                340                 345                 350

Asp Ser Leu Asn Thr Leu Gly Asn Gln Ser Val Ala Tyr His Arg
            355                 360                 365

Asn Asn Gln Thr Pro Ile Asn Thr Asp Leu Leu Asp Ala Ile Glu Ala
        370                 375                 380

Ala Asp Arg Arg Val Val Glu Thr Arg Arg Gln Gly His Gly Asp Asp
385                 390                 395                 400

Ala Val Ser Phe Pro Gln Glu Leu Leu Ala Val Glu Pro Asn Thr His
                405                 410                 415

Gln Ile Lys Gln Phe Ala Ser Asp Gly Phe His Gln Gln Ala Arg Ser
            420                 425                 430

Lys Thr Arg Leu Ser Ala Ser Arg Cys Ser Glu Lys Ala Gln Ala Phe
        435                 440                 445

Ala Glu Arg Leu Asp Pro Val Arg Leu Asn Gly Ser Thr Val Glu Phe
    450                 455                 460

Ser Ser Glu Phe Phe Thr Gly Asn Asn Glu Gln Gln Leu Arg Leu Leu
465                 470                 475                 480

Tyr Glu Asn Gly Glu Ser Val Leu Thr Phe Arg Asp Gly Ala Arg Gly
                485                 490                 495

Ala His Pro Asp Glu Thr Phe Ser Lys Gly Ile Val Asn Pro Pro Glu
            500                 505                 510

Ser Phe Glu Val Ala Val Val Leu Pro Glu Gln Gln Ala Asp Thr Cys
        515                 520                 525

Lys Ala Gln Trp Asp Thr Met Ala Asp Leu Leu Asn Gln Ala Gly Ala
    530                 535                 540

Pro Pro Thr Arg Ser Glu Thr Val Gln Tyr Asp Ala Phe Ser Ser Pro
545                 550                 555                 560

Glu Ser Ile Ser Leu Asn Val Ala Gly Ala Ile Asp Pro Ser Glu Val
                565                 570                 575

Asp Ala Ala Phe Val Val Leu Pro Asp Gln Glu Gly Phe Ala Asp
            580                 585                 590

Leu Ala Ser Pro Thr Glu Thr Tyr Asp Glu Leu Lys Lys Ala Leu Ala
        595                 600                 605
```

```
Asn Met Gly Ile Tyr Ser Gln Met Ala Tyr Phe Asp Arg Phe Arg Asp
    610                 615                 620

Ala Lys Ile Phe Tyr Thr Arg Asn Val Ala Leu Gly Leu Leu Ala Ala
625                 630                 635                 640

Ala Gly Gly Val Ala Phe Thr Thr Glu His Ala Met Pro Gly Asp Ala
                645                 650                 655

Asp Met Phe Ile Gly Ile Asp Val Ser Arg Ser Tyr Pro Glu Asp Gly
            660                 665                 670

Ala Ser Gly Gln Ile Asn Ile Ala Ala Thr Ala Thr Ala Val Tyr Lys
        675                 680                 685

Asp Gly Thr Ile Leu Gly His Ser Ser Thr Arg Pro Gln Leu Gly Glu
690                 695                 700

Lys Leu Gln Ser Thr Asp Val Arg Asp Ile Met Lys Asn Ala Ile Leu
705                 710                 715                 720

Gly Tyr Gln Gln Val Thr Gly Glu Ser Pro Thr His Ile Val Ile His
                725                 730                 735

Arg Asp Gly Phe Met Asn Glu Asp Leu Asp Pro Ala Thr Glu Phe Leu
            740                 745                 750

Asn Glu Gln Gly Val Glu Tyr Asp Ile Val Glu Ile Arg Lys Gln Pro
        755                 760                 765

Gln Thr Arg Leu Leu Ala Val Ser Asp Val Gly Tyr Asp Thr Pro Val
770                 775                 780

Lys Ser Ile Ala Ala Ile Asn Gln Asn Glu Pro Arg Ala Thr Val Ala
785                 790                 795                 800

Thr Phe Gly Ala Pro Glu Tyr Leu Ala Thr Arg Asp Gly Gly Gly Leu
                805                 810                 815

Pro Arg Pro Ile Gln Ile Glu Arg Val Ala Gly Glu Thr Asp Ile Glu
            820                 825                 830

Thr Leu Thr Arg Gln Val Tyr Leu Leu Ser Gln Ser His Ile Gln Val
        835                 840                 845

His Asn Ser Thr Ala Arg Leu Pro Ile Thr Thr Ala Tyr Ala Asp Gln
850                 855                 860

Ala Ser Thr His Ala Thr Lys Gly Tyr Leu Val Gln Thr Gly Ala Phe
865                 870                 875                 880

Glu Ser Asn Val Gly Phe Leu
                885

<210> SEQ ID NO 35
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
catctgcacc accggcaagc tgcccgtgcc ctggcccacc ctcgtgacca ccttcaccta      60
cggcgtgcag tgcttcgccc gctaccccga ccacatg                              97

<210> SEQ ID NO 36
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
```

```
catgtggtcg gggtagcggg cgaagcactg cacgccgtag gtgaaggtgg tcacgagggt    60
gggccagggc acgggcagct tgccggtggt gcagatg                             97

<210> SEQ ID NO 37
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
catgtggtcg gggtagcggg cgaagcactg cacgccgtag gtgaaggtgg tcacgagggt    60
gggccagggc acgggcagct tgccggtggt gcagatg                             97

<210> SEQ ID NO 38
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
catgtggtcg gggtagcggg cgaagcactg cacgccgtag gtgaaggtgg tcacgagggt    60
gggccagggc acgggcagc                                                 79

<210> SEQ ID NO 39
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
catgtggtcg gggtagcggg cgaagcactg cacgccgtag gtgaaggtgg tcacgagggt    60
gggccagggc acgggcagc                                                 79

<210> SEQ ID NO 40
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cggggtagcg gcgaagcac tgcacgccgt aggtgaaggt ggtcacgagg gtgggccagg     60

<210> SEQ ID NO 41
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cggggtagcg gcgaagcac tgcacgccgt aggtgaaggt ggtcacgagg gtgggccagg     60

<210> SEQ ID NO 42
<211> LENGTH: 40
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ggcgaagcac tgcacgccgt aggtgaaggt ggtcacgagg                            40

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ggcgaagcac tgcacgccgt aggtgaaggt ggtcacgagg                            40

<210> SEQ ID NO 44
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
accggcaagc tgcccgtgcc ctggcccacc ctcgtgacca ccctgaccta cggcgtgcag      60
tgcttcagcc gctaccccga ccacatgaag cagcacgact                           100

<210> SEQ ID NO 45
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
accggcaagc tgcccgtgcc ctggcccacc ctctgaccac cctgacctac ggcgtgcagt      60
gcttcagccg ctaccccgac cacatgaagc agcacgact                            99

<210> SEQ ID NO 46
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gcaagctgcc cgtgccctgg cccaccctcg tgaccaccct gacctacggc gtgcagtgct      60
tcagccgcta ccccgaccac atgaagcagc                                      90

<210> SEQ ID NO 47
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gcaagctgcc cgtgccctgg cccaccctcg tgaccaccct gacctacggc gtgcagtgct    60
tcagccgcta ccccgaccac atgaagcagc    90

<210> SEQ ID NO 48
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gctgcccgtg ccctggccca ccctcgtgac caccctgacc tacggcgtgc agtgcttcag    60
ccgctacccc gaccacatga    80

<210> SEQ ID NO 49
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gctgcccgtg ccctggccca ccctcgtgac caccctgacc tacggcgtgc agtgcttcag    60
ccgctacccc gaccacatga    80

<210> SEQ ID NO 50
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
cccgtgccct ggcccaccct cgtgaccacc ctgacctacg gcgtgcagtg cttcagccgc    60
taccccgacc    70

<210> SEQ ID NO 51
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cccgtgccct ggcccaccct cgtgaccacc ctgacctacg gcgtgcagtg cttcagccgc    60
taccccgacc    70

<210> SEQ ID NO 52
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gccctggccc accctcgtga ccaccctgac ctacggcgtg cagtgcttca gccgctaccc    60

<210> SEQ ID NO 53

<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gccctggccc accctcgtga ccaccctgac ctacggcgtg cagtgcttca gccgctaccc    60

<210> SEQ ID NO 54
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cccaccctcg tgaccaccct gacctacggc gtgcagtgct tcagccgcta                50

<210> SEQ ID NO 55
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cccaccctcg tgaccaccct gacctacggc gtgcagtgct tcagccgcta                50

<210> SEQ ID NO 56
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gcgtatcaat ggatacttac attgactaat ccaaactagt gctcattgac cggaaactgt    60
tctggaccaa tctctttctc                                                 80

<210> SEQ ID NO 57
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gcaatccagt gaatccttga ggtgtaacgt ggagccagta aggcggctac atatctttag    60
tggtgcccat ggaccagaaa aag                                             83

<210> SEQ ID NO 58
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ctgcacgggg ctgctggcgc tcacatttcc tattcctgga ttgatactag agccgctgcc    60

```
tcctcgtaga agctccgaca g                                              81

<210> SEQ ID NO 59
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ctgaccttgc cttcatgtga ttcagcccca gtccattacc ctgtgtagga ctgagaaatg    60
caagactctg gctagagttc cttcttccat ctcccttc                            98

<210> SEQ ID NO 60
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ctgaccttgc cttcatgtga ttcagcccca gtccattaca ctgtgtagga ctgagaaatg    60
caagactctg gctagagttc cttcttccat ctcccttc                            98

<210> SEQ ID NO 61
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ctgaagttca tctgcaccac cggcaagctg cccgtgccct ggcccaccct cgtgaccacc    60
ttcacctacg gcgtgcagtg cttcgcccgc taccccg                             97

<210> SEQ ID NO 62
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cggggtagcg ggcgaagcac tgcacgccgt aggtgaaggt ggtcacgagg gtgggccagg    60
gcacgggcag cttgccggtg gtgcagatga acttcag                             97

<210> SEQ ID NO 63
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ccgtgccctg gcccaccctc gtgaccacct tcacctacgg cgtgcagtgc ttcgcccgct    60
accccgacca catgaagcag cacgacttct tcaagtc                             97
```

```
<210> SEQ ID NO 64
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gacttgaaga agtcgtgctg cttcatgtgg tcggggtagc gggcgaagca ctgcacgccg    60
taggtgaagg tggtcacgag ggtgggccag ggcacgg                             97

<210> SEQ ID NO 65
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ccaccggcaa gctgcccgtg ccctggccca ccctcgtgac caccttcacc tacggcgtgc    60
agtgcttcgc ccgctacccc g                                              81

<210> SEQ ID NO 66
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cggggtagcg ggcgaagcac tgcacgccgt aggtgaaggt ggtcacgagg gtgggccagg    60
gcacgggcag cttgccggtg g                                              81

<210> SEQ ID NO 67
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ccgtgccctg gcccaccctc gtgaccacct tcacctacgg cgtgcagtgc ttcgcccgct    60
accccgacca catgaagcag c                                              81

<210> SEQ ID NO 68
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gctgcttcat gtggtcgggg tagcgggcga agcactgcac gccgtaggtg aaggtggtca    60
cgagggtggg ccagggcacg g                                              81

<210> SEQ ID NO 69
<211> LENGTH: 98
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 69
ccaccggcaa gctgcccgtg ccctggccca ccctcgtgac caccttcacc tacggcgtgc    60
agtgcttcgc ccgctacccc gaccacatga agcagcac    98

<210> SEQ ID NO 70
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gtgctgcttc atgtggtcgg ggtagcgggc gaagcactgc acgccgtagg tgaaggtggc    60
acgagggtgg gccagggcac gggcagcttg ccggtgg    97

<210> SEQ ID NO 71
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
caagctgccc gtgccctggc ccaccctcgt gaccaccttc acctacggcg tgcagtgctt    60
cgcccgctac cccgaccaca tg    82

<210> SEQ ID NO 72
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
catgtggtcg gggtagcggg cgaagcactg cacgccgtag gtgaaggtgg tcacgagggt    60
gggccagggc acgggcagct tg    82

<210> SEQ ID NO 73

<400> SEQUENCE: 73

000

<210> SEQ ID NO 74
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gtgccctggc ccaccctcgt gaccaccctg accgactaca agacgatga cgacaagaat    60 tcttacggcg tgcagtgctt cagccgctac cccgaccac    99

<210> SEQ ID NO 75

-continued

```
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gactacaaag acgatgacga caagaattct t                                     31

<210> SEQ ID NO 76
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
aagaattctt gtcgtcatcg tctttgtagt c                                     31

<210> SEQ ID NO 77
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ctgaccgact acaaagacga tgacgacaag aattctt                               37

<210> SEQ ID NO 78
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cgccgtaaga attcttgtcg tcatcgtctt tgtagtc                               37

<210> SEQ ID NO 79
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gactacaaag acgatgacga caagaattct tacggcg                               37

<210> SEQ ID NO 80
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
aagaattctt gtcgtcatcg tctttgtagt cggtcag                               37

<210> SEQ ID NO 81
<211> LENGTH: 46
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gtgaccaccc tgaccgacta caaagacgat gacgacaaga attctt            46

<210> SEQ ID NO 82
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gcactgcacg ccgtaagaat tcttgtcgtc atcgtctttg tagtc              45

<210> SEQ ID NO 83
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gactacaaag acgatgacga caagaattct tacggcgtgc agtgc              45

<210> SEQ ID NO 84
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
aagaattctt gtcgtcatcg tctttgtagt cggtcagggt ggtcac            46

<210> SEQ ID NO 85
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gtgccctggc ccaccctcgt gaccaccctg accgactaca agacgatga cgacaagaat    60 tctt                                                                64

<210> SEQ ID NO 86
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gtggtcgggg tagcggctga agcactgcac gccgtaagaa ttcttgtcgt catcgtcttt    60
gtagtc                                                               66
```

<210> SEQ ID NO 87
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gactacaaag acgatgacga caagaattct tacggcgtgc agtgcttcag ccgctacccc    60
gaccac                                                               66

<210> SEQ ID NO 88
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
aagaattctt gtcgtcatcg tctttgtagt cggtcagggt ggtcacgagg gtgggccagg    60
gcac                                                                 64

<210> SEQ ID NO 89
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gactacaaag acgatgacga caagaattct tacggcgtgc agtgcttcag ccgctacccc    60

<210> SEQ ID NO 90
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
aagaattctt gtcgtcatcg tctttgtagt cggtcagggt ggtcacgagg gtgggcca      58

<210> SEQ ID NO 91
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gactacaaag acgatgacga caagaattct tacggcgtgc agtgcttcag ccgctacccc    60
gaccac                                                               66

<210> SEQ ID NO 92
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
aagaattctt gtcgtcatcg tctttgtagt cggtcagggt ggtcacgagg gtgggccagg    60
gcac                                                                 64

<210> SEQ ID NO 93
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
aagaattctt gtcgtcatcg tctttgtagt cggtcagggt ggtcacgagg gtgggccagg    60
gcacggg                                                              67

<210> SEQ ID NO 94
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gactacaaag acgatgacga caagaattct tacggcgtgc agtgcttcag ccgctacccc    60
gaccac                                                               66

<210> SEQ ID NO 95
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gactacaaag acgatgacga caagaattct tacggcgtgc agtgcttcag ccgctacccc    60
gaccacatga agcagcac                                                  78

<210> SEQ ID NO 96
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
aagaattctt gtcgtcatcg tctttgtagt cggtcagggt ggtcacgagg gtgggccagg    60
gcacgggcag cttgccgg                                                  78

<210> SEQ ID NO 97
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gcccgtgccc tggcccaccc tcgtgaccac ctgactacaa agacgatgac gacaagaatt    60
ctacggcgtg cagtgcttcg cccgctaccc cgac           94

<210> SEQ ID NO 98
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gcccgtgccc tggcccaccc tcgtgaccac ctgactacaa agacgatgac gacaagaatt    60
cta                                                                  63

<210> SEQ ID NO 99
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gtcggggtag cgggcgaagc actgcacgcc gtagaattct tgtcgtcatc gtctttgtag    60
tc                                                                   62

<210> SEQ ID NO 100
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
agaattcttg tcgtcatcgt ctttgtagtc aggtggtcac gagggtgggc cagggcacgg    60
gc                                                                   62

<210> SEQ ID NO 101
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gactacaaag acgatgacga caagaattct acggcgtgca gtgcttcgcc cgctaccccg    60
ac                                                                   62

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ctcgtgacca ccctgaccca cgg                                            23

<210> SEQ ID NO 103
<211> LENGTH: 23

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ctgaagttca tctgcaccac cgg                                            23

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gggcacgggc agcttgccgg tgg                                            23

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ccagggcacg ggcagcttgc cgg                                            23

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ggcaagctgc ccgtgccctg g                                              21

<210> SEQ ID NO 107
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
cacgagggtg ggccagggca cgg                                            23

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ggtggtcacg agggtgggcc agg                                            23

<210> SEQ ID NO 109
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 109
gccgtaggtg gtcacgaggg tgg                                             23

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gcacgccgta ggtggtcacg agg                                             23

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
cccaccctcg tgaccaccta cgg                                             23

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gaagcactgc acgccgtagg tgg                                             23

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ggcgaagcac tgcacgccgt agg                                             23

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
cttcatgtgg tcggggtagc ggg                                             23

<210> SEQ ID NO 115
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 115
gtcgtgctgc ttcatgtggt cgg                                              23

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
agaagtcgtg ctgcttcatg tgg                                              23

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gcatttctca gtcctaaaca ggg                                              23

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
agcggctcta gtatcaaccc                                                  20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
aagatatgta gccgccctac                                                  20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
ccggtcaatg agcactattt                                                  20

<210> SEQ ID NO 121
<211> LENGTH: 720
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 121

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccttcaccta cggcgtgcag tgcttcgccc gctacccga ccacatgaag    240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaag gtctatatca ccgccgacaa gcagaagaac   480
ggcatcaagg tgaacttcaa gacccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaagtaa   720
```

<210> SEQ ID NO 122
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca cctacggcgt gcagtgcttc gcccgctacc ccgaccacat gaagcagcac   240
gacttcttca gtccgccat gcccgaaggc tacgtccagg agcgcaccat cttcttcaag   300
gacgacggca actacaagac ccgcgccgag gtgaagttcg agggcgacac cctggtgaac   360
cgcatcgagc tgaagggcat cgacttcaag gaggacggca acatcctggg cacaagctg   420
gagtacaact acaacagcca aggtctatat atcaccgccg acaagcagaa gaacggcatc   480
aaggtgaact tcaagacccg ccacaacatc gaggacggca gcgtgcagct cgccgaccac   540
taccagcaga cacccccat cggcgacggc cccgtgctgc tgcccgacaa ccactacctg   600
agcacccagt ccgccctgag caaagaccc aacgagaagc gcgatcacat ggtcctgctg   660
gagttcgtga ccgccgccgg gatcactctc ggcatggacg agctgtacaa gtaa         714
```

<210> SEQ ID NO 123
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
```

```
ggcaagctga ccctgaagtt catctgcacc accggcaagc tgcccgtgcc ctggcccacc        180
ctcgtgacca ccctgaccca cggcgtgcag tgcttcagcc gctacccga ccacatgaag         240 cagcacgact tcttcaagtc cgccatgccc gaaggctacg tccaggagcg caccatcttc        300
ttcaaggacg acggcaacta caagacccgc gccgaggtga agttcgaggg cgacaccctg        360
gtgaaccgca tcgagctgaa gggcatcgac ttcaaggagg acggcaacat cctggggcac       420
aagctggagt acaactacaa cagccacaac gtctatatca tggccgacaa gcagaagaac       480
ggcatcaagg tgaacttcaa gatccgccac aacatcgagg acggcagcgt gcagctcgcc       540
gaccactacc agcagaacac ccccatcggc gacggccccg tgctgctgcc cgacaaccac      600
tacctgagca cccagtccgc cctgagcaaa gaccccaacg agaagcgcga tcacatggtc       660
ctgctggagt tcgtgaccgc cgccgggatc actctcggca tggacgagct gtacaagtaa      720
```

```
<210> SEQ ID NO 124
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
```

```
atggtgagca agggcgagga gctgttcacc ggggtggtgc ccatcctggt cgagctggac        60
ggcgacgtaa acgccacaa gttcagcgtg tccggcgagg gcgagggcga tgccacctac       120
ggcaagctga ccctgaagtt catctgcacc accggcaagc tgcccgtgcc ctggcccacc      180
ctcgtgacca ccctgaccta cggcgtgcag tgcttcagcc gctacccga ccacatgaag       240 cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac    600
tacctgagca cccagtccgc cctgagcaaa gaccccaacg agaagcgcga tcacatggtc     660
ctgctggagt tcgtgaccgc cgccgggatc actctcggca tggacgagct gtacaagtaa    720
```

```
<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ctcgtgacca ccttcaccta cgg                                                23
```

```
<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
```

-continued

```
atggtgagca agggcgagga gctg                                          24

<210> SEQ ID NO 127
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gtcctccttg aagtcgatgc cc                                            22
```

COMPOSITIONS AND METHODS FOR ENHANCING HOMOLOGOUS RECOMBINATION

CROSS-REFERENCES TO RELATED APPLICATIONS

This application claims the benefit of U.S. Provisional Application No. 62/342,504, filed May 27, 2016, the disclosure of is incorporated by reference in its entirety.

SEQUENCE LISTING

The instant application contains a Sequence Listing which has been submitted electronically in ASCII format and is hereby incorporated by reference in its entirety. Said ASCII copy, created on Jun. 14, 2017, is named LT01132_SL.txt and is 45,118 bytes in size.

FIELD

The present disclosure generally relates to compositions and methods for improving the efficiency of homologous recombination. In particular, the disclosure relates to reagents and the use of such reagents.

BACKGROUND

A number of genome-editing systems, such as designer zinc fingers, transcription activator-like effectors (TALEs), CRISPRs, and homing meganucleases, have been developed. One issue with these systems is low levels of homologous recombination often requires that numerous cells of clonal origin be screened to identify cells that have undergone homologous recombination and have the desired genotype. The generation and identification of cells with the correct genotype is often laborious and time consuming. In one aspect, the invention allows for the efficient design, preparation, and use of genome editing reagents and generation and identification of cells that have been "correctly" edited.

SUMMARY

The present disclosure relates, in part, to compositions and methods for editing of nucleic acid molecules. There exists a substantial need for efficient systems and techniques for modifying genomes. This invention addresses this need and provides related advantages.

One aspect of the invention involves the choice of features such as molecular structures and incubation conditions that result in increased gene editing efficiency. In some instances, donor nucleic acid molecules used in the practice of the invention have termini that are nuclease resistant. This is believed to assist in stabilizing termini against nuclease action (e.g., against endogenous nucleases).

The invention includes methods for performing homologous recombination. In some aspects, these methods comprise (a) generating a double-stranded break in a nucleic acid molecule present inside a cell to produce a cleaved nucleic acid molecule, and (b) contacting the cleaved nucleic acid molecule generated in (a) with a donor nucleic acid molecule, wherein the cleaved nucleic acid molecule and the donor nucleic acid molecule each contain matched termini on at least one end, wherein the matched termini on at least one end of the cleaved nucleic acid molecule and the donor nucleic acid molecule is at least ten (e.g., from about 10 to about 200, from about 10 to about 150, from about 10 to about 100, from about 10 to about 90, from about 10 to about 75, from about 20 to about 140, from about 30 to about 100, etc.) nucleotides in length, and wherein the matched region of the cleaved nucleic acid molecule is single-stranded or double-stranded and the matched region of the donor nucleic acid molecule is single-stranded. In some instances, the matched termini on at least one end of the cleaved nucleic acid molecule and the donor nucleic acid molecule have 5' overhangs or 3' overhangs. In other instances, the matched termini on at least one end of the cleaved nucleic acid molecule and the donor nucleic acid molecule have one 5' overhang and one 3' overhang. In specific instances, a pair of matched termini is used where the terminus of the cleaved nucleic acid molecule is blunt and the terminus of the donor nucleic acid molecule has a 3' overhang. Further, in some instances, at least one pair of matched termini of the cleaved nucleic acid molecule and the donor nucleic acid molecule share at least ten (e.g., from about ten to about fifty, from about ten to about forty, from about ten to about thirty, from about fifteen to about fifty, from about fifteen to about forty, from about fifteen to about thirty, etc.) complementary nucleotides. In some instances, the at least ten complementary nucleotides share at least 80%, at least 85%, at least 90%, at least 95%, or 100% sequence identity.

A number of compositions and methods may be used to generate cleaved nucleic acid. As examples, the nucleic acid molecules present inside cells may cleaved by one or more zinc finger-FokI fusion proteins, one or more TAL nucleases, one or more CRISPR complexes, or one or more argonaute-nucleic acid complexes.

Further, cleaved nucleic acid molecules may have at least one terminus with a single-stranded region. Also, double-stranded breaks in nucleic acid molecules present inside cells may be generated by the formation of two nicks, one in each strand of the nucleic acid molecules. Such nicks may be used to generate cleaved nucleic acid molecules having at least one blunt terminus. Further, nicks made in cleaved nucleic acid molecules may be located at a distance selected from the group consisting of (a) from about two nucleotides to about forty nucleotides, (b) from about four nucleotides to about thirty nucleotides, (c) from about five nucleotides to about twenty nucleotides, and (d) from about five nucleotides to about thirty nucleotides.

The invention also includes compositions and methods related to donor nucleic acid molecules comprising one or more nuclease resistant group. For example, the invention includes donor nucleic acid molecule containing one or more nuclease resistant groups in at least one strand of at least one terminus. Donor nucleic acid molecule may also contain one or more nuclease resistant groups in both strands of both termini. Further, donor nucleic acid molecule contains a single terminal phosphorothioate linkage in both strands of both termini. Along these lines, donor nucleic acid molecule contains two terminal phosphorothioate linkages in both strands of both termini.

The invention also includes compositions and methods related to donor nucleic acid molecules having asymmetric termini. By "asymmetric termini" it is meant that the termini differ in one or more feature related to homologous recombination. For example, the lengths of the terminal "matched" regions of sequence complementarity to the target locus may be different. Thus, one terminus may have forty nucleotides of sequence complementarity and the other terminus may have only fifteen nucleotides of sequence complementarity.

In many instances, one or both asymmetric termini of donor nucleic acid molecules will be partially or fully single-stranded.

The invention further includes methods for generating donor nucleic acid molecules containing one or more nuclease resistant group in at least one strand of at least one terminus. Such methods may comprise (a) generating two single-stranded nucleic acid molecules that share at least one region of sequence complementarity sufficient to allow for the two single-stranded nucleic acid molecules to hybridize to each other, wherein at least one of the two single-stranded nucleic acid molecules contains at least one nuclease resistant group, and (b) contacting the two single-stranded nucleic acid molecules with each other under conditions that allow for hybridization to produce a hybridized nucleic acid molecule. In some instances, the hybridized nucleic acid molecule contains at least one overhanging terminus and is the donor nucleic acid molecule. In other instances, the donor nucleic acid molecule may be generated by contacting the hybridized nucleic acid molecule generated in (b) with an exonuclease that is inhibited by the one or more (e.g., from about 1 to about 12, from about 1 to about 10, from about 1 to about 6, from about 1 to about 4, from about 2 to about 12, from about 2 to about 10, from about 2 to about 7, from about 2 to about 3, from about 4 to about 12, from about 8 to about 12, from about 8 to about 16, etc.) nuclease resistant group under conditions that allow for the digestion of one or both termini of the hybridized nucleic acid molecule until the exonuclease reaches the one or more nuclease resistant group, thereby generating the donor nucleic acid molecule. In some instances, two nuclease resistant groups will be present in both strands of both termini of donor nucleic acid molecule (see FIG. 3).

The invention also includes methods for generating donor nucleic acid molecules containing one or more nuclease resistant group in at least one strand (or both strands) of at least one terminus (or both termini). Such methods may comprise (a) generating two single-stranded nucleic acid molecules that share at least one region of sequence complementarity sufficient to allow for the two single-stranded nucleic acid molecules to hybridize to each other, wherein at least one of the two single-stranded nucleic acid molecules contains at least one nuclease resistant group, (b) contacting the two single-stranded nucleic acid molecules with each other under conditions that allow for the two molecules to hybridize, to generate a hybridized nucleic acid molecule, and (c) contacting the hybridized nucleic acid molecule with an exonuclease that is inhibited by the at least one nuclease resistant group under condition that allow for the formation of the donor nucleic acid molecule. In some instances, the donor nucleic acid molecules may contain at least one terminal nuclease resistant group. In certain instances, the nuclease resistant groups include phosphorothioate linkages.

Additionally, the invention includes methods for generating donor nucleic acid molecules containing one or more nuclease resistant group in at least one strand of at least one terminus. Such methods comprise (a) producing two single-stranded nucleic acid molecules capable of hybridizing with each other, wherein at least one of the two nucleic acid molecules contains at least one nuclease resistant group, and (b) contacting the two single-stranded nucleic acid molecules with each other under conditions that allow for the two molecules to hybridize, thereby generating the donor nucleic acid molecule, wherein the donor nucleic acid molecule contains at least one, terminal single-stranded region of at least ten nucleotides in length that has sequence complementarity to a locus in a cell, and wherein the at least one, terminal single-stranded region contains at least one nuclease resistant group.

In some aspects, the invention includes composition comprising partially double-stranded donor nucleic acid molecules comprising two regions, as well as methods for making and using such nucleic acid molecules. Further, the two regions comprising (a) a single-stranded region at least ten nucleotides in length and (b) a double-stranded region at least twenty base pairs in length, wherein the single-stranded region has sequence complementarity to a locus in a cell and at least one nuclease resistant group located on the non-overhanging strand within two nucleotides of the beginning of the double-stranded region. In some aspect, such compositions will further comprise a transfection reagent. Further, the partially double-stranded donor nucleic acid molecule may comprise at least one nuclease resistant group which forms a phosphorothioate linkage. In some instances, the last two internucleosidic linkages are phosphorothioate linkages. Also, the donor nucleic acid molecule may have one or more 5' overhangs or 3' overhangs. Additionally, the partially double-stranded donor nucleic acid molecule may have single-stranded regions at both termini.

In additional aspects, the invention includes methods for performing homologous recombination in a population of cells, the method comprising (a) contacting the population of cells with a nucleic acid cutting entity under conditions that allow for the generation of double-stranded break at a target locus in nucleic acid present inside cells of the population, to produce cells containing an intracellular cleaved nucleic acid molecule, and (b) introducing a donor nucleic acid molecule into cells generated in step (a) under conditions that allow for homologous recombination to occur, wherein homologous recombination occurs at the target locus in at least 20% of the cells of the population. In related aspects, the target locus and/or the donor nucleic acid molecule have one or more of the following characteristics (a) the target locus and the donor nucleic acid molecule share at least one matched terminus, (b) the donor nucleic acid molecule contains one or more nuclease resistant group, (c) donor nucleic acid molecule has asymmetric termini, (d) the target locus cut site is within 15 nucleotides of the location where alteration is desired, (e) the nucleic acid cutting entity, or components thereof, and the donor nucleic acid molecule are contacted with the cells of the population at different times, and/or (f) the amount of the donor nucleic acid molecule contacted with cells of the population is in a range that allows for efficient uptake and homologous recombination. Nucleic acid cutting entities that may be employed in such methods comprises one or more zinc finger-FokI fusion protein complex, one or more TAL nuclease, one or more CRISPR complex, or one or more argonaute-nucleic acid complex. Further, the donor nucleic acid molecule may have asymmetric termini of different lengths. In some embodiments, the asymmetric termini of different lengths may comprise single-stranded regions of different lengths. Single-stranded regions used in the practice of the invention may be less than 100 (e.g., from about 10 to about 95, from about 20 to about 95, from about 30 to about 95, from about 40 to about 95, from about 50 to about 95, from about 10 to about 75, from about 20 to about 75, from about 25 to about 95, from about 25 to about 60, etc.) nucleotides in length. In some instances, the matched termini of the target locus and the donor nucleic acid molecule are single-stranded regions that share 100% sequence complementarity. In related aspects, nucleic acid at the target locus may be blunt ended and the donor nucleic acid molecule may have a matched terminus that is single-stranded. In some instances, hybridization of the matched termini of the target locus and the donor nucleic acid molecule results in the formation of a junction region containing nicks in both strands. In other instances, hybridization of the matched termini of the target locus and the donor nucleic acid molecule results in the formation of a junction region that contains gaps of no more than two nucleotides in one or both strands. In specific embodiments, the matched termini of the target locus and the donor nucleic acid molecule comprise 5' single-stranded regions, 3' single-stranded regions, or both 5' and 3' single-stranded regions.

It has been found that co-delivery of all homologous recombination components, in some instances, results in decreased efficiency of homologous recombination. Thus, in some aspect of the invention, the cells of the population may be contacted with the nucleic acid cutting entity, or components thereof, before the cells of the population are contacted with the donor nucleic acid molecule. Further, the cells of the population are contacted with the nucleic acid cutting entity, or components thereof, for between 5 and 80 (e.g., from about 5 to about 60, from about 5 to about 50, from about 5 to about 45, from about 5 to about 40, from about 5 to about 35, from about 5 to about 30, from about 5 to about 25, from about 10 to about 50, from about 10 to about 40, from about 10 to about 30, from about 15 to about 40, etc.) minutes before the cells of the population are contacted with the donor nucleic acid molecule. In related, as well as other, aspect of the invention, the donor nucleic acid molecules may contain one or more nuclease resistant group at one or more terminus. Further, the donor nucleic acid molecules may contain two nuclease resistant groups at one or more terminus. In some aspects, the donor nucleic acid molecule may contain two nuclease resistant groups at each terminus. In additional aspects, the donor nucleic acid molecule may contain two nuclease resistant groups in each strand at each terminus. Further, the one or more nuclease resistant group may be phosphorothioate groups. In some aspects, the target locus cut site may be within 10 nucleotides of the location where alteration is desired. Further, the target locus cut site may comprise single stranded region that includes all or part of the location where alteration is desired. In addition, the single-stranded region contains a single mismatched nucleotide between the target locus and the donor nucleic acid molecule.

It has also been found that adjustment of the amount of donor nucleic acid affects the efficiency of homologous recombination. In some embodiments of the invention, the amount of donor nucleic acid may be between 50 and 900 ng (e.g., from about 50 to about 800, from about 50 to about 700, from about 50 to about 600, from about 50 to about 500, from about 50 to about 400, from about 50 to about 300, from about 150 to about 800, from about 150 to about 650, from about 150 to about 550, from about 150 to about 450, from about 200 to about 600, etc.) per $1 \times 10^5$ cells (e.g., animal cells, plant cells, insect cells, mammalian cells, human cells, rodent cells, etc.). Further, donor nucleic acid molecules may be introduced into cells of the population by any number of means, including electroporation or transfection.

BRIEF DESCRIPTION OF THE DRAWINGS

For a more complete understanding of the principles disclosed herein, and the advantages thereof, reference is made to the following descriptions taken in conjunction with the accompanying drawings, in which:

FIG. 6 discloses SEQ ID NOs: 1-3, respectively, from top to bottom.

FIG. 7. Sequential delivery of Cas9 RNP and donor DNA facilitated HDR. (A) Definition of PAM and non-PAM ssDNA donor. The PAM ssDNA donor is defined as the strand containing the NGG PAM sequence whereas the non-PAM ssDNA donor is defined as the strand complementary to the PAM strand. (B) PAM or non-PAM ssDNA (6 nt insertion). Cas9 RNP (Cas9 nuclease and the +5 gRNA) and a 97-mer PAM or non-PAM ssDNA oligonucleotide were co-delivered (RD) or sequentially delivered via electroporation to disrupted EmGFP stable cell lines with Cas9 RNP first and then donor (R→D) or donor first and then Cas9 RNP (D→R). A brief cell washing step was involved for sequential delivery. Two consecutive electroporations without wash of cells served as control (RDx2). The percentages of EmGFP-positive cells were determined by flow cytometry at 48 hours post transfection. (C) PAM ssDNA dose (6 nt insertion). Cas9 RNP and various amount of PAM ssDNA oligonucleotide were sequentially delivered to disrupted EmGFP stable cell lines via electroporation. 0.33 µg of a ssDNA oligonucleotide per 10 µl reaction was equivalent to approximately 1 µM final concentration. Samples in the absence of donor (+gRNA) or gRNA (−gRNA) were used as controls. (D) dsDNA donor (6 nt insert). Cas9 RNP and a 400 bp dsDNA donor were co-delivered (RD) or sequentially delivered (R→D) to disrupted EmGFP stable cell lines. Samples in the absence of donor (+gRNA) or gRNA (−gRNA) served as controls. (E) PAM ssDNA (1 nt substitution). Cas9 RNP (Cas9 nuclease and the eBFP gRNA) and a 100-mer PAM ssDNA oligonucleotide were co-delivered (RD) or sequentially delivered via electroporation to HEK293 cells stably expressing eBFP with Cas9 RNP first and then donor (R→D) or donor first and then Cas9 RNP (D→R). Samples in the absence of donor (+gRNA) or gRNA (−gRNA) served as controls. The percentages of GFP-positive cells were determined by flow cytometry at 48 hours post transfection.

FIG. 8. Effects of oligonucleotide length and modification on HDR. (A) PAM ssDNA (6 nt insertion). Cas9 RNP (Cas9 nuclease and the +5 gRNA) and various length of PAM ssDNA oligonucleotide with (PS) or without phosphorothioate modification were sequentially delivered to disrupted EmGFP stable cell lines via electroporation. Various length of PAM ssDNA oligonucleotide was normalized to either equal mass or equal molarity. Samples in the absence of donor (+gRNA) or gRNA (−gRNA) served as controls. The percentages of GFP-positive cells were determined by flow cytometry at 48 hours post transfection. (B) PAM ssDNA (1 nt substitution). Cas9 RNP and various length of PAM ssDNA oligonucleotide with (PS) or without phosphorothioate modification were sequentially delivered to HEK293 cells expressing eBFP. The percentages of GFP-positive cells were determined by flow cytometry at 48 hours post transfection. (C) Verification by sequencing. The eBFP genomic locus was PCR-amplified, followed by cloning and Sanger sequencing of 96 samples. The relative percentage of wild type (wt), NHEJ, and HDR was plotted. (D) Examples of mutations. Examples of edited clones (not representing the actual percentages of NHEJ and HDR). FIG. 8 discloses SEQ ID NOs: 4-14, respectively, from top to bottom.

FIG. 10. Asymmetric ssDNA donors enhanced HDR. (A) Asymmetric PAM or Non-PAM strand ssDNA annealing. Two separate gRNAs flanking the insertion site (↓ with a 0 above) were designed and synthesized with double-stranded breaks (DSB) occurred at position −3 and +5 separately (▲). Upon end recession of DSB, the 3' recessive ends were generated in two opposite orientations, which could anneal to either PAM (a) or non-PAM (b) ssDNA donors. The PAM ssDNA oligonucleotide is defined as the strand containing the NGG PAM sequence. (PAM ssDNA donor is defined as the PAM-containing strand) (B) Asymmetrical donor design. A series of ssDNA donors were designed with various number of nucleotides on the left arm (−) and right arm (+) of the insertion site. Both the PAM and non-PAM strands were tested. The Cas9 RNP (1.5 µg Cas9 nuclease, 360 ng gRNA) and ssDNA donors (10 pmol) were sequentially delivered to disrupted EmGFP stable HEK293 cell lines. At 48 hours post transfection, the % Indel was determined by the GCD assay (FIG. 9B), whereas the percentages of EmGFP-positive cells were determined by flow cytometry. The bar graphs ((C)—Normalized HDR efficiencies) represented the normalized HDR efficiency (% EmGFP+ cells/of % Indel) with averages of three individual experiments.

FIG. 11 discloses SEQ ID NOs: 15-24, respectively, from top to bottom.

FIG. 12. Various DSB repair pathways. (A) DNA repair through NHEJ pathway. (B) DNA repair by either PAM or non-PAM ssDNA oligonucleotide. (C) DNA repair by dsDNA donor. (D) DNA repair by dsDNA donor with 3' single-stranded overhangs.

FIG. 13. Generation of stable cell lines for HDR assays. (A) A disrupted EmGFP HEK293 stable cell line containing deletion of "CACCTT" (SEQ ID NO: 25) was generated by transfecting cells with Cas9 RNPs, followed by limiting dilution and clonal isolation. HDR assays were carried out by transfecting disrupted EmGFP HEK293 cells with Cas9 RNP and donor DNA, followed by flow cytometric analysis at 48 hours post transfection. Transfections without either donor DNA (Cas9 RNP) or gRNA (Cas9/donor) were used as controls. Fluorescence was only seen in the Cas9 RNP/Donor treated cells (data not shown). (B) A stable HEK293FT cell expressing eBFP gene was generated using Lentiviral delivery system. A point mutation from "C" to "T" would convert His66 to Tyr66, resulting in generation of a variant of GFP. HDR assays were performed by transfecting eBFP-expressing HEK293 cells with Cas9 RNP and donor DNA, followed by flow cytometric analysis to determine the percentage of GFP-positive cells at 48 hours post transfection. Transfections without either donor DNA (Cas9 RNP) or gRNA (Cas9/donor) served as controls. Green fluorescence was only seen in the Cas9 RNP/Donor treated cells (data not shown). FIG. 13 discloses SEQ ID NOs: 26-33, respectively, from top to bottom.

DETAILED DESCRIPTION

Figure 1:
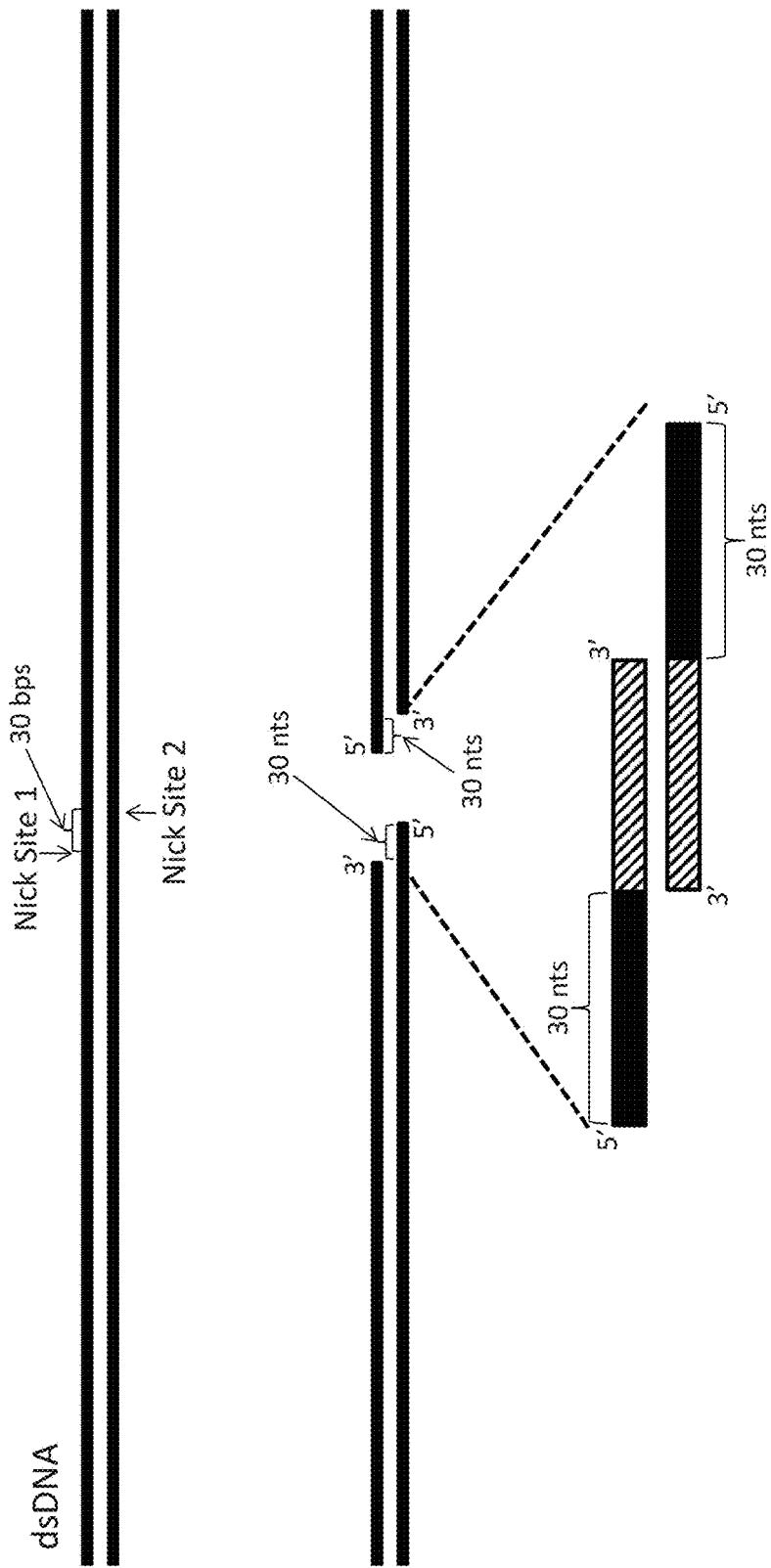
FIG. 1 is a schematic showing a nicking based nucleic acid cleavage strategy using a nick based cleavage system (e.g., a two nick site CRISPR system). In the top portion of the figure, two lines represent double-stranded nucleic acid. Two nick sites are indicated by Nick Site 1 and Nick Site 2. The center portion of the figure shows the result of nicking actions the two closely positioned nicks on different strands. The result in this instance is a double-stranded break, resulting in the formation of two thirty nucleotide 5' overhangs. The lower portion of this figure shows a nucleic acid segment with 5' termini that share sequence complementarity with the break site.

Definitions:

As used herein the term "homologous recombination" refers to a mechanism of genetic recombination in which two DNA strands comprising similar nucleotide sequences exchange genetic material. Cells use homologous recombination during meiosis, where it serves to rearrange DNA to create an entirely unique set of haploid chromosomes, but also for the repair of damaged DNA, in particular for the repair of double strand breaks. The mechanism of homologous recombination is well known to the skilled person and has been described, for example by Paques and Haber (Paques F, Haber J E.; *Microbiol. Mol. Biol. Rev.* 63:349-404 (1999)). In the method of the present invention, homologous recombination is enabled by the presence of said first and said second flanking element being placed upstream (5') and downstream (3'), respectively, of said donor DNA sequence each of which being homologous to a continuous DNA sequence within said target sequence.

As used herein the term "non-homologous end joining" (NEHJ) refers to cellular processes that join the two ends of double-strand breaks (DSBs) through a process largely independent of homology. Naturally occurring DSBs are generated spontaneously during DNA synthesis when the replication fork encounters a damaged template and during certain specialized cellular processes, including V(D)J recombination, class-switch recombination at the immunoglobulin heavy chain (IgH) locus and meiosis. In addition, exposure of cells to ionizing radiation (X-rays and gamma rays), UV light, topoisomerase poisons or radiomimetic drugs can produce DSBs. NHEJ (non-homologous end-joining) pathways join the two ends of a DSB through a process largely independent of homology. Depending on the specific sequences and chemical modifications generated at the DSB, NHEJ may be precise or mutagenic (Lieber M R., *The mechanism of double-strand DNA break repair by the nonhomologous DNA end-joining pathway. Annu Rev Biochem* 79:181-211).

As used herein the term "donor DNA" or "donor nucleic acid" refers to nucleic acid that is designed to be introduced into a locus by homologous recombination. Donor nucleic acid will have at least one region of sequence homology to the locus. In many instances, donor nucleic acid will have two regions of sequence homology to the locus. These regions of homology may be at one of both termini or may be internal to the donor nucleic acid. In many instances, an "insert" region with nucleic acid that one desires to be introduced into a nucleic acid molecules present in a cell will be located between two regions of homology (see FIG. 2).

As used herein the term "homologous recombination system or "HR system" refers components of systems set out herein that maybe used to alter cells by homologous recombination. In particular, zinc finger nucleases, TAL effector nucleases, CRISPR endonucleases, homing endonucleases, and argonaute editing systems.

As used herein the term "nucleic acid cutting entity" refers to a single molecule or a complex of molecules that has nucleic acid cutting activity (e.g., double-stranded nucleic acid cutting activity). Exemplary nucleic acid cutting entities include zinc finger proteins, transcription activator-like effectors (TALEs), CRISPR complexes, and homing meganucleases. In many instances, nucleic acid cutting entities will have an activity that allows them to be nuclear localized (e.g., will contain nuclear localization signals (NLS)).

As used herein the term "zinc finger protein (ZFP)" refers to a protein comprising refers to a polypeptide having nucleic acid (e.g., DNA) binding domains that are stabilized by zinc. The individual DNA binding domains are typically referred to as "fingers," such that a zinc finger protein or polypeptide has at least one finger, more typically two fingers, or three fingers, or even four or five fingers, to at least six or more fingers. In some aspect, ZFPs will contain three or four zinc fingers. Each finger typically binds from two to four base pairs of DNA. Each finger usually comprises an about 30 amino acids zinc-chelating, DNA-binding region (see, e.g., U.S. Pat. Publ. No. 2012/0329067 A1, the disclosure of which is incorporated herein by reference).

As used herein the term "transcription activator-like effectors (TAL)" refers to proteins composed of more than one TAL repeat and is capable of binding to nucleic acid in a sequence specific manner. In many instances, TAL effectors will contain at least six (e.g., at least 8, at least 10, at least 12, at least 15, at least 17, from about 6 to about 25, from about 6 to about 35, from about 8 to about 25, from about 10 to about 25, from about 12 to about 25, from about 8 to about 22, from about 10 to about 22, from about 12 to about 22, from about 6 to about 20, from about 8 to about 20, from about 10 to about 22, from about 12 to about 20, from about 6 to about 18, from about 10 to about 18, from about 12 to about 18, etc.) TAL repeats. In some instances, a TAL effector may contain 18 or 24 or 17.5 or 23.5 TAL nucleic acid binding cassettes. In additional instances, a TAL effector may contain 15.5, 16.5, 18.5, 19.5, 20.5, 21.5, 22.5 or 24.5 TAL nucleic acid binding cassettes. TAL effectors will generally have at least one polypeptide region which flanks the region containing the TAL repeats. In many instances, flanking regions will be present at both the amino and carboxyl termini of the TAL repeats. Exemplary TALs are set out in U.S. Pat. Publ. No. 2013/0274129 A1 and may be modified forms on naturally occurring proteins found in bacteria of the genera *Burkholderia, Xanthamonas* and *Ralstonia*.

In many instances, TAL proteins will contain nuclear localization signals (NLS) that allow them to be transported to the nucleus.

As used herein the term "CRISPR complex" refers to the CRISPR proteins and nucleic acid (e.g., RNA) that associate with each other to form an aggregate that has functional activity. An example of a CRISPR complex is a wild-type Cas9 (sometimes referred to as Csn1) protein that is bound to a guide RNA specific for a target locus. As used herein the term "CRISPR protein" refers to a protein comprising a nucleic acid (e.g., RNA) binding domain nucleic acid and an effector domain (e.g., Cas9, such as *Streptococcus pyogenes* Cas9). The nucleic acid binding domains interact with a first nucleic acid molecules either having a region capable of hybridizing to a desired target nucleic acid (e.g., a guide RNA) or allows for the association with a second nucleic acid having a region capable of hybridizing to the desired target nucleic acid (e.g., a crRNA). CRISPR proteins can also comprise nuclease domains (i.e., DNase or RNase domains), additional DNA binding domains, helicase domains, protein-protein interaction domains, dimerization domains, as well as other domains.

CRISPR protein also refers to proteins that form a complex that binds the first nucleic acid molecule referred to above. Thus, one CRISPR protein may bind to, for example, a guide RNA and another protein may have endonuclease activity. These are all considered to be CRISPR proteins because they function as part of a complex that performs the same functions as a single protein such as Cas9.

In many instances, CRISPR proteins will contain nuclear localization signals (NLS) that allow them to be transported to the nucleus.

As used herein, the term "target locus" refers to a site within a nucleic acid molecule that is recognized and cleavage by a nucleic acid cutting entity. When, for example, a single CRISPR complex is designed to cleave double-stranded nucleic acid, then the target locus is the cut site and the surrounding region recognized by the CRISPR complex. When, for example, two CRISPR complexes are designed to nick double-stranded nucleic acid in close proximity to create a double-stranded break, then the region surrounding recognized by both CRISPR complexes and including the break point is referred to as the target locus.

As used herein, the term "nuclease-resistant group" refers to a chemical group that may be incorporated into nucleic acid molecules and can inhibit by enzymes (exonucleases and/or endonucleases) degradation of nucleic acid molecules containing the group. Examples of such groups are phosphorothioate internucleotide linkages, 2'-O-methyl nucleotides, 2'-deoxy-2'-fluoro nucleotides, 2'-deoxy nucleotides, and 5-C-methyl nucleotides.

As used herein, the term "double-stranded break site" refers to a location in a nucleic acid molecule where a double-stranded break occurs. In many instances, this will be generated by the nicking of the nucleic acid molecule at two close locations (e.g., within from about 3 to about 50 base pairs, from about 5 to about 50 base pairs, from about 10 to about 50 base pairs, from about 15 to about 50 base pairs, from about 20 to about 50 base pairs, from about 3 to about 40 base pairs, from about 5 to about 40 base pairs, from about 10 to about 40 base pairs, from about 15 to about 40 base pairs, from about 20 to about 40 base pairs, etc.). Typically, nicks may be further apart in nucleic acid regions that contain higher AT content, as compared to nucleic acid regions that contain higher GC content.

As used herein, the term "matched termini" refers to termini of nucleic acid molecules that share sequence identity of greater than 90%. A matched terminus of a DS break at a target locus may be double-stranded or single-stranded. A matched terminus of a donor nucleic acid molecule will generally be single-stranded.

Overview:

The invention relates, in part, to compositions and methods for enhancing the efficiency of gene editing reactions via, for example, homologous recombination. The invention also related, in part, to increasing the homologous recombination (HR) to non-homologous end-joining (NHEJ) ratio. Both of these aspects of the invention may be achieved by the delivery of donor nucleic acid to a target locus by associating it with one or more nucleic acid cutting entities. While not wishing to be bound to theory, it is believed that both increased HR efficiency and increased HR as compared to NHEJ are the result of a high local concentration of donor nucleic acid at target loci that have a double-stranded (DS) break.

In some instances, methods of the invention employ at least one donor nucleic acid that has termini that is "matched" to termini of the cut site. Examples of some embodiments of compositions and methods of the invention are set out in FIG. 1. FIG. 1 shows two nicks sites designed to generate a double-stranded (DS) break in a DNA molecule. The DS break has two 5' overhangs of 30 nucleotides each. The DS donor nucleic acid molecules has two 5' overhangs of 30 nucleotides each with sequence complementarity to the 5' overhangs generated in the cut nucleic acid molecule.

In the instance shown in FIG. 1, the donor nucleic acid molecule is designed to hybridize to both termini of the cut nucleic acid molecule in a manner that a DNA ligase would be able to repair the cut site with an introduction of an "insert" nucleic acid segment into the cut nucleic acid molecule.

Figure 2:
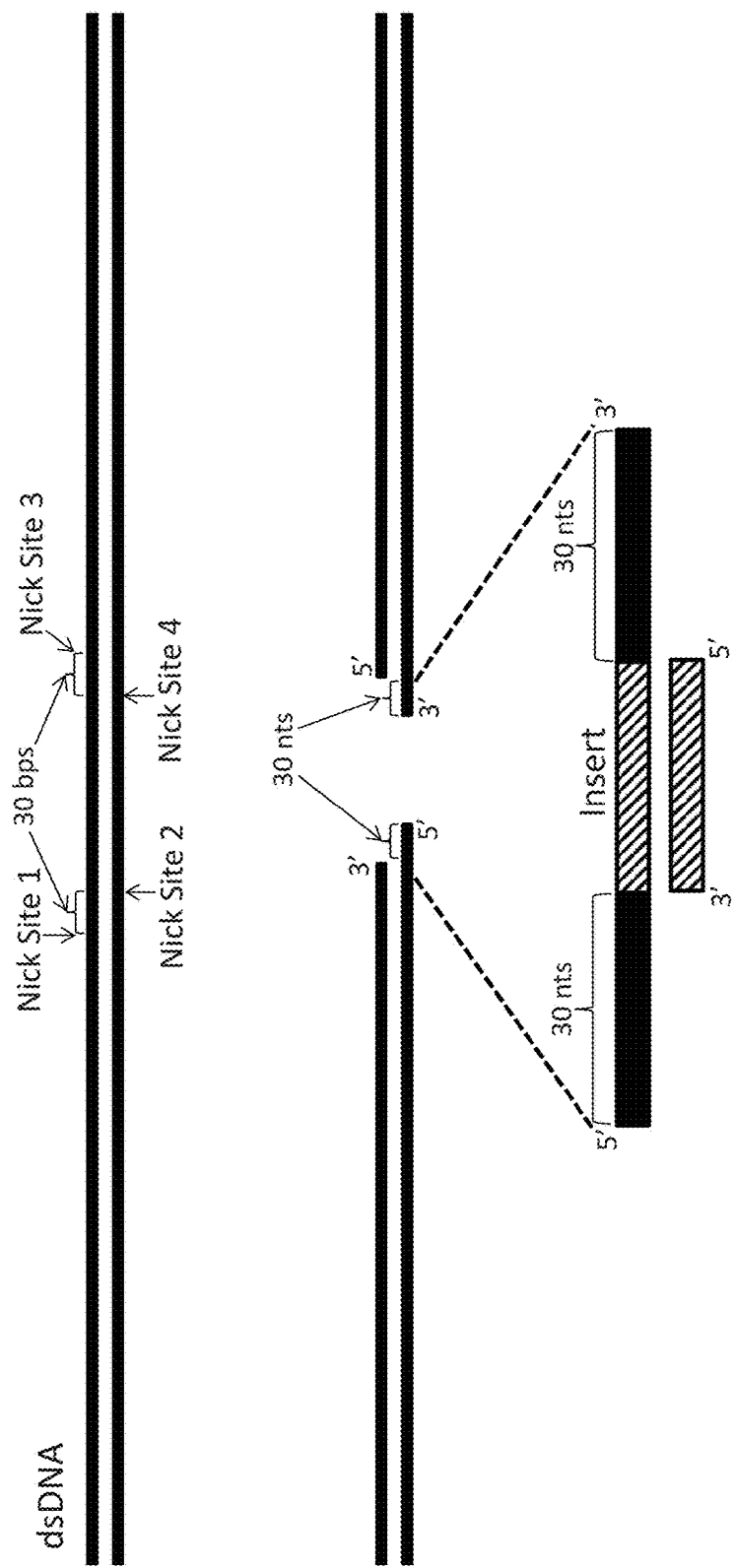
FIG. 2 is a schematic showing a nicking based nucleic acid cleavage strategy using a nick based cleavage system (e.g., a two nick site CRISPR system). As in FIG. 1, in the top portion of the figure, two lines represent double-stranded nucleic acid. Two closely associated nick sites are indicated by Nick Site 1 and Nick Site 2. Two additional closely associated nick sites are indicated by Nick Site 3 and Nick Site 4. Cutting at all four nick sites results in the formation of a nucleic acid molecule having the structure shown at the center of this figure. The result in this instance are a double-stranded breaks, resulting in the formation of a thirty nucleotide 5' overhang at one location and a thirty nucleotide 3' overhang at the other location. The lower portion of this figure shows a nucleic acid segment with a 5' terminus and a 3' terminus that each share sequence complementarity with the termini at the ends of the nucleic acid molecule represented in the center of this figure.

FIG. 2 shows another variation of the invention where four nicks are generated to remove a segment of the nucleic acid molecule that is cut. Further, the cut nucleic acid molecule has a 3' overhang at one terminus and a 5' overhang on the other terminus. The termini of the donor nucleic acid molecule are again designed to match those at the cut site.

In some aspects, the invention relates to compositions and methods for enhancing gene editing systems. Some of the features of such enhanced systems include one or more of the following: (1) delivery of one or more gene editing molecules (e.g., Cas9, gRNA, mRNA encoding a TAL effector, etc.) and donor nucleic acid molecules at different times, (2) the "matching" of termini between target loci and donor nucleic acid molecules, (3) designing of termini between target loci and donor nucleic acid molecules to maximize recombination efficiency, (4) adjustment of the amount of donor nucleic acid that the cells are contacted with, (5) the amount of donor nucleic acid delivered per cell (e.g., the average number of donor nucleic acid molecule delivered per cell), (6) protection of terminal regions of donor nucleic acid molecules from nucleases, and (7) the use of donor nucleic acid molecules with asymmetric single-stranded termini (e.g., one terminal single-stranded region is of a different length that the terminal single-stranded region).

Donor Nucleic Acid Molecules and Homologous Recombination

Donor nucleic acids will typically contain regions of homology corresponding to nucleic acid at or near a target locus. Exemplary donor nucleic acid molecules are shown in FIGS. 1-5. Using the nucleic acid molecules set out in FIG. 3 for purposes of illustration, donor nucleic acid may be single-stranded (SS) or double-stranded (DS) and it may be blunted ended on one or both ends or it may have overhangs on one or both ends. Further, overhangs, when present, may be 5', 3' or 3' and 5'. Also, the lengths of overhangs may vary. Donor nucleic acid molecules will often also contain an "insert" region that may be from about one nucleotide to about several thousand nucleotides.

In one aspect of the invention it has been found that the efficiency of homologous recombination is enhanced when one or both termini of donor nucleic acid molecules "matches" that of the DS break into which it is designed to be introduced into. Further, upon entry into cells (as well as prior to cellular entry), donor nucleic acid molecules may be exposed to nucleases (e.g., endonucleases, endonucleases, etc.). In order to limit the action of endonucleases with respect to altering donor nucleic acid molecule, one or more nuclease resistant group may be present.

Figure 3:
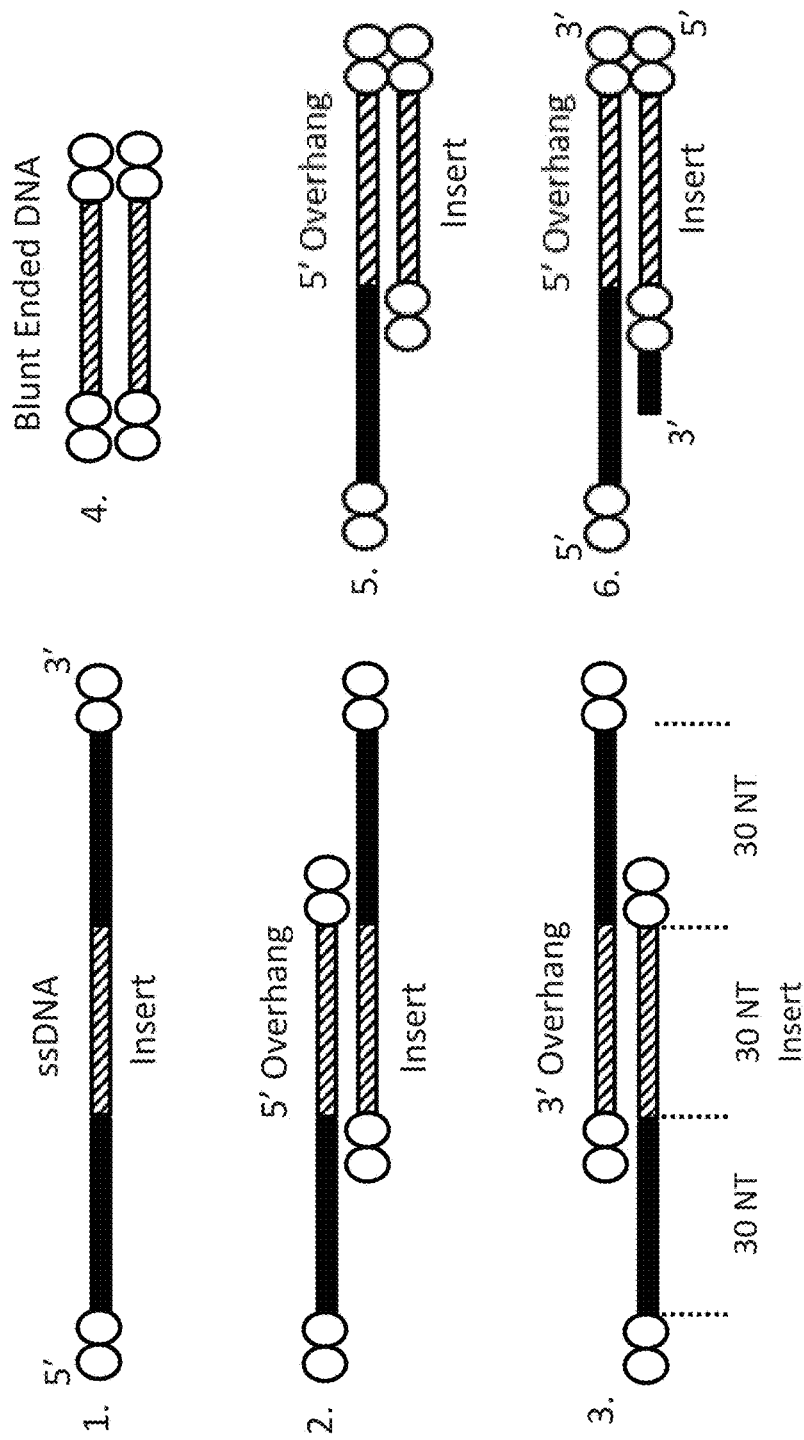
FIG. 3 shows a number of different formats of nucleic acid segments that may be used in various embodiments of the invention. The open circles at the termini represent nuclease resistant groups. Two circles mean that there are two groups. The black areas represent regions of sequence homology/complementarity with one or more locus of another nucleic acid molecule (e.g., chromosomal DNA). The cross hatched areas represent nucleic acid located between regions of sequence homology/complementarity in nucleic acid segments. This figure shows five different variations of nucleic acid segments that may be sued in different aspects of the invention.
Figure 4:
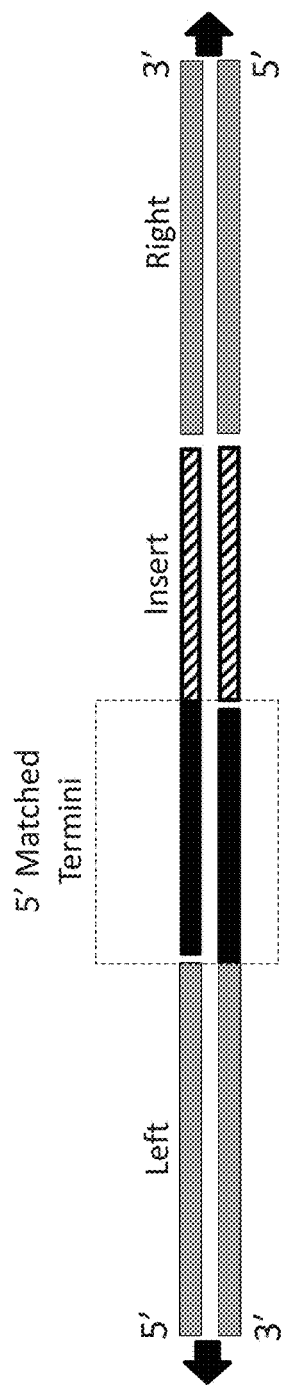
FIG. 4 is a representation of a nucleic acid segment hybridized to different termini nucleic acid termini. The nucleic acid molecule on the left side has a 3' overhang. The nucleic acid molecule on the right side is blunt ended. The nucleic acid segment (shown in the middle) has a 5' overhang that share sequence complementarity with the 3' overhang of the nucleic acid molecule on the left side.
Figure 5:
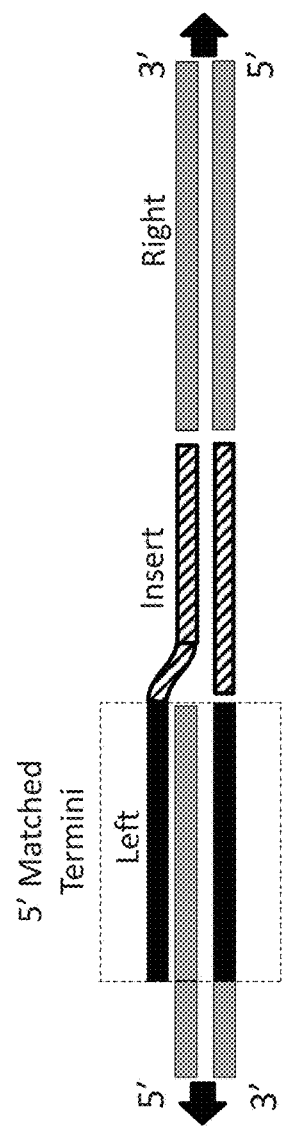
FIG. 5 is a representation similar to that shown in FIG. 4 with the exception that the end of the matched terminus of cleaved nucleic molecule is double-stranded and the matched terminus of the donor nucleic acid molecule is single-stranded. The black region represents complementary nucleic acid regions.

FIG. 3 shows a number of variations of donor nucleic acid molecules that may be used in aspects of the invention. The open circles at the termini represent nuclease resistant groups. Such groups may be located at a number of places in the donor nucleic acid molecules. Donor nucleic acid molecule number 6 shows a 3' terminal region of the lower strand that is located past the nuclease resistant groups. In some instances, cellular nucleases will digest this portion of the donor nucleic acid molecule. These nucleases will either stop or be slowed down by the nuclease resistant group, thereby stabilizing the structure of the terminus of the 3' region of the lower strand.

The invention thus includes compositions comprising nucleic acid molecules containing one or more (e.g., one, two, three, four, five, six, seven, etc.) nuclease resistant groups, as well as methods for making and using such donor nucleic acid molecules. In many instances, nuclease resistant groups will be located or one or both termini of donor nucleic acid molecules. Donor nucleic acid molecules may contain groups interior form one or both termini. In many instances, some or all of such donor nucleic acid molecules will be processed within cells to generate termini that match DS break sites.

The homology regions may be of varying lengths and may have varying amounts of sequence identity with nucleic acid at the target locus. Typically, homologous recombination efficiency increases with increased lengths and sequence identity of homology regions. The length of homology regions employed is often determined by factors such as fragility of large nucleic acid molecules, transfection efficiency, and ease of generation of nucleic acid molecules containing homology regions.

Homology regions may be from about 20 bases to about 10,000 bases in total length (e.g., from about 20 bases to about 100 bases, from about 30 bases to about 100 bases, from about 40 bases to about 100 bases, from about 50 bases to about 8,000 bases, from about 50 bases to about 7,000 bases, from about 50 bases to about 6,000 bases, from about 50 bases to about 5,000 bases, from about 50 bases to about 3,000 bases, from about 50 bases to about 2,000 bases, from about 50 bases to about 1,000 bases, from about 50 bases to about 800 bases, from about 50 bases to about 600 bases, from about 50 bases to about 500 bases, from about 50 bases to about 400 bases, from about 50 bases to about 300 bases, from about 50 bases to about 200 bases, from about 100 bases to about 8,000 bases, from about 100 bases to about 2,000 bases, from about 100 bases to about 1,000 bases, from about 100 bases to about 700 bases, from about 100 bases to about 600 bases, from about 100 bases to about 400 bases, from about 100 bases to about 300 bases, from about 150 bases to about 1,000 bases, from about 150 bases to about 500 bases, from about 150 bases to about 400 bases, from about 200 bases to about 1,000 bases, from about 200 bases to about 600 bases, from about 200 bases to about 400 bases, from about 200 bases to about 300 bases, from about 250 bases to about 2,000 bases, from about 250 bases to about 1,000 bases, from about 350 bases to about 2,000 bases, from about 350 bases to about 1,000 bases, etc.).

In some instances, it may be desirable to use regions of sequence homology that are less than 200 bases in length. This will often be the case when the donor nucleic acid molecule contains a small insert (e.g., less than about 300 bases) and/or when the donor nucleic acid molecule has one or two overhanging termini that match the DS break site.

Overhanging termini may be of various lengths and may be of different lengths at each end of the same donor nucleic acid molecules. In many instances, these overhangs will form the regions of sequence homology. FIG. 3, for example, shows a series of donor nucleic acid molecule that have 30 nucleotide single-stranded overhangs. These donor nucleic acid molecules are single-stranded and double-stranded. Donor nucleic acid molecule number 1 in FIG. 3 is a single-stranded molecule that has 30 nucleotides of sequence homology with an intended DS break site, a 30 nucleotide insert, and two nuclease resistant groups at each terminus. While a donor nucleic acid molecule of this type can be used with a number of DS break sites, it may also be sued with a DS break site of the type shown in FIG. 2. Thus, the invention includes compositions and methods for the introduction of single-stranded donor nucleic acid molecules into a target locus.

The amount of sequence identity the homologous regions share with the nucleic acid at the target locus, typically the higher the homologous recombination efficiency. High levels of sequence identity are especially desired when the homologous regions are fairly short (e.g., 50 bases). Typically, the amount of sequencer identity between the target locus and the homologous regions will be greater than 90% (e.g., from about 90% to about 100%, from about 90% to about 99%, from about 90% to about 98%, from about 95% to about 100%, from about 95% to about 99%, from about 95% to about 98%, from about 97% to about 100%, etc.).

As used herein, "percentage of sequence identity" means the value determined by comparing two optimally aligned nucleotide sequences over a comparison window, wherein the portion of the nucleotide sequence in the comparison window may comprise additions or deletions (i.e., sequence alignment gaps) as compared to the reference sequence (which does not comprise additions or deletions) for optimal alignment of the two sequences. In other words, sequence alignment gaps are removed for quantification purposes. The percentage of sequence identity is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

One method for determining sequence identity values is through the use of the BLAST 2.0 suite of programs using default parameters (Altschul et al., Nucleic Acids Res. 25:3389-3402 (1997)). Software for performing BLAST analyses is publicly available, e.g., through the National Center for Biotechnology-Information.

The insert region of donor nucleic acid molecules may be of a variety of lengths, depending upon the application that it is intended for. In many instances, donor nucleic acid molecules will be from about 1 to about 4,000 bases in length (e.g., from about 1 to 3,000, from about 1 to 2,000, from about 1 to 1,500, from about 1 to 1,000, from about 2 to 1,000, from about 3 to 1,000, from about 5 to 1,000, from about 10 to 1,000, from about 10 to 400, from about 10 to 50, from about 15 to 65, from about 2 to 15, etc. bases).

The invention also provide compositions and methods for the introduction into intracellular nucleic acid of a small number of bases (e.g., from about 1 to about 10, from about 1 to about 6, from about 1 to about 5, from about 1 to about 2, from about 2 to about 10, from about 2 to about 6, from about 3 to about 8, etc.). For purposes of illustration, a donor nucleic acid molecule may be prepared that is fifty-one bases pairs in length. This donor nucleic acid molecule may have two homology regions that are 25 base pairs in length with the insert region being a single base pair. When nucleic acid surrounding the target locus essentially matches the regions of homology with no intervening base pairs, homologous recombination will result in the introduction of a single base pair at the target locus. Homologous recombination reactions such as this can be employed, for example, to disrupt protein coding reading frames, resulting in the introduction of a frame shift in intracellular nucleic acid. The invention thus provides compositions and methods for the introduction of one or a small number of bases into intracellular nucleic acid molecules.

The invention further provides compositions and methods for the alteration of short nucleotide sequences in intracellular nucleic acid molecules. One example of this would be the change of a single nucleotide position, with one example being the correction or alteration of a single-nucleotide polymorphism (SNP). Using SNP alteration for purposes of illustration, a donor nucleic acid molecule may be designed with two homology regions that are 25 base pairs in length. Located between these regions of homology is a single base pair that is essentially a "mismatch" for the corresponding base pair in the intracellular nucleic acid molecules. Thus, homologous recombination may be employed to alter the SNP by changing the base pair to either one that is considered to be wild-type or to another base (e.g., a different SNP). Cells that have correctly undergone homologous recombination may be identified by later sequencing of the target locus.

Donor nucleic acid may also contain elements desired for insertion (i.e., an insert) into an intracellular nucleic acid molecule (e.g., a chromosome or plasmid) by homologous recombination. Such elements may be selectable markers (e.g., a positive selectable marker such as an antibiotic resistance marker), promoter elements, non-selectable marker protein coding nucleic acid (e.g., nucleic acid encoding cytokines, growth factors, etc.). Inserts may also encode detectable proteins such as luciferase and fluorescent proteins such as green fluorescent protein and yellow fluorescent protein).

Compositions and methods of the invention are designed to result in high efficiency of homologous recombination in cells (e.g., eukaryotic cells such as plant cells and animal cells, such as insect cells mammalian cells, including mouse, rat, hamster, rabbit and human cells). In some instances, homologous recombination efficiency is such that greater than 20% of cells in a population will have underdone homologous recombination at the desired target locus or loci. In some instances, homologous recombination may occur within from about 10% to about 65%, from about 15% to about 65%, from about 20% to about 65%, from about 30% to about 65%, from about 35% to about 65%, from about 10% to about 55%, from about 20% to about 55%, from about 30% to about 55%, from about 35% to about 55%, from about 40% to about 55%, from about 10% to about 45%, from about 20% to about 45%, from about 30% to about 45%, from about 40% to about 45%, from about 30% to about 50%, etc. of cell in a population.

Further, the invention includes compositions and methods for increasing the efficiency of homologous recombination within cells. For example, if homologous recombination occurs in 10% of a cell population under one set of conditions and in 40% of a cell population under another set of conditions, then the efficiency of homologous recombination has increased by 300%. In some aspects of the invention, the efficiency of homologous recombination may increase by from about 100% to about 500% (e.g., from about 100% to about 450%, from about 100% to about 400%, from about 100% to about 350%, from about 100% to about 300%, from about 200% to about 500%, from about 200% to about 400%, from about 250% to about 500%, from about 250% to about 400%, from about 250% to about 350%, from about 300% to about 500%, etc.).

One example of a set of conditions for which the efficiency of homologous recombination may be measured is where two identical donor nucleic acid molecules are used, where one has unmodified termini and the other has two phosphorothioate groups on each strand of each terminus. It has been found that such nuclease resistant groups can be used to increase the efficiency of homologous recombination. Further, such donor nucleic acid molecules may have termini that match the DS break site in at the target locus. Regardless of the various parameters used for the homologous recombination reactions, the invention includes compositions and methods for increasing the efficiency of homologous recombination.

One homologous recombination assay that may be used in the practice of the invention is set out in the examples and employs the incorporation into a nucleic acid molecule by homologous recombination a restriction site. Other assays involve nucleotide sequencing. Numerous other methods are known in the art.

In many instances, target loci will be cleaved in a manner that will result in blunt termini. In many instances, blunt ended matched termini will be contacted with donor nucleic acid molecules having single-stranded matched termini. In such instances, it has been found that single nucleotides at target loci can be replaced with nucleotides in donor nucleic acid molecules, when the target loci nucleotides are near the DS break (e.g., within 10 nucleotides of termini).

While not wishing to be bound by theory, it is thought that the above is due to 5' strand resection, followed by favoring of the terminus of donor nucleic acid molecules in the repair process. Further, the closer to the DS break (up to about 10 nucleotides), the higher the probability that the target locus base will be replaced with a donor nucleic acid molecule base during the repair process. Thus, the invention includes compositions and methods for the introduction of single-base changes at a target locus, the method comprising generating a DS break (e.g., a blunt ended break) at the target locus, followed by contacting the break point with a donor nucleic acid molecule having a single base substitution in the cognate matching terminus. In most instances, the single base to be substituted will be positioned within 1, 2, 3, 4, 5, or 6 bases of the terminus of the target locus.

Nucleic Acid Cutting Entities

The invention relates, in part, to gene editing resulting from the interaction of donor nucleic acid molecules with target loci. A number of mechanisms and/or gene editing systems may be used to generate DS breaks at target loci. The mechanism used to generate DS breaks at target loci will typically be selected based upon a number of factors such as efficiency of DS break generation at target loci, the ability to generate DS break generation at suitable locations at or near target loci, low potential for DS break generation at undesired loci, low toxicity, and cost issues. A number of these factors will vary with the cell employed and target loci.

A number of gene editing systems that may be used in the practice of the invention are known in the art. These include zinc finger nucleases, TAL effector nucleases, CRISPR endonucleases, homing endonucleases, and argonaute editing systems.

In most instances, nucleic acid cutting entity components will be either proteins or nucleic acids or a combination of the two but they may be associated with cofactors and/or other molecules.

A. Zinc Finger Based Systems

Zinc-finger nucleases (ZFNs) and meganucleases are examples of genome engineering tools that can be used to generate DS breaks in the practice of the invention. ZFNs are chimeric proteins consisting of a zinc-finger DNA-binding domain and a nuclease domain. One example of a nuclease domain is the non-specific cleavage domain from the type IIS restriction endonuclease FokI (Kim, Y G; Cha, J., Chandrasegaran, S. Hybrid restriction enzymes: zinc finger fusions to Fok I cleavage domain Proc. Natl. Acad. Sci. USA. 1996 Feb. 6; 93(3):1156-60) typically separated by a linker sequence of 5-7 base pairs. A pair of the FokI cleavage domain is generally required to allow for dimerization of the domain and cleavage of a non-palindromic target sequence from opposite strands. The DNA-binding domains of individual $Cys_2His_2$ ZFNs typically contain between 3 and 6 individual zinc-finger repeats and can each recognize between 9 and 18 base pairs.

One problem associated with ZNFs is the possibility of off-target cleavage which may lead to random integration of donor DNA or result in chromosomal rearrangements or even cell death which still raises concern about applicability in higher organisms (Zinc-finger Nuclease-induced Gene Repair With Oligodeoxynucleotides: Wanted and Unwanted Target Locus Modifications Molecular Therapy vol. 18 no. 4, 743-753 (2010)).

B. TAL Effectors Based Systems

Transcription activator-like (TAL) effectors represent a class of DNA binding proteins secreted by plant-pathogenic bacteria of the species, such as *Xanthomonas* and *Ralstonia*, via their type III secretion system upon infection of plant cells. Natural TAL effectors specifically have been shown to bind to plant promoter sequences thereby modulating gene expression and activating effector-specific host genes to facilitate bacterial propagation (Römer, P., et al., Plant pathogen recognition mediated by promoter activation of the pepper Bs3 resistance gene. Science 318, 645-648 (2007); Boch, J. & Bonas, U. *Xanthomonas* AvrBs3 family-type III effectors: discovery and function. Annu. Rev. Phytopathol. 48, 419-436 (2010); Kay, S., et al. U. A bacterial effector acts as a plant transcription factor and induces a cell size regulator. Science 318, 648-651 (2007); Kay, S. & Bonas, U. How *Xanthomonas* type III effectors manipulate the host plant. Curr. Opin. Microbiol. 12, 37-43 (2009)).

Natural TAL effectors are generally characterized by a central repeat domain and a carboxyl-terminal nuclear localization signal sequence (NLS) and a transcriptional activation domain (AD). The central repeat domain typically consists of a variable amount of between 1.5 and 33.5 amino acid repeats that are usually 33-35 residues in length except for a generally shorter carboxyl-terminal repeat referred to as half-repeat. The repeats are mostly identical but differ in certain hypervariable residues. DNA recognition specificity of TAL effectors is mediated by hypervariable residues typically at positions 12 and 13 of each repeat—the so-called repeat variable diresidue (RVD) wherein each RVD targets a specific nucleotide in a given DNA sequence. Thus, the sequential order of repeats in a TAL protein tends to correlate with a defined linear order of nucleotides in a given DNA sequence. The underlying RVD code of some naturally occurring TAL effectors has been identified, allowing prediction of the sequential repeat order required to bind to a given DNA sequence (Boch, J. et al. Breaking the code of DNA binding specificity of TAL-type III effectors. Science 326, 1509-1512 (2009); Moscou, M. J. & Bogdanove, A. J. A simple cipher governs DNA recognition by TAL effectors. Science 326, 1501 (2009)). Further, TAL effectors generated with new repeat combinations have been shown to bind to target sequences predicted by this code. It has been shown that the target DNA sequence generally start with a 5' thymine base to be recognized by the TAL protein.

The modular structure of TALs allows for combination of the DNA binding domain with effector molecules such as nucleases. In particular, TAL effector nucleases allow for the development of new genome engineering tools known.

TAL effectors used in the practice of the invention may generate DS breaks or may have a combined action for the generation of DS breaks. For example, TAL-FokI nuclease fusions can be designed to bind at or near a target locus and form double-stranded nucleic acid cutting activity by the association of two FokI domains.

C. CRISPR Based Systems

Gene altering reagents may be based upon CRISPR systems. The term "CRISPR" is a general term that applies to three types of systems, and system sub-types. In general, the term CRISPR refers to the repetitive regions that encode CRISPR system components (e.g., encoded crRNAs). Three types of CRISPR systems (see Table 1) have been identified, each with differing features.

TABLE 1

CRISPR System Types Overview

| System | Features | Examples |
|---|---|---|
| Type I | Multiple proteins (5-7 proteins typical), crRNA, requires PAM. DNA Cleavage is catalyzed by Cas3. | *Staphylococcus epidermidis* (Type IA) |
| Type II | 3-4 proteins (one protein (Cas9) has nuclease activity) two RNAs, requires PAMs. Target DNA cleavage catalyzed by Cas9 and RNA components. | *Streptococcus pyogenes* CRISPR/Cas9, *Francisella novicida* U112 Cpf1 |
| Type III | Five or six proteins required for cutting, number of required RNAs unknown but expected to be 1, PAMs not required. Type IIIB systems have the ability to target RNA. | *S. epidermidis* (Type IIIA); *P. furiosus* (Type IIIB). |

While the invention has numerous aspects and variations associated with it, the Type II CRISPR/Cas9 system has been chosen as a point of reference for explanation herein.

In certain aspects, the invention provides stabilized crRNAs, tracrRNAs, and/or guide RNAs (gRNAs), as well as collections of such RNA molecules.

Figure 6:
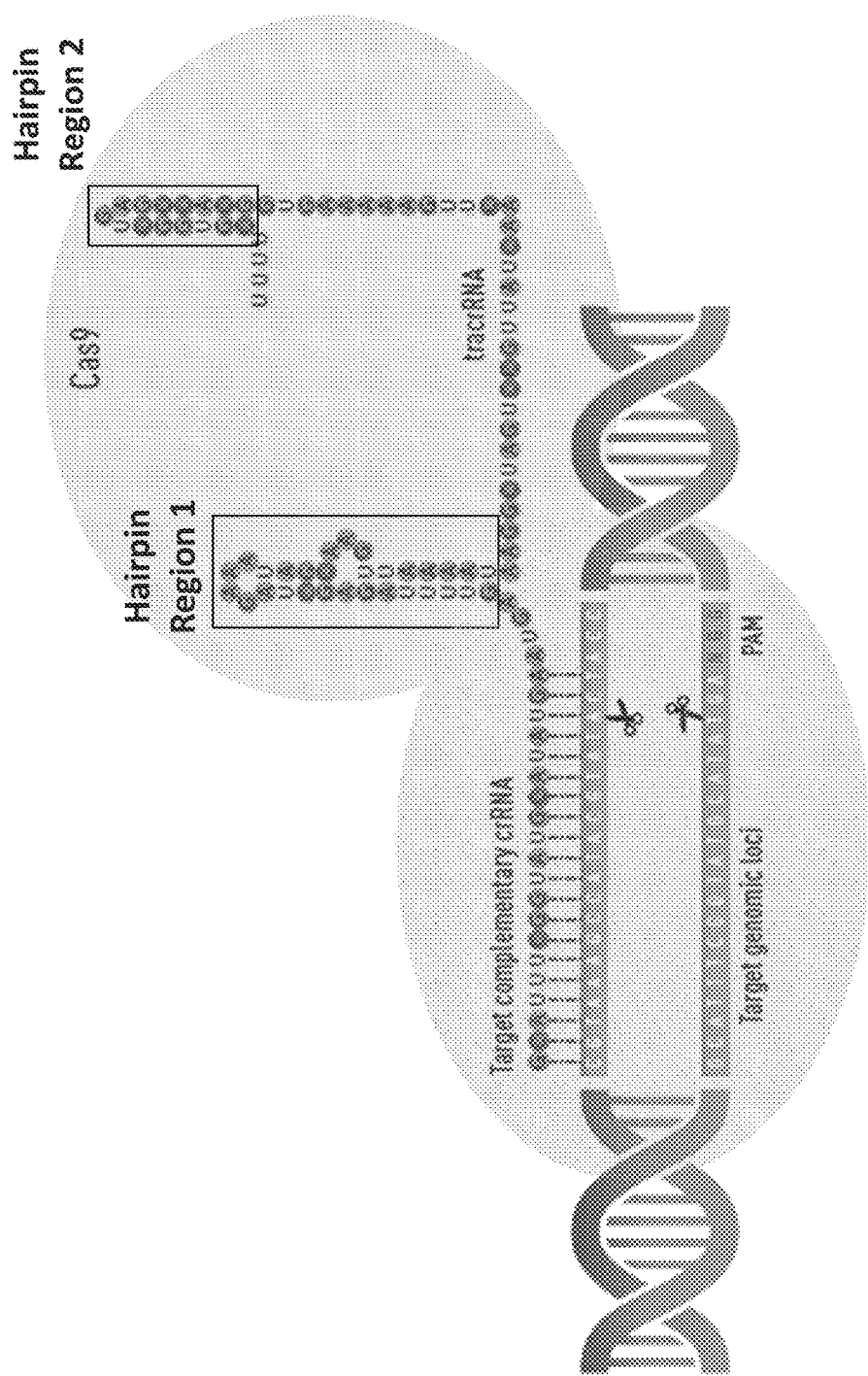
FIG. 6 is a schematic of a guide RNA molecule (104 nucleotides) showing the guide RNA bound to both Cas9 protein and a target genomic locus. Hairpin Region 1 is formed by the hybridization of complementary crRNA and tracrRNA regions joined by the nucleotides GAAA. Hairpin Region 2 is formed by a complementary region in the 3' portion of the tracrRNA.

FIG. 6 shows components and molecular interactions associated with a Type II CRISPR system. In this instance, the Cas9 mediated *Streptococcus pyogenes* system is exemplified. A gRNA is shown in FIG. 6 hybridizing to both target DNA (Hybridization Region 1) and tracrRNA (Hybridization Region 2). In this system, these two RNA molecules serve to bring the Cas9 protein to the target DNA sequence is a manner that allows for cutting of the target DNA. The target DNA is cut at two sites, to form a double-stranded break.

CRISPRs used in the practice of the invention may generate DS breaks or may have a combined action for the generation of DS breaks. For example, mutations may be introduced into CRISPR components that prevent CRISPR complexes from making DS breaks but still allow for these complexes to nick DNA. Mutations have been identified in Cas9 proteins that allow for the preparation of Cas9 proteins that nick DNA rather than making double-stranded cuts. Thus, the invention includes the use of Cas9 proteins that have mutations in RuvC and/or HNH domains that limit the nuclease activity of this protein to nicking activity.

CRISPR systems that may be used in the practice of the invention vary greatly. These systems will generally have the functional activities of a being able to form complex comprising a protein and a first nucleic acid where the complex recognizes a second nucleic acid. CRISPR systems can be a type I, a type II, or a type III system. Non-limiting examples of suitable CRISPR proteins include Cas3, Cas4, Cas5, Cas5e (or CasD), Cas6, Cas6e, Cas6f, Cas7, Cas8a1, Cas8a2, Cas8b, Cas8c, Cas9, Cas10, Casl Od, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966.

In some embodiments, the CRISPR protein (e.g., Cas9) is derived from a type II CRISPR system. In specific embodiments, the CRISPR system is designed to acts as an oligonucleotide (e.g., DNA or RNA)-guided endonuclease derived from a Cas9 protein. The Cas9 protein for this and other functions set out herein can be from *Streptococcus pyogenes*, *Streptococcus thermophilus*, *Streptococcus* sp., *Nocardiopsis dassonvillei*, *Streptomyces pristinaespiralis*, *Streptomyces viridochromogenes*, *Streptomyces viridochromogenes*, *Streptosporangium roseum*, *Streptosporangium roseum*, *AlicyclobacHlus acidocaldarius*, *Bacillus pseudomycoides*, *Bacillus selenitireducens*, *Exiguobacterium sibiricum*, *Lactobacillus delbrueckii*, *Lactobacillus salivarius*, *Microscilla marina*, *Burkholderiales bacterium*, *Polaromonas naphthalenivorans*, *Polaromonas* sp., *Crocosphaera watsonii*, *Cyanothece* sp., *Microcystis aeruginosa*, *Synechococcus* sp., *Acetohalobium arabaticum*, *Ammonifex degensii*, *Caldicelulosiruptor becscii*, *Candidatus Desulforudis*, *Clostridium botulinum*, *Clostridium difficile*, *Finegoldia magna*, *Natranaerobius thermophilus*, *Pelotomaculumthermopropionicum*, *Acidithiobacillus caldus*, *Acidithiobacillus ferrooxidans*, *Allochromatium vinosum*, *Marinobacter* sp., *Nitrosococcus halophilus*, *Nitrosococcus watsoni*, *Pseudoalteromonas haloplanktis*, *Ktedonobacter racemifer*, *Methanohalobium evestigatum*, *Anabaena variabilis*, *Nodularia spumigena*, *Nostoc* sp., *Arthrospira maxima*, *Arthrospira platensis*, *Arthrospira* sp., *Lyngbya* sp., *Microcoleus chthonoplastes*, *Oscillatoria* sp., *Petrotoga mobilis*, *Thermosipho africanus*, or *Acaryochloris marina*.

D. Argonaute Gene Editing Systems

The argonaute family of proteins are endonucleases that use 5' phosphorylated single-stranded nucleic acids as guides to cleave nucleic acid targets. These proteins, like Cas9, are believed to have roles in gene expression repression and defense against exogenous nucleic acids.

Argonaute proteins differ from Cas9 in a number of ways. Unlike Cas9, which exist only in prokaryotes, argonaute proteins are evolutionarily conserved and are present in almost all organisms. Some argonaute proteins have been found to bind single-stranded DNAs and cleave target DNA molecules. Further, no specific consensus secondary structure of guides is required for argonaute binding and no sequence like a CRISPR system PAM site is required. It has been shown that the argonaute protein of *Natronobacterium gregoryi* can be programmed with single-stranded DNA guides and used as a genome editing in mammalian cells (Gao et al., *Nature Biotech.*, May 2, 2016; doi:10.1038/nbt.3547).

Argonaute proteins require a 5' phosphorylated single-stranded guide DNA molecule that is about 24 nucleotides in length. The amino acid sequence of an argonaute that may be used in the practice of the invention is set out in Table 2.

TABLE 2

Natronobacterium gregoryi Argonaute Amino Acid Sequence (SEQ ID NO: 34)

| | | | |
|---|---|---|---|
| 1 | MTVIDLDSTT | TADELTSGHT | YDISVTLTGV YDNTDEQHPR MSLAFEQDNG ERRYITLWKN |
| 61 | TTPKDVFTYD | YATGSTYIFT | NIDYEVKDGY ENLTATYQTT VENATAQEVG TTDEDETFAG |
| 121 | GEPLDHHLDD | ALNETPDDAE | TESDSGHVMT SFASRDQLPE WTLHTYTLTA TDGAKTDTEY |
| 181 | ARRTLAYTVR | QELYTDHDAA | PVATDGLMLL TPEPLGETPL DLDCGVRVEA DETRTLDYTT |
| 241 | AKDRLLAREL | VEEGLKRSLW | DDYLVRGIDE VLSKEPVLTC DEFDLHERYD LSVEVGHSGR |
| 301 | AYLHINFRHR | FVPKLTLADI | DDDNIYPGLR VKTTYRPRRG HIVWGLRDEC ATDSLNTLGN |
| 361 | QSVVAYHRNN | QTPINTDLLD | AIEAADRRVV ETRRQGHGDD AVSFPQELLA VEPNTHQIKQ |
| 421 | FASDGFHQQA | RSKTRLSASR | CSEKAQAFAE RLDPVRLNGS TVEFSSEFFT GNNEQQLRLL |
| 481 | YENGESVLTF | RDGARGAHPD | ETFSKGIVNP PESFEVAVVL PEQQADTCKA QWDTMADLLN |
| 541 | QAGAPPTRSE | TVQYDAFSSP | ESISLNVAGA IDPSEVDAAF VVLPPDQEGF ADLASPTETY |
| 601 | DELKKALANM | GIYSQMAYFD | RFRDAKIFYT RNVALGLLAA AGGVAFTTEH AMPGDADMFI |
| 661 | GIDVSRSYPE | DGASGQINIA | ATATAVYKDG TILGHSSTRP QLGEKLQSTD VRDIMKNAIL |
| 721 | GYQQVTGESP | THIVIHRDGF | MNEDLDPATE FLNEQGVEYD IVEIRKQPQT RLLAVSDVQY |
| 781 | DTPVKSIAAI | NQNEPRATVA | TFGAPEYLAT RDGGGLPRPI QIERVAGETD IETLTRQVYL |
| 841 | LSQSHIQVHN | STARLPITTA | YADQASTHAT KGYLVQTGAF ESNVGFL |

Introduction of Materials into Cells:

The invention also includes compositions and methods for introduction of gene editing system components and/or donor nucleic acid molecules into cells. Introduction of a various molecules into cells may be done in a number of ways including by methods described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbour Laboratory Press, Cold Spring Harbor. N.Y. (1989), such as, calcium phosphate transfection, DEAE-dextran mediated transfection, transfection, microinjection, cationic lipid-mediated transfection, electroporation, transduction, scrape loading, ballistic introduction, nucleoporation, hydrodynamic shock, and infection.

The invention includes methods in which different components of nucleic acid cutting entities and/or donor nucleic acid molecules are introduced into cells by different means, as well as compositions of matter for performing such methods. For example, a lentiviral vector may be used to introduce nucleic acid encoding Cas9 operably linked to a suitable promoter and guide RNA may be introduced by transfection. Further, donor nucleic acid may be associated with the guide RNA. Also, Cas9 mRNA may be transcribed from a chromosomally integrated nucleic acid molecule, resulting in either constitutive or regulatable production of this protein.

In many instances, a single type of nucleic acid cutting entity molecule may be introduced into a cell but some nucleic acid cutting entity molecules may be expressed within the cell. One example of this is where two zinc finger-FokI fusions are used to generate a double-stranded break in intracellular nucleic acid. In some instance, only one of the zinc finger-FokI fusions may be introduced into the cell and the other zinc finger-FokI fusion may be produced intracellularly.

Transfection agents suitable for use with the invention include transfection agents that facilitate the introduction of RNA, DNA and proteins into cells. Exemplary transfection reagents include TurboFect Transfection Reagent (Thermo Fisher Scientific), Pro-Ject Reagent (Thermo Fisher Scientific), TRANSPASS™ P Protein Transfection Reagent (New England Biolabs), CHARIOT™ Protein Delivery Reagent (Active Motif), PROTEOJUICE™ Protein Transfection Reagent (EMD Millipore), 293fectin, LIPOFECTAMINE™ 2000, LIPOFECTAMINE™ 3000 (Thermo Fisher Scientific), LIPOFECTAMINE™ (Thermo Fisher Scientific), LIPOFECTIN™ (Thermo Fisher Scientific), DMRIE-C, CELLFECTIN™ (Thermo Fisher Scientific), OLIGOFECTAMINE™ (Thermo Fisher Scientific), LIPOFECTACE™, FUGENE™ (Roche, Basel, Switzerland), FUGENE™ HD (Roche), TRANSFECTAM™ (Transfectam, Promega, Madison, Wis.), TFX-10™ (Promega), TFX-20™ (Promega), TFX-50™ (Promega), TRANSFECTIN™ (BioRad, Hercules, Calif.), SILENTFECT™ (Bio-Rad), Effectene™ (Qiagen, Valencia, Calif.), DC-chol (Avanti Polar Lipids), GENEPORTER™ (Gene Therapy Systems, San Diego, Calif.), DHARMAFECT 1™ (Dharmacon, Lafayette, Colo.), DHARMAFECT 2™ (Dharmacon), DHARMAFECT 3™ (Dharmacon), DHARMAFECT 4™ (Dharmacon), ESCORT™ III (Sigma, St. Louis, Mo.), and ESCORT™ IV (Sigma Chemical Co.).

The invention further includes methods in which one molecule is introduced into a cell, followed by the introduction of another molecule into the cell. Thus, more than one nucleic acid cutting entity component may be introduced into a cell at the same time or at different times. As an example, the invention includes methods in which Cas9 is introduced into a cell while the cell is in contact with a transfection reagent designed to facilitate the introduction of proteins in to cells (e.g., TurboFect Transfection Reagent), followed by washing of the cells and then introduction of guide RNA while the cell is in contact with LIPOFECTAMINE™ 2000.

In some specific instances, Cas9-RNA complexes may be introduced into cells at one time point and donor nucleic acid molecules may be introduced at a different time point. It has been shown that gene editing efficiency increases when two gene editing reagents such as these are introduced into cells at separate time points. Further, Cas9-RNA complexes may be introduced first, followed by donor nucleic acid molecules being introduced later. Also, donor nucleic acid molecules may be introduced first, followed by Cas9-RNA complexes being introduced later. The time between introduction of the different gene editing reagents into cells may be between 1 minute and 600 minutes (e.g., 1 minute and 500 minutes, 1 minute and 400 minutes, 1 minute and 300 minutes, 1 minute and 200 minutes, 1 minute and 100 minutes, 1 minute and 50 minutes, 1 minute and 30 minutes, 1 minute and 20 minutes, 1 minute and 10 minutes, 5 minutes and 500 minutes, 5 minutes and 200 minutes, 5 minutes and 100 minutes, 5 minutes and 50 minutes, 5 minutes and 30 minutes, 10 minutes and 100 minutes, 10 minute and 200 minutes, 10 minutes and 50 minutes, 15 minutes and 100 minutes, etc.).

Conditions will normally be adjusted on, for example, a per cell type basis for a desired level of nucleic acid cutting entity component introduction into the cells. While enhanced conditions will vary, enhancement can be measure by detection of intracellular nucleic acid cutting activity. Thus, the invention includes compositions and methods for measurement of the intracellular introduction of nucleic acid cutting activity within cells.

With respect to CRISPRs, the invention also includes compositions and methods related to the formation and introduction of CRISPR complexes into cells.

A number of compositions and methods may be used to form CRISPR complexes. For example, cas9 mRNA and a guide RNA may be encapsulated in INVIVOFECTAMINE™ for, for example, later in vivo and in vitro delivery as follows. mRNA cas9 is mixed (e.g., at a concentration of at 0.6 mg/ml) with guide RNA. The resulting mRNA/gRNA solution may be used as is or after addition of a diluents and then mixed with an equal volume of INVIVOFECTAMINE™ and incubated at 50° C. for 30 min. The mixture is then dialyzed using a 50 kDa molecular weight curt off for 2 hours in 1×PBS, pH7.4. The resulting dialyzed sample containing the formulated mRNA/gRNA is diluted to the desire concentration and applied directly on cells in vitro or inject tail vein or intraperitoneal for in vivo delivery. The formulated mRNA/gRNA is stable and can be stored at 4° C.

For Cas9 mRNA transfection of cultured cells, such as 293 cells, 0.5 µg mRNA was added to 25 µl of Opti-MEM, followed by addition of 50-100 ng gRNA. Meanwhile, two µl of LIPOFECTAMINE™ 3000 or RNAiMax was diluted into 25 µl of Opti-MEM and then mixed with mRNA/gRNA sample. The mixture was incubated for 15 minutes prior to addition to the cells.

A CRISPR system activity may comprise expression of a reporter (e.g., green fluorescent protein, β-lactamase, luciferase, etc.) or nucleic acid cleavage activity. Using nucleic acid cleavage activity for purposes of illustration, total nucleic acid can be isolated from cells to be tested for CRISPR system activity and then analyzed for the amount of nucleic acid that has been cut at the target locus. If the cell is diploid and both alleles contain target loci, then the data will often reflect two cut sites per cell. CRISPR systems can be designed to cut multiple target sites (e.g., two, three four, five, etc.) in a haploid target cell genome. Such methods can be used to, in effect, "amplify" the data for enhancement of CRISPR system component introduction into cells (e.g., specific cell types). Conditions may be enhanced such that greater than 50% of the total target loci in cells exposed to CRISPR system components (e.g., one or more of the following: Cas9 protein, Cas9 mRNA, crRNA, tracrRNA, guide RNA, complexed Cas9/guide RNA, etc.) are cleaved. In many instances, conditions may be adjusted so that greater than 60% (e.g., greater than 70%, greater than 80%, greater than 85%, greater than 90%, greater than 95%, from about 50% to about 99%, from about 60% to about 99%, from about 65% to about 99%, from about 70% to about 99%, from about 75% to about 99%, from about 80% to about 99%, from about 85% to about 99%, from about 90% to about 99%, from about 95% to about 99%, etc.) of the total target loci are cleaved.

EXAMPLES

Example 1: Enhanced CRISPR/Cas9-Mediated Precise Genome Editing by Improved Design and Delivery of gRNA, Cas9 Nuclease, and Donor DNA Abstract While CRISPR-based gene knock out in mammalian cells has proven to be very efficient, precise insertion of genetic elements through homology directed repair (HDR) remains a rate-limiting step to seamless genome editing. Under the conditions described here, we achieved approximately 60% targeted integration efficiency with up to a six-nucleotide insertion in HEK293 cells. Finally, the use of a short double stranded (ds)DNA oligonucleotide with 3' overhangs allowed integration of a longer FLAG epitope tag along with a restriction site into multiple loci at rates of up to 50%.

These data suggest that after cleavage, the Cas9 complex dissociates from the cleavage site, or is dislodged sufficiently, allowing access to relatively short (~30 nt) 3' overhangs on either side of the break with comparable efficiency. This is likely due to 5' end resection via the DNA repair machinery. This model favors the design of donor DNAs with the insertion or SNP repair element as close to the cleavage site as possible and 3' protruding single strand homology arms of approximately 30 bases for larger donor molecules. For smaller single stranded donor molecules, 30 base arms 3' to the insertion/repair cassette and greater than 40 bases on the 5' end seems to be favored.

Introduction

The recent advances in CRISPR-mediated genome engineering enable researchers to efficiently introduce double-strand breaks (DSBs) in genomic DNA (Cho, S. W., Kim, S., Kim, J. M., Kim, J. S., 2013, *Targeted genome engineering in human cells with the Cas9 RNA-guided endonuclease, Nat. Biotechnol.* 31:230-232; Jiang, W., Bikard, D., Cox, D., Zhang, F., Marraffini, L. A., *RNA-guided editing of bacterial genomes using CRISPR-Cas systems, Nat. Biotechnol.* 31:233-239 (2013); Liang, X., Potter, J., Kumar, S., Zou, Y., Quintanilla, R., Sridharan, M., Carte, J., Chen, W., Roark, N., Ranganathan, S., Ravinder, N., Chesnut, J. D., *Rapid and highly efficient mammalian cell engineering via Cas9 protein transfection, J. Biotechnol.* 208:44-53 (2015); Mali, P., Yang, L., Esvelt, K. M., Aach, J., Guell, M., DiCarlo, J. E., Norville, J. E., Church, G. M., *RNA-guided human genome engineering via Cas9, Science* 339(6121):823-826 (2013); Wang, H., Yang, H., Shivalila, C. S., Dawlaty, M. M., Cheng, A. W., Zhang, F., Jaenisch, R., *One-step generation of mice carrying mutations in multiple genes by CRISPR/Cas-mediated genome engineering, Cell* 153:910-918 (2013)). The DSBs are then mostly repaired by either the non-homologous end joining (NHEJ) pathway or the homology-directed repair (HDR) pathway. In mammalian cells, the NHEJ pathway is predominant and error-prone, which results in disruptive insertions or deletions (indels) at targeted loci allowing for the efficient creation of gene knockouts. Alternatively, the cells may utilize sister chromatids or an exogenous DNA template to repair the DNA damage via HDR, but the efficiency is relatively low. For example, the use of a Cas9 nickase produced HDR frequencies of 6% in HEK293FT cells with a single-stranded DNA oligonucleotide (ssDNA) (Ran, F. A., Hsu, P. D., Lin, C. Y., Gootenberg, J. S., Konermann, S., Trevino, A. E., Scott, D. A., Inoue, A., Matoba, S., Zhang, Y., Zhang, F., *Double nicking by RNA-guided CRISPR Cas9 for enhanced genome editing specificity, Cell* 154(6):1380-1389 (2013)) or 5% in human embryonic stem cells (hESCs) with a long DNA donor template containing a puromycin selection cassette (Rong, Z., Zhu, S., Xu, Y., Fu, X., *Homologous recombination in human embryonic stem cells using CRISPR/Cas9 nickase and a long DNA donor template, Protein Cell* 5(4):258-260 (2014)). The synchronization of cells at M phase with nocodazole prior to nucleofection resulted in up to 38% and 1.6% HDR in HEK293T cells and hESCs respectively, which were higher than the controls of 26% and essentially ~0% in un-synchronized HEK293T cells and hESCs respectively (Lin, S., Staahl, B. T., Alla, R. K., Doudna, J. A., *Enhanced homology-directed human genome engineering by controlled timing of CRISPR/Cas9 delivery, Elife* 3:e04766 (2014)). The co-delivery of gRNA with a ssDNA donor into Cas9-expressing human pluripotent stem cells (hPSCs) generated homozygous knock-in clones at a rate of up to 10% (González, F., Zhu, Z., Shi, Z. D., Lelli, K., Verma, N., Li, Q. V., Huangfu, D., *An iCRISPR platform for rapid, multiplexable, and inducible genome editing in human pluripotent stem cells. Cell Stem Cell* 15(2):215-226 (2014)). The delivery of Cas9 ribonucleoproteins (RNPs) into primary T cells via electroporation caused up to 40% of cells to lose high-level cell-surface expression of CXCR4 and generated genomic knock-in modifications with up to 20% efficiency (Schumann, K., Lin, S., Boyer, E., Simeonov, D. R., Subramaniam, M., Gate, R. E., Haliburton, G. E., Ye, C. J., Bluestone, J. A., Doudna, J. A., Marson, A., *Generation of knock-in primary human T cells using Cas9 ribonucleoproteins, Proc. Natl. Acad. Sci. USA* 112(33): 10437-10442 (2015)). Recently, several attempts have been made to improve HDR efficiency by biochemically altering the HDR or NHEJ pathways. For example, the treatment of cells with Scr7, a DNA ligase IV inhibitor, resulted in up to 19-fold increase in HDR efficiency (Maruyama, T., Dougan, S. K., Truttmann, M. C., Bilate, A. M., Ingram, J. R., Ploegh, H. L., *Increasing the efficiency of precise genome editing with CRISPR-Cas9 by inhibition of nonhomologous end joining, Nat. Biotechnol.* 33(5):538-420 (2015)). The simultaneous suppression of both KU70 and DNA ligase IV with siRNAs improved the efficiency of HDR 4-5 fold (Chu, V. T., Weber, T., Wefers, B., Wurst, W., Sander, S., Rajewsky, K., Kuhn, R., *Nat. Biotechnol.* 33(5):543-548 (2015)). The HDR enhancer RS-1 increased the knock-in efficiency in rabbit embryos both in vitro and in vivo by 2-5 fold (Song, J., Yang, D., Xu, J., Zhu, T., Chen, Y. E., Zhang, J., *RS-1 enhances CRISPR/Cas9-and TALEN-mediated knock-in efficiency, Nat. Commun.* 7:10548. doi: 10.1038/ncomms10548 (2016)). Most recently, the use of asymmetric ssDNA donors of optimal length increased the rate of HDR in human cells up to 60% for a single nucleotide substitution (Richardson, C. D., Ray, G. J., DeWitt, M. A., Curie, G. L., Corn, J. E., 2016. *Enhancing homology-directed genome editing by catalytically active and inactive CRISPR-Cas9 using asymmetric donor DNA, Nat. Biotechnol.* 34:339-344 (2016)). In this study, we examined alternative approaches to improve HDR without impairment of other cellular DNA repair machinery. By optimizing the design and delivery of gRNA, Cas9 nuclease and donor DNA, we achieved approximately 40% precise genome editing efficiencies in multiple genomic loci of various cell lines. The vicinity of the DSB to target locus, asymmetric sense or antisense ssDNA, and electroporation conditions determined the overall integration efficiency. Furthermore, the alternate design of a short dsDNA oligonucleotide with 3' overhangs improved the insertion efficiency of epitope tags into the genome.

Materials and Methods
Materials

GENEART™ PLATINUM™ Cas9 Nuclease, GENEART™ CRISPR gRNA Design Tool, GENEART™ Precision gRNA Synthesis Kit, GRIPTITE™ HEK293 cells, DMEM medium, Fetal Bovine Serum (FBS), TRYPLE™ Express Enzyme, JUMP-IN™ GRIPTITE™ HEK293 Kit, Lentivirus expressing Cas9 nuclease and blasticidin marker, 2% E-GEL® EX Agarose Gels, VIRAPOWER® kit, TranscriptAid T7 High Yield Transcription Kit, MEGACLEAR™ Transcription Clean-Up Kit, ZERO BLUNT® TOPO® PCR Cloning Kit, PURELINK® Pro Quick96 Plasmid Purification Kit, QUBIT® RNA BR Assay Kit, NEON® Transfection System 10 µL Kit, and Phusion Flash High-Fidelity PCR Master Mix were from Thermo Fisher Scientific. Monoclonal Cas9 antibody was purchased from Diagenode. The DNA oligonucleotides used for gRNA synthesis or donors were from Thermo Fisher Scientific (Table 4).

Synthesis of gRNA

DNA oligonucleotides used for gRNA synthesis were designed by GeneArt™ CRISPR gRNA Design Tool. The gRNAs were then synthesized using the GeneArt™ Precision gRNA Synthesis Kit. The concentration of gRNA was determined by QUBIT® RNA BR Assay Kit.

Genomic Cleavage and Detection (GCD) Assay

The genomic cleavage efficiency was measured by GENEART® Genomic Cleavage Detection kit according to manufacturer's instructions. The primer sequences for PCR amplification of each genomic locus are described in Table 4. Cells were analyzed at 48 to 72 hours post transfection. The cleavage efficiencies were calculated based on the relative agarose gel band intensity, which were quantified using an ALPHAIMAGER® gel documentation system running ALPHAVIEW®, Version 3.4.0.0. ProteinSimple (San Jose, Calif., USA).

Generation of Stable Cell Lines

The JUMP-IN™ system was used to prepare GRIPTITE™ HEK293 stable cell expressing EmGFP (Thermo Fisher Scientific). The gene sequence of EmGFP is described in Table 5. To create a disrupted EmGFP mutant stable cell line, a gRNA targeting the 5'-ctcgtgaccaccttcacctacgg-3' (SEQ ID NO: 125) sequence in EmGFP gene was synthesized. The resulting gRNA (300 ng) was incubated with 1.5 µg of GENEART® PLATINUM™ Cas9 nuclease and used to transfect wild type EmGFP cells via electroporation. The single cell clonal isolation was carried out by limiting dilution. The EmGFP loci from non-glowing cells were amplified by PCR using a forward primer 5'-atggtgag-caagggcgaggagctg-3' (SEQ ID NO: 126) and a reverse primer 5'-gtcctccttgaagtcgatgccc-3' (SEQ ID NO: 127) and the resulting PCR products were subjected to TOPO cloning and sequencing. From these clones, a disrupted EmGFP stable cell line containing a deletion of 5'-CACCTT-3' (SEQ ID NO: 25) was identified (Table 5). In the homologous recombination assay, the gain of EmGFP function was determined by flow cytometric analysis.

To generate a HEK293FT stable cell line expressing eBFP, an eBFP ORF was synthesized by GENEART® custom DNA synthesis (Thermo Fisher Scientific) and then cloned into pDONAR221 vector. Using GATEWAY® recombination technology (Thermo Fisher Scientific), the eBFP ORF was transferred to pLenti6.2-DEST Gateway Vector and then verified by sequencing. Lentivirus was generated using VIRAPOWER® kit as described in the manual. To generate stable cell line, HEK293FT cells were transduced with 0.1 MOI of Lentivirus expressing eBFP. Three days post transduction cells were selected on 5 µg/mL Blasticidine antibiotics for 2 weeks. Cells expressing eBFP were then collected and diluted to 0.8 cells/mL in complete medium and plated into 96 well plates for single cell clone. After 2 weeks clones were isolated and verified for eBFP expression by flow cytometer. In a reporter assay using a stable eBFP-expressing HEK293 cell line, the substitution of C to T in eBFP gene converts His67 to Tyr67, generating a GFP variant (Table 5).

Homologous Recombination Assays

To create homologous recombination (HR) assays, a series of gRNAs flanking the insertion site within the EmGFP gene were designed and synthesized (Table 4). Each individual gRNA was combined with GENEART™ PLATINUM™ Cas9 Nuclease to form the Cas9 protein/gRNA ribonucleoprotein complexes (Cas9 RNPs). The Cas9 RNPs were then used to transfect cells via NEON® electroporation. The genomic cleavage efficiency was then evaluated using the GENEART® Genomic Cleavage Detection kit at 48 hours post transfection. The gRNAs with highest editing efficiencies and also in close proximity to the insertion site were selected for the subsequent HR assays. For donor design of a single-stranded oligonucleotide, typically the mutation site was positioned at the center flanked by 30 to 50 nucleotides on each side. For asymmetric donor design, 30 nucleotides were placed on either the left or right arm and then 50 or 67 nucleotides on the right or left arm respectively, in both PAM and non-PAM strands. For design of a dsDNA oligonucleotide with single-stranded overhangs, the insertion element was overlapped in the center flanked by various lengths of ssDNA oligonucleotide on each side. By annealing two single-stranded oligonucleotides at 95° C. for 3 minutes, dsDNA donor molecules with either a 5' protrusion or a 3' protrusion were generated. To measure homologous recombination efficiency, the donor DNA was either co-transfected with Cas9 RNPs or delivered sequentially into cells via electroporation. At 48 hours post transfection, the gain of EmGFP function in reporter cell lines was determined by flow cytometric analysis with an Attune® NxT Acoustic Focusing Cytometer (Thermo Fisher Scientific). Alternatively, the genomic loci were PCR-amplified using the corresponding primers and then subjected to GENEART® Genomic Cleavage Detection assay or restriction digestion. The resulting PCR products were also subjected to TOPO cloning. Typically, 96 colonies were randomly picked for sequencing. The sequencing data were analyzed using VECTOR NTI ADVANCE® 11.5 software (Thermo Fisher Scientific).

Electroporation

Typically, $1\times10^5$ GRIPTITE™ HEK293 cells were used per electroporation using Neon® Transfection System 10 µL Kit (Thermo Fisher Scientific). To optimize the electroporation conditions, the preprogrammed NEON® 24-well optimization protocol was tested according to the manufacturer's instructions. To make up a master mix of 24 reactions, 8 µl of 3 mg/ml GENEART™ Platinum™ Cas9 Nuclease was added to 240 µl of Resuspension Buffer R provided in the kit, followed by addition of 4.8 µg of gRNA. Upon mixing, the sample was incubated at room temperature for 10 minutes to form Cas9 RNP complexes. Meanwhile, $2.4\times10^6$ cells were transferred to a sterile Eppendorf tube and centrifuged at 1000×g for 5 minutes. The supernatant was carefully aspirated and the cell pellet was washed once with 1 ml of DPBS without Ca2+ and Mg2+. Upon centrifugation, the supernatant was carefully aspirated. Resuspension Buffer R containing the Cas9 RNPs was used to resuspend the cell pellets. A 10 µl cell suspension was used for each of the preprogrammed NEON® 24-well optimization protocols. The electroporated cells were transferred to 24 or 48-well plates containing 0.5 ml of the corresponding growth medium and then incubated for 48 hours in a 5% CO2 incubator. The cells were washed with DPBS and then lysed in lysis buffer, followed by genomic cleavage and detection assay as described above. Upon optimization of electroporation conditions, higher doses of Cas9 protein (1.5 to 2 µg) and gRNA (300 to 500 ng) were used to improve the genome editing efficiency.

For each homologous recombination assay, 1.5 µg of Cas9 protein and 360 ng of gRNA were added to Resuspension Buffer R to a final volume of 7 µl, but limiting the total volume of Cas9 protein plus gRNA to less than 1 µl. The gRNA could be diluted in Buffer R if the concentration was too high. Upon mixing, the sample was incubated at room temperature for 5 to 10 minutes to form Cas9 RNPs. Meanwhile, GRIPTITE™ HEK293 cells expressing either eBFP or disrupted EmGFP were detached from culture flask with TRYPLE™ Express Enzyme and then counted. Aliquots of $1\times106$ cells were washed once with DPBS without $Ca^{2+}$ and $Mg^{2+}$ and the cell pellets were resuspended in 50 µl of Resuspension Buffer R. A 5 µl aliquot of cell suspension was mixed with 7 µl of Cas9 RNPs. For sequential delivery of Cas9 RNPs and DNA donor, 10 µl of cell suspension containing Cas9 RNP was applied to electroporation with voltage set at 1150V, pulse width set at 20 ms, and the number of pulses set at 2, respectively. The electroporated cells were transferred to 300 µl of Resuspension Buffer R or DPBS. Upon centrifugation at 2000×g for 5 minutes, the supernatant was carefully aspirated and the cell pellet was resuspended in Buffer R to a final volume of 11 µl, followed by addition of 1 µl of 10 pmol/µl or 0.3 µg/µl ssDNA donor. Alternatively, 1 µl of 10 pmol/µl short dsDNA donor with and without single-stranded overhangs was added. An aliquot of 10 µl cell suspension containing donor DNA was used for electroporation using the same instrument settings. Upon electroporation, the cells were transferred to a 48-well plate containing 0.5 ml culture media. For sequential delivery, the viability of HEK293 cells was around 50%. For co-transfection of Cas9 RNPs with donor DNA, 0.5 µl of 20 pmol/µl or 0.6 µg/µl ssDNA donor was directly added to the 12 µl of cell suspension containing Cas9 RNPs. Alternatively, 0.5 µl of 20 pmol/µl short dsDNA donor with and without single-stranded overhangs was added. An aliquot of 10 µl of cell suspension containing Cas9 RNPs and donor DNA was used for electroporation. Samples without either gRNA or donor DNA served as controls. In addition to ssDNA donor, a 400 bp double-stranded DNA fragment was also tested, which was amplified from the wild type EmGFP gene using a pair of forward 5'-atggtgagcaagggcgaggagctg-3' (SEQ ID NO: 126) and reverse 5'-gtcctccttgaagtcgatgccc-3' (SEQ ID NO: 127) primers. For each assay, 300 to 500 ng dsDNA was used. At 48 hours post transfection, the cells were analyzed by flow cytometry. Alternatively, the genomic loci were PCR-amplified with the corresponding primers. The resulting PCR fragments were analyzed using the GENEART® Genomic Cleavage Detection assay or restriction digestion. The PCR fragments were also subjected to cloning and sequencing.

Optimization of Delivery of Cas9 RNP and Donor DNA

To measure HDR efficiency, we engineered a GRIPTITE™ HEK293 stable cell line and a HEK293FT stable cell line expressing EmGFP and eBFP respectively (FIG. 13). Cas9 protein/gRNA complexes (Cas9 RNPs) were subsequently used to target the fluorogenic region of EmGFP to generate a disrupted EmGFP stable cell line containing a deletion of six nucleotides (FIG. 13A). The deletion of Thr63 and Phe64 residues resulted in ablation of EmGFP activity, which could be restored by introducing an exogenous wild type donor DNA molecule. When the disrupted EmGFP stable cells were transfected with Cas9 RNP and ssDNA donor, a significant number of EmGFP-positive cells were observed. Conversely, in the absence of ssDNA donor (Cas9 RNP alone) or gRNA (Cas9/donor), almost no EmGFP-expressing cells were detected. For measurement of homologous recombination activity using the eBFP-expressing HEK293 stable cells, a single nucleotide transition of "C" to "T" converts a His to a Tyr at residue 66, resulting in the conversion of eBFP into closely related GFP (FIG. 13B). When eBFP-expressing cells were transfected with Cas9 RNP plus ssDNA donor, a significant number of GFP-positive cells were detected. As expected, predominantly eBFP-positive cells, but very few GFP-positive cells were detected in the absence of gRNA. A time-lapse video for HDR was recorded every 2 hours for a total of 72 hours (data not shown).

After validating our HDR assay systems, we optimized the delivery of Cas9 RNP and donor DNA as described. As shown in Table 10, a majority of NEON® optimization programs worked well for delivery of Cas9 RNP into HEK293 cells. A program with the voltage set at 1150V, pulse width set at 20 ms, and 2 pulses was used for the subsequent study. Initially, we co-delivered Cas9 RNP with a 97 base single-stranded PAM or non-PAM oligonucleotide into HEK293 cells. The PAM ssDNA oligonucleotide donor was defined as the strand containing the PAM (NGG) sequence (FIG. 7A). Based on flow cytometric analysis, we observed approximately 5% and 6% EmGFP-positive cells using the PAM or non-PAM ssDNA oligonucleotides, respectively (FIG. 7B). Since the program used for Cas9 RNP delivery might not apply to the delivery of donor DNA, we tested the sequential delivery of Cas9 RNP and donor DNA. The Cas9 RNP was first delivered into HEK293 cells via electroporation. The electroporated cells were then washed once with Resuspension Buffer R. The cell pellets were resuspended in Buffer R containing ssDNA or dsDNA donor. The cell suspension was then electroporated using the NEON® 24-well optimization protocol (see Table 3).

TABLE 3

Electroporation Protocols

| Protocol | | | | | | | | |
|---|---|---|---|---|---|---|---|---|
| | Pst | 2 | 3 | 4 | 5 | 6 | 7 | 8 |
| Pulse Voltage | 1150 | 1400 | 1500 | 1600 | 1700 | 1100 | 1200 | 1300 |
| Pulse Width | 20 | 20 | 20 | 20 | 20 | 30 | 30 | 30 |
| # of Pulse | 2 | 1 | 1 | 1 | 1 | 1 | 1 | 1 |

| Protocol | | | | | | | |
|---|---|---|---|---|---|---|---|
| 9 | 10 | 11 | 12 | 13 | 14 | 15 | 16 |
| Pulse Voltage 1400 | 1000 | 1100 | 1200 | 1100 | 1200 | 1300 | 1400 |
| Pulse Width 30 | 40 | 40 | 40 | 20 | 20 | 20 | 20 |
| # of Pulse 1 | 1 | 1 | 1 | 2 | 2 | 2 | 2 |

| Protocol | | | | | | | |
|---|---|---|---|---|---|---|---|
| 17 | 18 | 19 | 20 | 21 | 22 | 23 | 24 |
| Pulse Voltage 850 | 950 | 1050 | 1150 | 1300 | 1400 | 1500 | 1600 |
| Pulse Width 30 | 30 | 30 | 30 | 10 | 10 | 10 | 10 |
| # of Pulse 2 | 2 | 2 | 2 | 3 | 3 | 3 | 3 |

TABLE 4

DNA Oligonucleotides

| Oligonucleotides for six nucleotide insertion in disrupted EmGFP stable cell line (FIGS. 7, 8, and 9) | | SEQ ID |
|---|---|---|
| Non-PAM oligo | p-Oftctgcaccaccggcaagctgcccgtgccctggcccaccctcgtgaccaccttcacct acggcgtgcagtgcttcgcccgctaccccgaccacFZg | 35 |
| PAM oligo (97-mer) | p-OFTGTGGTCGGGGTAGCGGGCGAAGCACTGCACGCCGT AGGTGAAGGTGGTCACGAGGGTGGGCCAGGGCACGGGC AGCTTGCCGGTGGTGCAGFZG | 36 |
| 97 | caTGTGGTCGGGGTAGCGGGCGAAGCACTGCACGCCGT AGGTGAAGGTGGTCACGAGGGTGGGCCAGGGCACGGG CAGCTTGCCGGTGGTGCAGatG | 37 |
| PS79 | p-OFTGTGGTCGGGGTAGCGGGCGAAGCACTGCACGCCG TAGGTGAAGGTGGTCACGAGGGTGGGCCAGGGCACGGG CFEC | 38 |
| 79 | CATGTGGTCGGGGTAGCGGGCGAAGCACTGCACGCCG TAGGTGAAGGTGGTCACGAGGGTGGGCCAGGGCACGG GCAGC | 39 |
| PS60 | p-OEGGGTAGCGGGCGAAGCACTGCACGCCGTAGGTGAA GGTGGTCACGAGGGTGGGCCFEG | 40 |
| 60 | CGGGGTAGCGGGCGAAGCACTGCACGCCGTAGGTGAA GGTGGTCACGAGGGTGGGCCAGG | 41 |
| PS40 | p-EECGAAGCACTGCACGCCGTAGGTGAAGGTGGTCAC GFEG | 42 |
| 40 | GGCGAAGCACTGCACGCCGTAGGTGAAGGTGGTCACG AGG | 43 |

| Oligonucleotides for single point mutation in HEK293 cells expressing BFP (FIGS. 7D and 8B) | | SEQ ID |
|---|---|---|
| 100 | ACCGGCAAGCTGCCCGTGCCCTGGCCCACCCTCG TGACCACCCTGACCTACGGCGTGCAGTGCTTCAG CCGCTACCCCGACCACATGAAGCAGCACGACT | 44 |
| PS100 | P-FOCGGCAAGCTGCCCGTGCCCTGGCCCACCCTC TGACCACCCTGACCTACGGCGTGCAGTGCTTCAG CCGCTACCCCGACCACATGAAGCAGCACGFOT | 45 |

TABLE 4-continued

| | DNA Oligonucleotides | |
|---|---|---|
| 90 | GCAAGCTGCCCGTGCCCTGGCCCACCCTCGTGAC CACCCTGACCTACGGCGTGCAGTGCTTCAGCCGC TACCCCGACCACATGAAGCAGC | 46 |
| PS90 | P-EOAAGCTGCCCGTGCCCTGGCCCACCCTCGTGA CCACCCTGACCTACGGCGTGCAGTGCTTCAGCCG CTACCCCGACCACATGAAGCFEC | 47 |
| 80 | GCTGCCCGTGCCCTGGCCCACCCTCGTGACCACCC TGACCTACGGCGTGCAGTGCTTCAGCCGCTACCCC GACCACATGA | 48 |
| PS80 | P-EOTGCCCGTGCCCTGGCCCACCCTCGTGACCACC CTGACCTACGGCGTGCAGTGCTTCAGCCGCTACCC CGACCACAZEA | 49 |
| 70 | CCCGTGCCCTGGCCCACCCTCGTGACCACCCTGACC TACGGCGTGCAGTGCTTCAGCCGCTACCCCGACC | 50 |
| PS70 | P-OOCGTGCCCTGGCCCACCCTCGTGACCACCCTGA CCTACGGCGTGCAGTGCTTCAGCCGCTACCCCGFOC | 51 |
| 60 | GCCCTGGCCCACCCTCGTGACCACCCTGACCTACGG CGTGCAGTGCTTCAGCCGCTACCC | 52 |
| PS60 | P-EOCCTGGCCCACCCTCGTGACCACCCTGACCTAC GGCGTGCAGTGCTTCAGCCGCTAOOC | 53 |
| 50 | CCCACCCTCGTGACCACCCTGACCTACGGCGTGCA GTGCTTCAGCCGCTA | 54 |
| P550 | P-OOCACCCTCGTGACCACCCTGACCTACGGCGTGC AGTGCTTCAGCCGOZA | 55 |

| | Oligonucleotides for single point mutation in iPSCs | SEQ ID |
|---|---|---|
| USP12 | GCGTATCAATGGATACTTACATTGACTAATCCAAA CTAGTGCTCATTGACCGGAAACTGTTCTGGACCAA TCTCTTTCTC | 56 |
| MDC1 | GCAATCCAGTGAATCCTTGAGGTGTAACGTGGAGC CAGTAAGGCGGCTACATATCTTTAGTGGTGCCCAT GGACCAGAAAAAG | 57 |
| CREBBP | CTGCACGGGGCTGCTGGCGCTCACATTTCCTATTC CTGGATTGATACTAGAGCCGCTGCCTCCTCGTAGA AGCTCCGACAG | 58 |
| HPRT | p-OZGACCTTGCCTTCATGTGATTCAGCCCCAGTCC ATTACCCTGTGTAGGACTGAGAAATGCAAGACTCT GGCTAGAGTTCCTTCTTCCATCTCCCZZC | 59 |
| HPRT (PAM mutation) | p-OZGACCTTGCCTTCATGTGATTCAGCCCCAGTCC ATTACaCTGTGTAGGACTGAGAAATGCAAGACTCT GGCTAGAGTTCCTTCTTCCATCTCCCZZC | 60 |

| | Asymmetric ssDNA donors (sense top strand, antisense bottom strand) | SEQ ID |
|---|---|---|
| GFP_PAM67-30 | p-Ozgaagttcatctgcaccaccggcaagctgcccgtgccctggcccacc ctcgtgaccaccttcacctacggcgtgcagtgcttcgcccgctaccOOg | 61 |
| GFP_non-PAM67-30 | p-OEGGGTAGCGGGCGAAGCACTGCACGCCG TAGGTGAAGGTGGTCACGAGGGTGGGCCAG GGCACGGGCAGCTTGCCGGTGGTGCAGATG AACTTOFG | 62 |
| GFP_PAM30-67 | p-Oogtgccctggcccaccctcgtgaccaccttcacctacggcgtgcag tgcttcgcccgctaccccgaccacatgaagcagcacgacttcttcaaEZc | 63 |
| GFP_nonPAM30-67 | p-EFCTTGAAGAAGTCGTGCTGCTTCATGTGG TCGGGGTAGCGGGCGAAGCACTGCACGCCGT AGGTGAAGGTGGTCACGAGGGTGGGCCAGG GCAOEG | 64 |
| GFP_PAM51-30 | p-Ooaccggcaagctgcccgtgccctggcccaccctcgtgaccacctt cacctacggcgtgcagtgcttcgcccgctaccOOg | 65 |
| GFP_non-PAM51-30 | p-OEGGGTAGCGGGCGAAGCACTGCACGCCG TAGGTGAAGGTGGTCACGAGGGTGGGCCAG GGCACGGGCAGCTTGCCGGZEG | 66 |
| GFP_PAM30-51 | p-Oogtgccctggcccaccctcgtgaccaccttcacctacggcgtgcag tgcttcgcccgctaccccgaccacatgaagcFEc | 67 |
| GFP_non-PAM30-51 | p-EOTGCTTCATGTGGTCGGGGTAGCGGGCGA AGCACTGCACGCCGTAGGTGAAGGTGGTCAC GAGGGTGGGCCAGGGCAOEG | 68 |
| GFP_PAM48-50 | p-Ooaccggcaagctgcccgtgccctggcccaccctcgtgaccaccttc acctacggcgtgcagtgcttcgcccgctaccccgaccacatgaagcagOFc | 69 |
| GFP_non-PAM48-50 | p-EZGCTGCTTCATGTGGTCGGGGTAGCGGGCG AAGCACTGCACGCCGTAGGTGAAGGTGG CAC GAGGGTGGGCCAGGGCACGGGCAGCTTGCCGG ZEG | 70 |
| GFP_PAM40-40 | p-Ofagctgcccgtgccctggcccaccctcgtgaccaccttcacctacgg cgtgcagtgcttcgcccgctaccccgaccacFZg | 71 |
| GFP_non-PAM40-40 | p-OFTGTGGTCGGGGTAGCGGGCGAAGCACTGC ACGCCGTAGGTGAAGGTGGTCACGAGGGTGGG CCAGGGCACGGGCAGCZZG | 72 |

TABLE 4-continued

DNA Oligonucleotides

Note: the PAM ssDNA oligonucleotide is defined as the gRNA targeting strand containing the NGG PAM sequence. — 73

| Oligonucleotides for insertion of Flag epitope tag plus EcoRI site into BFP locus | | SEQ ID |
|---|---|---|
| BFPins01 (ssDNA) | p-EZgccctggcccaccctcgtgaccaccctgaccGACTACAAA GACGATGACGACAAGAATTCTtacggcgtgcagtgcttc agccgctaccccgacOFc | 74 |
| BFPinsBF (blunt) | p-EFCTACAAAGACGATGACGACAAGAATTOZt | 75 |
| BFPinsBR (blunt) | p-FFGAATTCTTGTCGTCATCGTCTTTGTAEZC | 76 |
| BFP6nt5OF | p-OZgaccGACTACAAAGACGATGACGACAAGA ATTOZt | 77 |
| BFP6nt5OR | p-OECCGTAAGAATTCTTGTCGTCATCGTCTTT GTAEZC | 78 |
| BFP6nt3OF | p-EFCTACAAAGACGATGACGACAAGAATTCT tacgEOg | 79 |
| BFP6nt3OR | p-FFGAATTCTTGTCGTCATCGTCTTTGTAGTC GGTOFG | 80 |
| BFP15nt5OF | p-EZgaccaccctgaccGACTACAAAGACGATGACGA CAAGAATTOZt | 81 |
| BFP15nt5OR | p-EOACTGCACGCCGTAAGAATTCTTGTCGTCA TCGTCTTTGTAEZC | 82 |
| BFP15nt3OF | p-EFCTACAAAGACGATGACGACAAGAATTCTta cggcgtgcagZEc | 83 |
| BFP15nt3OR | p-FFGAATTCTTGTCGTCATCGTCTTTGTAGTCGG TCAGGGTGGTOFC | 84 |
| BFP30nt5OF | p-EZgccctggcccaccctcgtgaccaccctgaccGACTACAAAG ACGATGACGACAAGAATTOZt | 85 |
| BFP30nt5OR | p-EZGGTCGGGGTAGCGGCTGAAGCACTGCA CGCCGTAAGAATTCTTGTCGTCATCGTCTTT GTAEZC | 86 |
| BFP30nt3OF | p-EFCTACAAAGACGATGACGACAAGAATTCT tacggcgtgcagtgcttcagccgctaccccgacOFc | 87 |
| BFP30nt3OR | p-FFGAATTCTTGTCGTCATCGTCTTTGTAGTCGG TCAGGGTGGTCACGAGGGTGGGCCAGGGOFC | 88 |
| BFP24nt3OF | p-EFCTACAAAGACGATGACGACAAGAATTCT tacggcgtgcagtgcttcagccgctacOOc | 89 |
| BFP24nt3OR | p-FFGAATTCTTGTCGTCATCGTCTTTGTAGTCGG TCAGGGTGGTCACGAGGGTGGGOOA | 90 |
| BFP30nt3OFn | p-GACTACAAAGACGATGACGACAAGAATTCTT ACGGCGTGCAGTGCTTCAGCCGCTACCCCGAC CAC | 91 |
| BFP30nt3ORn | p-AAGAATTCTTGTCGTCATCGTCTTTGTAGTC GGTCAGGGTGGTCACGAGGGTGGGCCAGGGC AC | 92 |
| BFP36nt3OR | P-FFGAATTCTTGTCGTCATCGTCTTTGTAGTCG GTCAGGGTGGTCACGAGGGTGGGCCAGGGCAC EEG | 93 |
| BFP36nt3OF | p-efCTACAAAGACGATGACGACAAGAATTCT tacggcgtgcagtgcttcagccgctaccccgacofc | 94 |
| BFP45nt3OF | p-EFCTACAAAGACGATGACGACAAGAATTCTTA CGGCGTGCAGTGCTTCAGCCGCTACC CCGACCA CatgaagcagOFc | 95 |
| BFP45nt3OR | p-FFGAATTCTTGTCGTCATCGTCTTTGTAGTCGGT CAGGGTGGTCACGAGGGTGGGCCAG GGCACGG GCAGCTTGCOEG | 96 |

| Oligonucleotides for insertion of Flag epitope tag plus EcoRI site into +5 position in EmGFP gene | | SEQ ID |
|---|---|---|
| uGFPssT6_Flag | p-EOccgtgccctggcccaccctcgtgaccacctGACTACAAA GACGATGACGACAAGAATTCTacggcgtgcagtgctt cgcccgctaccccEFc | 97 |
| uGFP32nt5OT6f | p-EOccgtgccctggcccaccctcgtgaccacctGACTACAAA GACGATGACGACAAGAATTOZa | 98 |
| uGFP32nt5OT6r | p-EZCGGGGTAGCGGGCGAAGCACTGCACGCC GTAGAATTCTTGTCGTCATCGTCTTTGTAEZC | 99 |
| uGFP32nt3OT6f | p-FEAATTCTTGTCGTCATCGTCTTTGTAGTCAG GTGGTCACGAGGGTGGGCCAGGGCACGEEC | 100 |
| uGFP32nt3OT6r | p-EFCTACAAAGACGATGACGACAAGAATTCT acggcgtgcagtgcttcgcccgctaccccEFc | 101 |

Note: Sense strand is defined as the gRNA targeting strand with NGG PAM site.
p: 5'-phosphate; F: Phosphorothioate-A; O: Phosphorothioate-C; E: Phosphorothioate-G; Z: Phosphorothioate-T TABLE 4-continued DNA Oligonucleotides Primers for amplification of genomic loci

| Locus | gRNA Target | SEQ ID |
|---|---|---|
| BFP | CTCGTGACCACCCTGACCCACGG | 102 |
| GFP (−39) | CTGAAGTTCATCTGCACCACCGG | 103 |
| GFP (−34) | GGGCACGGGCAGCTTGCCGGTGG | 104 |
| GFP (−31) | CCAGGGCACGGGCAGCTTGCCGG | 105 |
| GFP (−20) | GGCAAGCTGCCCGTGCCCTGG | 106 |
| GFP (−19) | CACGAGGGTGGGCCAGGGCACGG | 107 |
| GFP (−14) | GGTGGTCACGAGGGTGGGCCAGG | 108 |
| GFP (−7) | GCCGTAGGTGGTCACGAGGGTGG | 109 |
| GFP (−3) | GCACGCCGTAGGTGGTCACGAGG | 110 |
| GFP (+3) | CCCACCCTCGTGACCACCTACGG | 111 |
| GFP (+5) | GAAGCACTGCACGCCGTAGGTGG | 112 |
| GFP (+8) | GGCGAAGCACTGCACGCCGTAGG | 113 |
| GFP (+21) | CTTCATGTGGTCGGGGTAGCGGG | 114 |
| GFP (+30) | GTCGTGCTGCTTCATGTGGTCGG | 115 |
| GFP (+34) | AGAAGTCGTGCTGCTTCATGTGG | 116 |
| HPRT | GCATTTCTCAGTCCTAAACAGGG | 117 |
| CREEP | AGCGGCTCTAGTATCAACCC | 118 |
| MDC1 | AAGATATGTAGCCGCCCTAC | 119 |
| USP12 | CCGGTCAATGAGCACTATTT | 120 |

TABLE 5

EmGFP and BFP sequences.

(A) Wild type EmGFP sequence (SEQ ID No: 121)
atggtgagcaagggcgaggagctgttcaccggggtggtgcccatc
ctggtcgagctggacggcgacgtaaacggccacaagttcagcgtt
gtccggcgagggcgagggcgatgccacctacggcaagctgaccct
gaagttcatctgcaccaccggcaagctgcccgtgccctggcccac cctcgtgaccaccttcacctacggcgtgcagtgcttcgcccgctac cccgaccacatgaagcagcacgacttcttcaagtccgccatgccc
gaaggctacgtccaggagcgcaccatcttcttcaaggacgacgg
caactacaagacccgcgccgaggtgaagttcgagggcgacaccct
ggtgaaccgcatcgagctgaagggcatcgacttcaaggaggacgg
caacatcctggggcacaagctggagtacaactacaacagccacaa
ggtctatatcatgccgccgacaagcagaagaacggcatcaaggtgaa
cttcaagacccgccacaacatcgaggacggcagcgtgcagctcgc
cgaccactaccagcagaacaccccatcggcgacggccccgtgctg
ctgcccgacaaccactacctgagcacccagtccgccctgagcaaag
accccaacgagaagcgcgatcacatggtcctgctggagttcgtgac
cgccgccgggatcactctcggcatggacgagctgtacaagtaa (B) A disrupted EmGFP sequence (SEQ ID No: 122)
atggtgagcaagggcgaggagctgttcaccggggtggtgcccatcct
ggtcgagctggacggcgacgtaaacggccacaagttcagcgtgtccg
gcgagggcgagggcgatgccacctacggcaagctgaccctgaagttc
atctgcaccaccggcaagctgcccgtgccctggcccac cctcgtgaccaccttcacctacggcgtgcagtgcttcgcccgctacc ccgaccacatgaagcagcacgacttcttcaagtccgccatgcccgaag
gctacgtccaggagcgcaccatcttcttcaaggacgacggcaactaca
agacccgcgccgaggtgaagttcgagggcgacaccctggtgaaccgca
tcgagctgaa<u>gggcatcgacttcaaggaggacgg</u>caacatcctgggc
acaagctggagtacaactacaacagccacaaggtctatatcatggccg
acaagcagaagaacggcatcaaggtgaacttcaagacccgccacaaca
tcgaggacggcagcgtgcagctcgccgaccactaccagcagaacaccc
ccatcggcgacggccccgtgctgctgcccgacaaccactacctgagca
cccagtccgccctgagcaaagaccccaacgagaagcgcgatcacatgg
tcctgctggagttcgtgaccgccgccgggatcactctcggcatggacg
agctgtacaagtaa
Note: In a disrupted EmGFP sequence, a sequence
of "cacctt" (SEQ ID NO: 25) was deleted.
Underlined sequences were used for amplification
of EmGFP locus and for preparation of dsDNA donor.

(C) Wild type BFP sequence (SEQ ID No: 123)
atggtgagcaagggcgaggagctgttcaccggggtggtgcccatcctg TABLE 5-continued EmGFP and BFP sequences.

gtcgagctggacggcgacgtaaacggccacaagttcagcgtgtccggc
gagggcgagggcgatgccacctacggcaagctgaccctgaagttcatc
tgcaccaccggcaagctgcccgtgccctggccca cctcgtgaccaccctgacc<u>c</u>acggcgtgcagtgcttcagccgctacc ccgaccacatgaagcagcacgacttcttcaagtccgccatgcccgaag
gctacgtccaggagcgcaccatcttcttcaaggacgacggcaactaca
agacccgcgccgaggtgaagttcgagggcgacaccctggtgaaccgca
tcgagctgaagggcatcgacttcaaggaggacggcaacatcctgggc
acaagctggagtacaactacaacagccacaacgtctatatcatggccg
acaagcagaagaacggcatcaaggtgaacttcaagatccgccacaaca
tcgaggacggcagcgtgcagctcgccgaccactaccagcagaacaccc
ccatcggcgacggccccgtgctgctgcccgacaaccactacctgagca
cccagtccgccctgagcaaagaccccaacgagaagcgcgatcacatgg
tcctgctggagttcgtgaccgccgccgggatcactctcggcatggacg
agctgtacaagtaa (D) Conversion of BFP sequence by one mutation
(SEQ ID No: 124)
atggtgagcaagggcgaggagctgttcaccggggtggtgcccatcctg
gtcgagctggacggcgacgtaaacggccacaagttcagcgtgtccggc
gagggcgagggcgatgccacctacggcaagctgaccctgaagttcatc
tgcaccaccggcaagctgcccgtgccctggccca cctcgtgaccaccctgacc<u>t</u>acggcgtgcagtgcttcagccgctacc gccgaccacatgaagcagcacgacttcttcaagtccgccatgcccgaa
gctacgtccaggagcgcaccatcttcttcaaggacgacggcaactaca
agacccgcgccgaggtgaagttcgagggcgacaccctggtgaaccgca
tcgagctgaagggcatcgacttcaaggaggacggcaacatcctgggc
acaagctggagtacaactacaacagccacaacgtctatatcatggccg
gacaagcaaagaacggcatcaaggtgaacttcaagatccgccacaaca
tcgaggacggcagcgtgcagctcgccgaccactaccagcagaacaccc
ccatcggcgacggccccgtgctgctgcccgacaaccactacctgagca
cccagtccgccctgagcaaagaccccaacgagaagcgcgatcacatgg
tcctgctggagttcgtgaccgccgccgggatcactctcggcatggacg
agctgtacaagtaa

TABLE 6

Effect of sequential delivery of Cas9 RNP and PAM or non-PAM ssDNA donor on HDR (FIG. 7B data).

| | | RD | RDx2 | R->D | D->R |
|---|---|---|---|---|---|
| PAM ssDNA donor | Avg (% GFP+ cells) | 4.9 | 6.2 | 10.9 | 12.3 |
| | Std | 0.2 | 0.0 | 0.5 | 1.7 |
| non-PAM ssDNA donor | Avg (% GFP+ cells) | 6.1 | 8.9 | 14.0 | 16.0 |
| | Std | 1.7 | 0.9 | 1.1 | 0.8 |

TABLE 7

Effect of dose on HDR (FIG. 7C data).

| | neg | (+)gRNA | (−)gRNA | 0.05 µg | 0.1 µg | 0.2 µg | 0.5 µg | 1 µg |
|---|---|---|---|---|---|---|---|---|
| Avg (% GFP+ cells) | 0.00 | 0.04 | 0.01 | 1.4 | 6.5 | 12.0 | 12.7 | 7.2 |
| Std | 0.00 | 0.02 | 0.00 | 0.2 | 1.5 | 1.1 | 0.4 | 0.4 |

TABLE 8

Effect of sequential delivery of Cas9 RNP and dsDNA donor on HDR (FIG. 7D data).

| | neg | (+)gRNA | (−)gRNA | RD | R->D |
|---|---|---|---|---|---|
| Avg (% GFP+ cells) | 0.05 | 0.18 | 0.09 | 4.25 | 10.36 |
| Std | 0.01 | 0.04 | 0.01 | 0.35 | 0.30 |

TABLE 9

Effect of sequential delivery on HDR using an alternative reporter gene (FIG. 7E data).

| | neg | (+)gRNA | (−)gRNA | RD | R -> D | D -> R |
|---|---|---|---|---|---|---|
| Avg (% GFP+ cells) | 0.14 | 0.13 | 0.02 | 22.75 | 32.85 | 31.55 |
| Std | 0.01 | 0.04 | 0.00 | 0.78 | 1.06 | 0.78 |

TABLE 10

Optimization of delivery of Cas9 RNP.

| neg | Pstd | P2 | P3 | P4 | P5 | P6 | P7 | P8 | P9 | P10 | P11 | P12 |
|---|---|---|---|---|---|---|---|---|---|---|---|---|
| 0 | 78 | 72 | 75 | 79 | 80 | 63 | 69 | 74 | 76 | 59 | 69 | 71 |

| P13 | P14 | P15 | P16 | P17 | P18 | P19 | P20 | P21 | P22 | P23 | P24 |
|---|---|---|---|---|---|---|---|---|---|---|---|
| 69 | 74 | 76 | 78 | 40 | 54 | 74 | 76 | 74 | 77 | 80 | 77 |

TABLE 11

Optimization of sequential delivery of Cas9 RNPs and ss oligonucleotide.

| neg | Cas9 RNP | Cas9/D | Pstd | Pstd | Pstd | P2 |
|---|---|---|---|---|---|---|
| 0.08 | 0.38 | 0.12 | 17.86 | 15.33 | 13.04 | 14.32 |

| P3 | P4 | P5 | P6 | P7 | P8 | P9 | P10 |
|---|---|---|---|---|---|---|---|
| 10.48 | 6.03 | 1.20 | 13.25 | 13.62 | 12.14 | 7.84 | 12.22 |

| P11 | P12 | P13 | P14 | P15 | P16 | P17 |
|---|---|---|---|---|---|---|
| 13.25 | 9.82 | 12.71 | 11.77 | 7.09 | 0.39 | 10.41 |

| P18 | P19 | P20 | P21 | P22 | P23 | P24 |
|---|---|---|---|---|---|---|
| 11.72 | 4.62 | 1.08 | 9.98 | 1.99 | 0.46 | 0.01 |

TABLE 12

Optimization of delivery of Cas9 RNP and dsDNA.

| neg | Cas9 RNP | Cas9/D | Pstd | P2 | P3 | P4 | P5 | P6 |
|---|---|---|---|---|---|---|---|---|
| 0.045 | 0.13 | 0.011 | 9.26 | 8.468 | 2.8 | 0.58 | 0.178 | 10.6 |

| P7 | P8 | P9 | P10 | P11 | P12 | P13 | P14 | P15 |
|---|---|---|---|---|---|---|---|---|
| 9.868 | 3.857 | 0.725 | 10.15 | 9.489 | 2.8 | 9.03 | 7.976 | 1.868 |

| P16 | P17 | P18 | P19 | P20 | P21 | P22 | P23 | P24 |
|---|---|---|---|---|---|---|---|---|
| 0.574 | 4.89 | 7.76 | 9.22 | 2.5 | 6.1 | 3.54 | 0.86 | 0 |

Results

Effect of Sequential Delivery of Nuclease and Donor DNA

The sequential delivery of Cas9 RNP followed by donor DNA resulted in more than a two-fold increase in EmGFP-positive cells regardless of the use of ssDNA or dsDNA donor (FIG. 7, panels B, D). The reverse sequential delivery of ssDNA donor first and then Cas9 RNP exhibited a similar effect (FIG. 7B). However, two consecutive electroporations without the intermediate wash step only showed mild improvement over the co-delivery of Cas9 RNP and ssDNA donor. The use of non-PAM strand donor exhibited slightly higher HDR efficiency than the PAM strand donor (FIG. 7B). The effect of sequential delivery was also observed in another reporter cell line system in which eBFP was converted to GFP by a single nucleotide substitution (FIG. 7E). The dosage titrations of ssDNA donor indicated that the optimal amount of ssDNA oligonucleotide was 0.2 to 0.5 µg per 10 µl reaction, which represented approximately 10 pmol of ssDNA oligonucleotide in 10 µl reaction (FIG. 7C). Upon optimization, we observed approximately 15% EmGFP-positive cells using the non-PAM ssDNA oligonucleotide (FIG. 7C and Table 11). The HEK293 cell viability for co-delivery of Cas9 RNPs and donor DNA was approximately 85%, whereas the cell viability for sequential delivery of Cas9 RNPs and donor decreased to approximately 50%. The optimal electroporation condition was highly dependent on cell type and should be determined experimentally.

Effects of Oligonucleotide Length and Modification on HDR

It has been reported that relatively short single-stranded oligonucleotides containing 25-61 bases homologous to the target sequence were capable of correcting a single point mutation (Igoucheva, O., Alexeev, V., Yoon, K., *Targeted gene correction by small single-stranded oligonucleotides in mammalian cells, Gene Ther.* 8(5):391-399 (2001)). The use of phosphorothioate modification of nucleotides has also shown to prevent degradation of oligonucleotide therapeutic agents in serum and cells (Brown, D. A., Kang, S. H., Gryaznov, S. M., DeDionisio, L., Heidenreich, O., Sullivan, S., Xu, X., Nerenberg, M. I., *Effect of phosphorothioate modification of oligodeoxynucleotides on specific protein binding, J. Biol. Chem.* 269(43):26801-26805 (1994). Here we examined the effect of oligonucleotide length and modification on HDR efficiency in our system. The oligonucleotides were chemically synthesized and PAGE-purified with and without phosphorothioate modification at both the 5' and 3' ends and phosphate modification at the 5' end with a total length that varied from 40 to 100 bases. The desired mutation was positioned at the center of the oligonucleotide. As shown in FIGS. 8A and 8B, the optimal length of ssDNA oligonucleotide was approximately 80 bases, harboring 36-40 bases of homology arm on each side. Oligonucleotides shorter than 60 bases reduced the HDR efficiency significantly, whereas the 100-base oligonucleotides also showed a slightly decreased efficiency. The phosphorothioate modification improved the efficiency of a 6-base insertion, although it had only a mild effect on one-base substitution. Using an 80-base modified oligonucleotide, we observed approximately 45% GFP-positive cells while introducing a single nucleotide substitution. To confirm the HDR result obtained from flow cytometry, the PCR fragments were cloned and 96 clones were randomly picked for sequencing. As shown in FIGS. 8C and 8D, approximately 6% of the colonies contained the wild type sequence, indicating that the overall genome modification efficiency was nearly 94%. Among the 94% edited cells, approximately 54% of the cells harbored insertions and deletions. In a few cases, a duplication of an 18-base sequence was inserted by an unknown mechanism (FIG. 8D, Clone No. 2). Approximately 40% of the clones contained the correct point mutation, which was in agreement with the GFP reporter assay.

TABLE 13

Effect of oligonucleotide length and modification on HDR (FIG. 8A data).

| | | neg | (+)gRNA | (−)gRNA | 40 | PS40 | 60 | PS60 | 79 | PS79 | 97 | PS97 |
|---|---|---|---|---|---|---|---|---|---|---|---|---|
| Equal Mass | Avg (% GFP+ cells) | 0.04 | 0.26 | 0.09 | 2.96 | 4.35 | 6.62 | 9.59 | 7.99 | 12.94 | 7.53 | 10.98 |
| | Std | 0.01 | 0.23 | 0.07 | 0.44 | 0.71 | 1.92 | 0.88 | 0.45 | 1.08 | 1.10 | 0.16 |
| Equal Molarity | Avg (% GFP+ cells) | 0.04 | 0.26 | 0.09 | 1.38 | 1.79 | 6.63 | 9.28 | 7.62 | 12.53 | 7.31 | 11.01 |
| | Std | 0.01 | 0.23 | 0.07 | 0.08 | 0.57 | 0.04 | 0.40 | 0.31 | 0.40 | 0.30 | 1.41 |

TABLE 14

Effect of oligonucleotide length and modification on HDR using an alternative reporter gene (FIG. 8B data).

| | 50 | PS50 | 60 | PS60 | 70 | PS70 | 80 | PS80 | 90 | PS90 | 100 | PS100 |
|---|---|---|---|---|---|---|---|---|---|---|---|---|
| Avg (% GFP+ cells) | 14.4 | 26.4 | 28.4 | 34.4 | 34.7 | 39.2 | 38.4 | 44.3 | 32.8 | 38.8 | 28.8 | 38.4 |
| Std | 1.4 | 1.1 | 0.3 | 3.4 | 2.9 | 3.4 | 2.3 | 0.9 | 3.4 | 5.1 | 2.3 | 2.3 |

TABLE 15

Sequencing verification (FIG. 8C data.)

| | wt | NHEJ | HDR |
|---|---|---|---|
| Relative percentage | 5.8 | 53.8 | 40.4 |

Figure 9A:
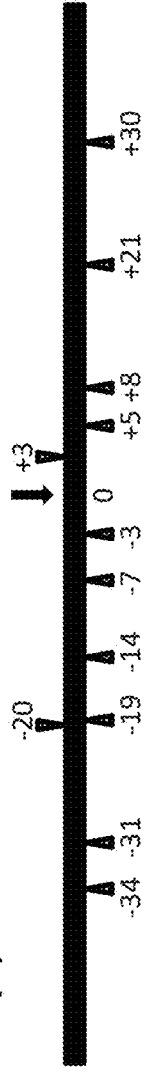
FIG. 9(A) discloses SEQ ID NO: 25. (B) gRNA cleavage efficiency. A series of gRNAs were associated with Cas9 nuclease separately and the resulting Cas9 RNPs were transfected into disrupted EmGFP stable cell lines. The percentages of Indel were evaluated at 48 hours post transfection. (C) dsDNA or ssDNA donors. A series of Cas9 RNPs along with a 400 bp dsDNA donor or a 97-base PAM ssDNA donor were sequentially delivered to disrupted EmGFP stable cell lines. Samples in the absence of donor (+gRNA) or gRNA (−gRNA) served as controls. The percentages of GFP-positive cells were determined by flow cytometry at 48 hours post transfection.
Figure 9C:
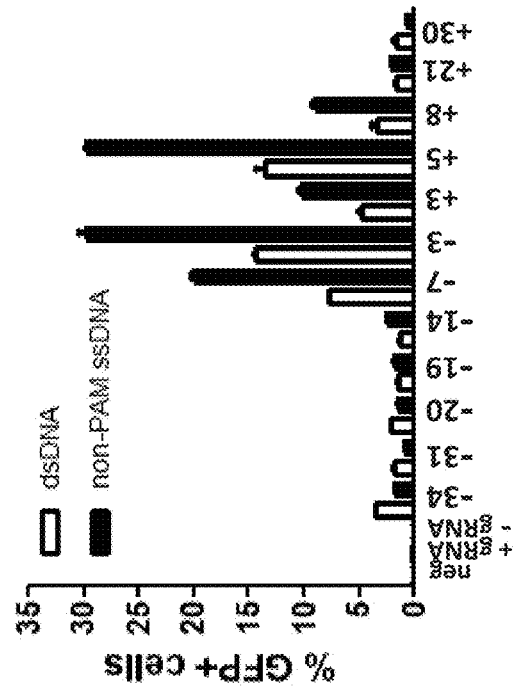
FIG. 9. DSB in close proximity to insertion site enhanced HDR. (A) Available gRNAs flanking the insertion site. A series of gRNAs were designed and synthesized flanking the insertion site (↓) targeting either the top strand (▼) or bottom strand (▲). The number and ±signs indicate the position of DSB upstream (−) or downstream (+) of the insertion site (0).
Figure 9B:
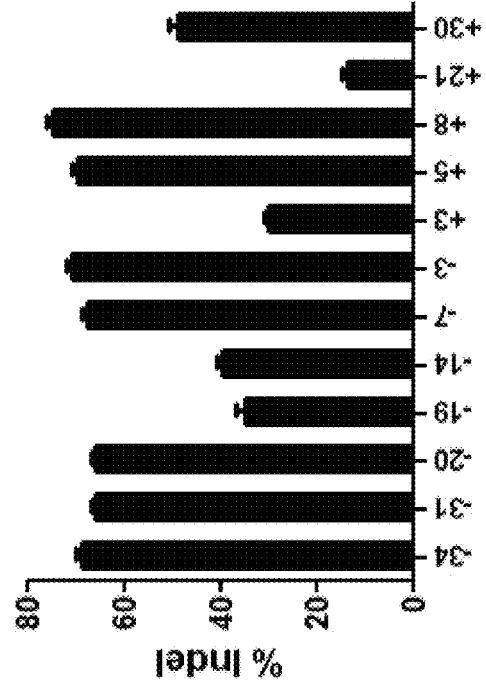

Double Strand Breaks in the Immediate Vicinity of the Altered Locus Facilitates HDR In the design of gRNAs for homologous recombination, it was previously recommended to introduce the cleavage site in close proximity to the altered locus (Inui, M., Miyado, M., Igarashi, M., Tamano, M., Kubo, A., Yamashita, S., Asahara, H., Fukami, M., Takada, S., *Rapid generation of mouse models with defined point mutations by the CRISPR/Cas9 system. Sci. Rep.* 4:5396 (2014)). However, the ability to accomplish this would depend on the availability of a PAM site near the altered locus. To test this, we designed a set of 12 gRNAs flanking the 6-base insertion site in EmGFP (FIG. 9A). The gRNAs were enzymatically synthesized by the G<small>ENE</small>A<small>RT</small>™ Precision gRNA Synthesis Kit and then complexed with P<small>LATINUM</small>™ Cas9 nuclease protein. The resulting Cas9 RNPs were delivered to cells by electroporation and the genome cleavage efficiencies were determined at 48 hours post transfection. As shown in FIG. 9B, some gRNAs were more active than others and no distinct pattern was observed. To evaluate the effect of distance between the DSB and the altered locus on HDR, we delivered Cas9 RNP and ssDNA or dsDNA donor into cells sequentially and then determined the percentage of EmGFP-positive cells using flow cytometry. As depicted in FIG. 9C, the gRNAs (−3, +3, and +5) in close proximity to the insertion site produced the highest percentages of EmGFP-positive cells. Although the +3 gRNA was closer to the insertion site than the +5 gRNA, the +3 gRNA exhibited lower HDR efficiency than the +5 gRNA likely because the genome cleavage efficiency of the +3 gRNA was two-fold lower than that of the +5 gRNA (FIGS. 9B and 9C). Under optimal conditions, we observed more than 30% EmGFP-positive cells using the −3 or +5 gRNAs, which represented more than 200-fold increase in knock-in efficiency over the donor-only negative control.

TABLE 16

Various genome cleavage efficiency with different gRNAs (FIG. 9B data).

| | −34 | −31 | −20 | −19 | −14 | −7 | −3 | (+)3 | (+)5 | (+)8 | (+)21 | (+)30 |
|---|---|---|---|---|---|---|---|---|---|---|---|---|
| Avg (% Indel) | 69.00 | 66.00 | 66.00 | 35.00 | 39.50 | 67.50 | 71.00 | 30.00 | 69.50 | 75.00 | 13.50 | 49.00 |
| Std | 1.41 | 1.41 | 1.41 | 2.83 | 2.12 | 2.12 | 1.41 | 1.41 | 2.12 | 1.41 | 2.12 | 2.83 |

TABLE 17

Double Strand Breaks in the immediate vicinity of the altered locus facilitates HDR (FIG. 9C data).

| | | Neg | (+)gRNA | (−)gRNA | −34 | −31 | −20 | −19 | −14 |
|---|---|---|---|---|---|---|---|---|---|
| dsDNA | Avg (% GFP+ cells) | 0.08 | 0.23 | 0.10 | 3.46 | 1.86 | 2.15 | 1.42 | 1.33 |
| | Std | 0.01 | 0.04 | 0.01 | 0.04 | 0.02 | 0.07 | 0.28 | 0.14 |
| ssDNA | Avg (% GFP+ cells) | 0.08 | 0.23 | 0.10 | 1.78 | 0.88 | 1.45 | 1.86 | 2.45 |
| | Std | 0.01 | 0.04 | 0.01 | 0.06 | 0.06 | 0.21 | 0.13 | 0.16 |

| | | −7 | −3 | (+)3 | (+)5 | (+)8 | (+)21 | (+)30 |
|---|---|---|---|---|---|---|---|---|
| dsDNA | Avg (% GFP+ cells) | 7.75 | 14.35 | 4.78 | 13.55 | 3.36 | 1.58 | 1.59 |
| | Std | 0.07 | 0.21 | 0.49 | 1.06 | 0.62 | 0.25 | 0.49 |
| ssDNA | Avg (% GFP+ cells) | 19.90 | 29.80 | 10.25 | 29.75 | 8.94 | 2.06 | 0.66 |
| | Std | 0.57 | 0.99 | 0.49 | 0.35 | 0.45 | 0.18 | 0.18 |

Asymmetric PAM and Non-PAM ssDNA Donors Facilitate HDR

Figure 14A:
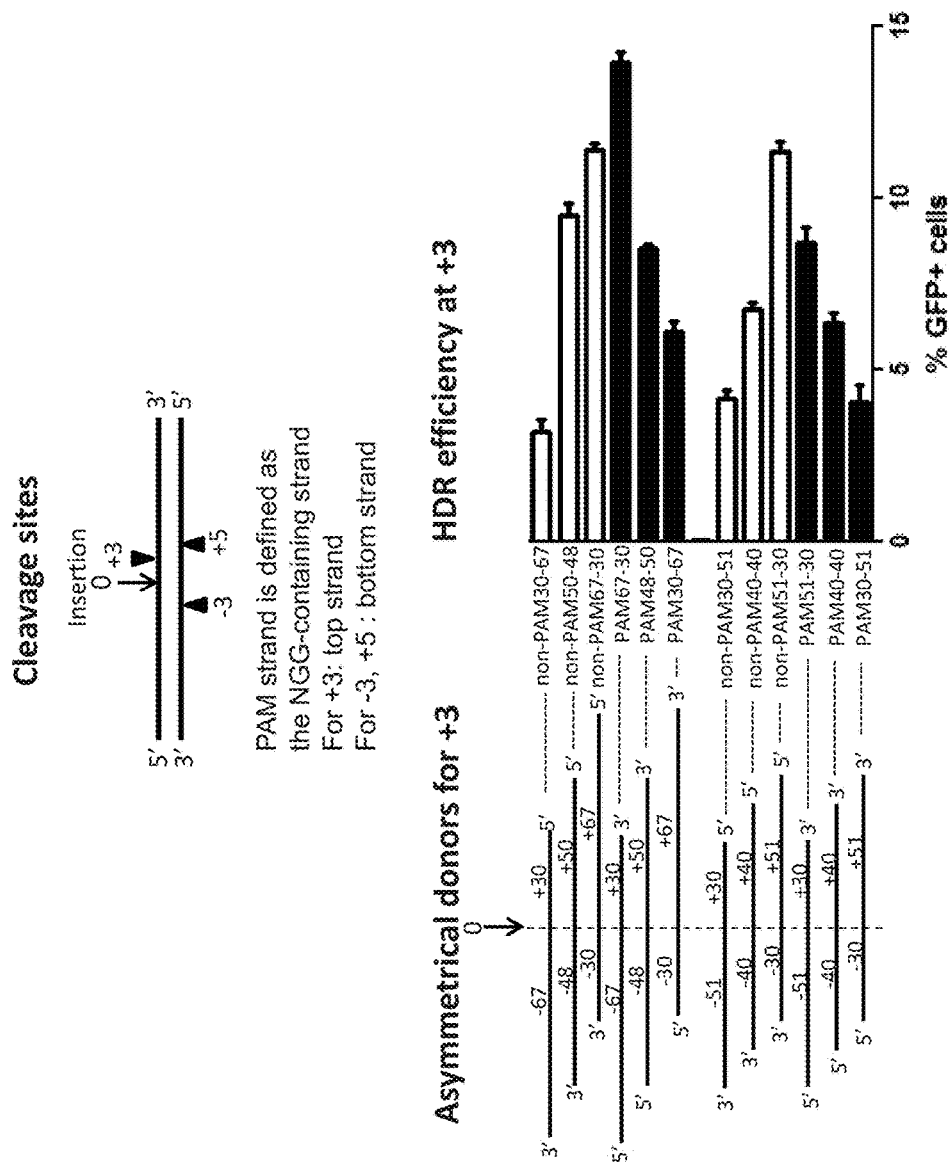
FIG. 14A. Both asymmetric PAM and non-PAM ssDNA donors facilitate HDR. Three separate gRNAs flanking the insertion site (↓ with a 0 above) were designed (top of figure) and synthesized with double-stranded breaks (DSB) occurred at position −3, +3 and +5 separately. PAM strand is defined as the NGG-containing strand. The +3 gRNA's PAM is on the top 5' to 3' strand (▼), whereas the −3 and +5 gRNAs have PAMs on the bottom 3' to 5' strand (▲). A series of ssDNA donors (lower left of figure) were designed with various number of nucleotides on the left arm (−) and right arm (+) of the insertion site. Both the PAM and non-PAM strands were used. The Cas9 RNP (1.5 μg Cas9 nuclease, 360 ng of the +3 gRNA) and ssDNA donors (10 pmol) were sequentially delivered to disrupted EmGFP stable HEK293 cell lines (lower right of figure). At 48 hours post transfection, the % Indel was determined by the Genomic Cleavage and Detection assay, whereas the percentages of EmGFP-positive cells were determined by flow cytometry.
Figure 14B:
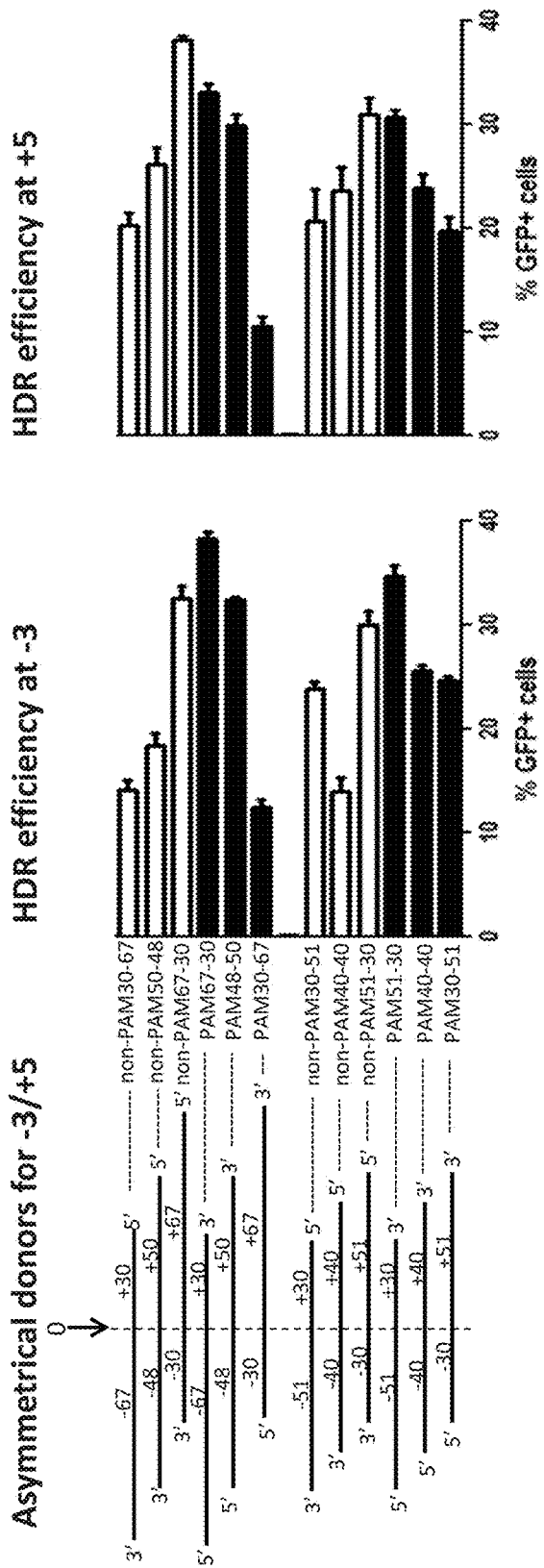
FIG. 14B. This figure us similar to FIG. 14A except that the −3 gRNA (center) or +5 gRNA (right) was used.

A recent report showed that an asymmetric ssDNA donor, complementary to the target strand with 36-bases on the PAM-distal side and a 91-base extension on the PAM-proximal side of the break, enhanced HDR efficiency (Richardson et al., Nat. Biotechnol. 34:339-344 (2016)). It was proposed that when Cas9 cleaved the target loci, the 3' end of the PAM-distal strand could dissociate from the RNP/DNA complex and initiate HDR by annealing to a donor complementary to this exposed sequence, suggesting that a donor designed in this manner would be preferred. However, we observed only a slight difference in HDR efficiency between the symmetric PAM (corresponding to the non-target strand in Richardson et al., Nat. Biotechnol. 34:339-344 (2016)) and non-PAM (corresponding to the target strand in Richardson et al., Nat. Biotechnol. 34:339-344 (2016)) strands (FIG. 7B). To further understand the mechanism of ssDNA donor-mediated HDR, we designed gRNAs to introduce DSBs both upstream (−3 gRNA) and downstream (+5 gRNA) of the insertion site (FIG. 10A). Furthermore, we designed a set of asymmetric PAM strand and non-PAM strand ssDNA donors with 30-bases on one homology arm and 51-bases or 67-bases on the other homology arm (FIG. 10B and FIG. 14). The PAM strand was defined as the strand containing the NGG PAM sequence. The symmetric ssDNA donors served as controls. The percentages of GFP+ cells determined by flow cytometry were plotted separately for each individual gRNA (FIG. 14 and see Table 18). For clarification, only a subset of asymmetric ssDNA donors were shown in FIGS. 10B and 10C with the percentage of GFP+ cells normalized to the percentage cleavage efficiencies (FIG. 9B).

When the either the −3 or +5 gRNAs were used to generate DSB with its PAM site located upstream or downstream (respectively) of the insertion site (FIG. 10A), the asymmetric PAM strand ssDNA donors 67-30 and non-PAM strand donor 67-30 (FIG. 10A, panels A and B respectively) yielded the highest HDR efficiency (shown in FIG. 10C). This suggests that a 30 base 3' homology arm is favored over longer arms of 67 bases on the 3'end. This fits the model described in FIG. 10A where the resected DSB allows access to a 3' overhang for annealing. Supporting this notion is the data obtained with both with the PAM strand 30-67 and the non-PAM 30-67 donors where editing efficiency was significantly less (FIG. 10C). The data from the −3 gRNA agrees with the +5 results showing that placement of the insertion/SNP relative to the DSB has a small but measurable effect on efficiency. Here it is suggested that when the edited area is either upstream or downstream of the cut, HDR with a donor that anneals to the template side containing the edit site is slightly inhibited potentially due to needing to overcome the mismatch between the original sequence and the donor sequence (See Table 21). Finally, the symmetrical donors shown in FIG. 10 (and in FIG. 14A-14B) show an intermediate efficiency suggesting the optimal 3' homology arm length in this model system could be near 30 bases but likely not as much as 50 bases.

TABLE 19

Both asymmetric PAM (P) and non-PAM (NP) ssDNA donors facilitate HDR (FIG. 10 data).

| | | 30-67 | | 48-50 | | 67-30 | |
|---|---|---|---|---|---|---|---|
| | | P | NP | P | NP | P | NP |
| (−3)gRNA | Avg (% GFP+ cells) | 54.3 | 20.0 | 46.3 | 26.1 | 17.7 | 46.5 |
| (−3)gRNA | Std | 2.0 | 2.0 | 2.3 | 1.5 | 2.8 | 2.1 |
| (+5)gRNA | Avg (% GFP+ cells) | 48.5 | 29.6 | 43.9 | 38.2 | 15.4 | 55.9 |
| (+5)gRNA | Std | 2.0 | 5.1 | 3.4 | 3.1 | 2.2 | 2.1 |

The results were further validated using the same reporter system as described in Richardson et al., Nat. Biotechnol.

TABLE 18

Both asymmetric PAM and non-PAM ssDNA donors facilitate HDR (Abbreviations: NP = non-PAM, P = PAM) (FIG. 14 data).

| | | 30-51 | | 40-40 | | 50-30 | | 30-67 | | 48-50 | | 67-30 | |
|---|---|---|---|---|---|---|---|---|---|---|---|---|---|
| | | P | NP | P | NP | P | NP | P | NP | P | NP | P | NP |
| (+3) gRNA | Avg (% GFP+ cells) | 4.0 | 11.3 | 6.4 | 6.7 | 8.7 | 4.1 | 6.1 | 11.4 | 8.5 | 9.5 | 13.9 | 3.2 |
| (+3) gRNA | Std | 1.0 | 0.5 | 0.5 | 0.4 | 0.9 | 0.4 | 0.6 | 0.4 | 0.2 | 0.7 | 0.6 | 0.7 |
| (−3) gRNA | Avg (% GFP+ cells) | 34.7 | 23.7 | 25.6 | 14.0 | 24.6 | 30.0 | 38.2 | 14.1 | 32.3 | 18.3 | 12.4 | 32.5 |
| (−3) gRNA | Std | 2.6 | 1.8 | 1.0 | 3.2 | 1.0 | 3.1 | 1.7 | 2.2 | 0.7 | 3.0 | 1.9 | 2.9 |
| (+5) gRNA | Avg (% GFP+ cells) | 30.6 | 20.6 | 23.9 | 23.6 | 19.7 | 30.8 | 32.9 | 20.2 | 29.9 | 26.0 | 10.5 | 38.0 |
| (+5) gRNA | Std | 1.6 | 7.6 | 3.2 | 5.5 | 3.1 | 3.9 | 2.2 | 3.1 | 2.4 | 3.9 | 2.3 | 1.2 |

34:339-344 (2016), in which a gRNA targeted the eBFP gene. The asymmetric donors with a short 35 base on the 3' end that could anneal to the resected 3' end of the genomic DSB performed better with the PAM 65-35 and non-PAM 65-35 resulting in approximately 52% and 48% HDR efficiency respectively (see Table 20), whereas the asymmetric donors with a long 65 base on the 3' end were less effective with PAM 35-65 and non-PAM 35-65 resulting in 32% and 21% GFP+ cells respectively. In addition, similar results were seen when using a cas9 mRNA and asymmetric gRNAs.

TABLE 20

Both asymmetric PAM (P) and non-PAM (NP) ssDNA donor facilitate HDR.

|  | 40-40 | | 35-65 | 50-50 | 65-35 | | 50-50 | 35-65 |
|---|---|---|---|---|---|---|---|---|
|  | P | NP | P | P | P | NP | NP | NP |
| Avg (% GFP+ cells) | 44.6 | 42.2 | 32.6 | 41.5 | 51.7 | 47.4 | 28.5 | 21.2 |
| Std | 0.5 | 0.5 | 1.1 | 0.7 | 1.0 | 1.2 | 2.4 | 1.6 |

TABLE 21

Insertion of Flag tag.

|  |  | 32-5' | | | 32-3' | | | ssDNA | | |
|---|---|---|---|---|---|---|---|---|---|---|
|  |  | wt | NHEJ | HDR | wt | NHEJ | HDR | wt | NHEJ | HDR |
| Relative % | Avg | 22.0 | 78.0 | 0.0 | 11.1 | 54.6 | 34.2 | 18.2 | 63 | 18.8 |
|  | Std | 2.0 | 2.0 | 0.0 | 2.9 | 2.0 | 3.0 | 4.0 | 4 | 4.5 |

Overall, the use of either the asymmetric PAM strand or non-PAM strand ssDNA donor, which harbors approximately 65-67 bases of homology on the 5' end and 30-35 bases of homology on the 3' end, resulted in the highest efficiency of HDR regardless of which genomic strand contained the PAM or whether the DSB was upstream or downstream of the edit site, inferring a common intermediate for HDR. Contrary to the proposed model of Richardson et al., Nat. Biotechnol. 34:339-344 (2016), we saw no bias in donor design favoring the genomic strand that is proposed to be released by the Cas9 complex.

Figure 11D:
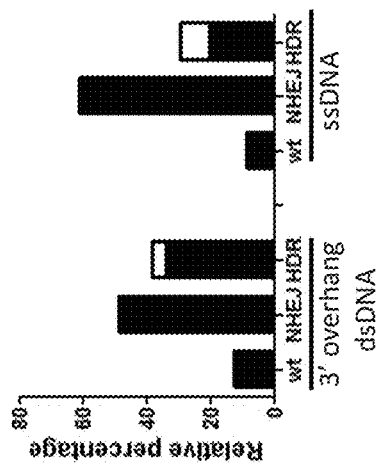
FIG. 11. Insertion of a FLAG tag along with an EcoRI site using dsDNA donor with single-stranded overhangs. (A) Various donor DNA molecules containing a 30-base FLAG tag along with an EcoRI site were designed and synthesized, including single-stranded DNA donor (ssDNA), blunt-end dsDNA donor (blunt), dsDNA donor with 5' overhang (5'), dsDNA donor with 3' overhang (3'). The length of overhangs varied from 6 nucleotides (6), 15 nucleotides (15) to 30 nucleotides (30). The 3' and 5' ends of the oligonucleotides harbored two consecutive phosphorothioate-modified bases (Table 4). The short dsDNA donors with and without overhangs were prepared by annealing two short DNA oligonucleotides. The Cas9 RNP targeting the eBFP gene and various forms of DNA donors were sequentially delivered to HEK293 cells expressing eBFP. At 48 hours post transfection, the eBFP locus was PCR-amplified. The resulting PCR fragments were analyzed by the genomic cleavage and detection assays to determine the percentage of Indel or subjected to restriction digestion with EcoRI to determine the percentage of digestion. (B) Length of 3' overhang. The dsDNA donors with 15, 24, 30, 36, or 45-base 3' overhang were sequentially delivered with Cas9 RNP to HEK293 cells expressing eBFP. Alternatively, a dsDNA donor with 30-base 3' overhang but without phosphorothioate modification (30-3'n) was used. The percentage of digestion with EcoRI was determined at 48 hours post transfection. (C) Dose effect. Cas9 RNP and various amount of ssDNA donor or dsDNA donor with 30-base 3' overhangs were sequentially delivered to HEK293 cells expressing eBFP. The eBFP loci were PCR-amplified. The resulting PCR fragments were analyzed by EcoRI digest. (D) Sequencing verification. The PCR fragments were cloned into E. coli and 192 clones were randomly picked for sequencing. The relative percentage of wild type (wt), NHEJ, and HDR clones derived from either ssDNA donor (ssDNA) or dsDNA with 3' overhangs (3' overhang) was plotted. The white rectangles represented the population of clones that contained the insert but with a point mutation. Examples of edited clones were shown in (E) (not representing the actual percentages of NHEJ and HDR). The underlined sequences represented the FLAG tag along with an RI site.
Figure 11E:
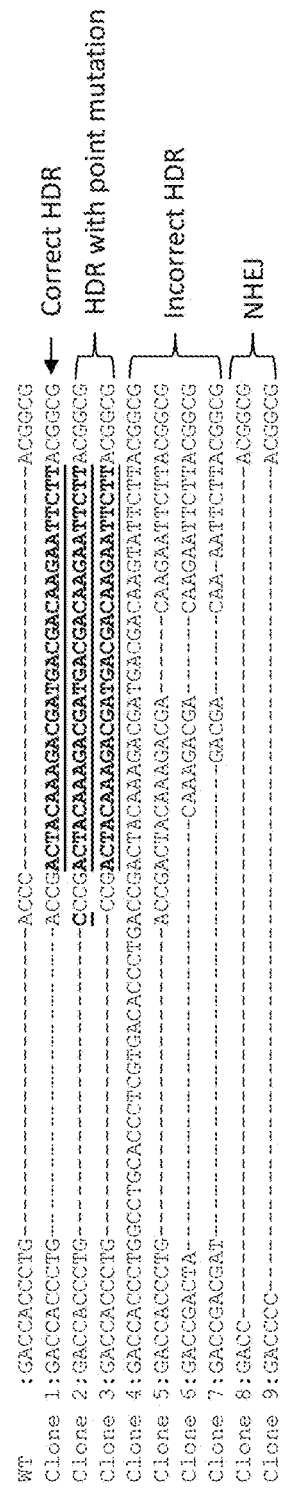

Short Double-Stranded DNA Donor with Single-Stranded Overhangs Facilitates Highly Efficient HDR The work of asymmetric ssDNA donors described above suggested that only about 30 bases at the 3' end were needed for sufficient single stranded DNA annealing. To extend this concept, we hypothesized that a dsDNA donor harboring single-stranded overhangs would facilitate HDR to higher levels than with blunt ends. To test this hypothesis, we designed and generated a series of donor molecules with either blunt end, 5' end protrusion or 3' end protrusion by annealing two small single-stranded oligonucleotides. A single-stranded DNA donor was used as a control. The 5' and 3' ends of oligonucleotides were protected with two consecutive phosphorothioate-modified bases (Table 3). For proof of concept, we inserted a 30 nucleotide FLAG epitope tag along with an EcoRI site into the BFP gene stably expressed in HEK293 cells. The gRNA was designed to target the top DNA strand. The length of single-stranded overhangs varied from 6 nucleotides to 30 nucleotides. The oligonucleotides were denatured and re-annealed prior to transfection forming the structures described in FIG. 11A. The Cas9 RNP and donor DNA were delivered sequentially to HEK293 cells by electroporation. Co-delivery of Cas9 RNPs and donor DNA gave lower HDR efficiencies. At 48 hours post transfection, the genomic locus was PCR-amplified and the editing efficiencies were determined using a GCD assay. As shown in FIG. 11A, approximately 75% cleavage efficiencies were observed with various donor configurations. When the PCR fragments were subjected to restriction digestion with EcoRI to identify properly inserted constructs, only the donor DNA molecules containing 30-base single-stranded overhangs at the 3' ends produced the expected digested fragments (30-3' in FIG. 11, panel A). The double stranded donor with 30-base 3' overhangs was inserted with efficiencies above 35% while the ssDNA donor was inserted with approximately 20% efficiency. Upon close examination of the length of the single-stranded overhang, we found that the donor DNA molecules with 24-base 3'-protruded ends produced approximately 15% digestion efficiency while seemingly optimal length of single-stranded overhangs was 30 to 36 nucleotides with a digestion efficiency of approximately 40%. The use of a 45-base single-stranded donor decreased the efficiency slightly (FIG. 11B). Comparing two donor DNA molecules containing 30-base single-stranded overhangs at the 3' ends with and without phosphorothioate modification, the donor DNA with phosphorothioate modification at both 5' and 3' ends exhibited approximately 42% digestion efficiency (30-3') whereas the donor DNA without phosphorothioate modification (30-3'n) lowered the efficiency to around 27% (FIG. 11B). Furthermore, we titrated the amount of ssDNA donor and dsDNA donor with 30-base 3' end protrusion. As depicted in FIG. 11C, the optimal concentration of DNA donors in the transfection reaction was approximately 1 µM. Under these conditions, we measured greater than 40% digestion efficiency with the 3'-protruded dsDNA donor, which was nearly 10% higher than that using ssDNA. When we performed sequencing analysis of 192 clones, 13% of the clones were wild type and 48.8% of the clones contained indels suggesting that in these clones the cleavage was repaired by NHEJ. Although 39% of the clones contained the insert, among them about 4% of the clones harbored a point mutation, most likely due to an error in the synthetic DNA oligonucleotide (FIG. 11D, white rectangle). Excluding all the errors and wild type clones, 34% of the clones harbored the correct insertion.

We also analyzed the edited locus where the ssDNA oligonucleotide served as donor. In this case, approximately 9% of the clones were wild type, 61% of the clones were NHEJ, and 30% of the clones were HDR (FIG. 11D). Among the 30% HDR, 9% of the clones harbored the insertion but with a single base mutation. After excluding the errors, 21% of the clones harbored the correct insertion.

TABLE 22

Short double-stranded DNA donor with single-stranded overhangs facilitates HDR (FIG. 11A data).

|  | Neg | (+) gRNA | (−) gRNA | blunt | 6-5' | 6-3' | 15-5' | 15-3' | 30-5' | 30-3' | ssDNA |
|---|---|---|---|---|---|---|---|---|---|---|---|
| Avg (% Indels) | 0.00 | 77.00 | 0.00 | 68.50 | 56.50 | 78.50 | 69.50 | 81.00 | 80.00 | 81.00 | 77.50 |
| Std | 0.00 | 2.83 | 0.00 | 2.12 | 4.95 | 0.71 | 0.71 | 1.41 | 0.00 | 4.24 | 3.54 |
| Avg (% digestion) | 0.00 | 0.00 | 0.00 | 0.00 | 0.00 | 0.00 | 0.00 | 0.50 | 1.00 | 37.50 | 23.50 |
| Std | 0.00 | 0.00 | 0.00 | 0.00 | 0.00 | 0.00 | 0.00 | 0.00 | 0.00 | 4.95 | 3.54 |

TABLE 23

Effect of length of 3' overhang on percentage of digestion (FIG. 11B).

|  | 15-3' | 24-3' | 30-3'n | 30-3' | 36-3' | 45-3' |
|---|---|---|---|---|---|---|
| Avg (% digestion) | 0.8 | 17.3 | 31.5 | 43.1 | 41.7 | 37.0 |
| Std | 0.4 | 1.1 | 0.7 | 1.6 | 2.3 | 4.2 |

TABLE 24

Dose effect of ssDNA donor and 3' overhanged short dsDNA donor (FIG. 11C).

| [DNA] (μM) | 30-3' Avg (% digestion) | 30-3' Std | ssDNA Avg (% digestion) | ssDNA Std |
|---|---|---|---|---|
| 3.00 | 28.50 | 2.12 | 7.60 | 1.98 |
| 2.00 | 39.00 | 2.83 |  |  |
| 1.65 |  |  | 22.00 | 4.24 |
| 1.00 | 41.50 | 2.12 | 27.00 | 4.24 |
| 0.66 |  |  | 24.50 | 2.12 |
| 0.50 | 37.00 | 0.00 | 20.00 | 1.41 |

TABLE 25

Sequencing analysis (FIG. 11D).

|  |  | Relative percentage | HDR with point mutation | Total |
|---|---|---|---|---|
| 3' overhanged donor | wt | 12.7 | 0 | 12.7 |
|  | NHEJ | 48.8 | 0 | 48.8 |
|  | HDR | 34.1 | 4.4 | 38.5 |
| ssDNA donor | wt | 9 | 0 | 9 |
|  | NHEJ | 61.2 | 0 | 61.2 |
|  | HDR | 20.5 | 9.3 | 29.8 |

In order to understand the polarity of dsDNA donor with single stranded overhangs, we inserted a FLAG epitope tag along with an EcoRI site into a separate locus where the +5 gRNA was targeting the bottom strand of EmGFP gene (see Table 21). The Cas9 RNPs were first delivered into GRIP-TITE™ HEK293 cells, followed by the delivery of ssDNA donor, or short dsDNA donors with 32-base single stranded overhangs at either 5' or 3' end. Samples in the absence of gRNA served as controls. At 48 hours post transfection, the genomic loci were amplified by PCR. The resulting PCR fragments were subjected to restriction digestion with EcoRI (data not shown) or subjected to sequencing analysis. The integration efficiency of FLAG epitope tag along with an EcoRI was approximately 34% using dsDNA donor with 3' overhangs and 20% using ssDNA donor. The dsDNA donor with 5' overhangs resulted in a barely detectable integration product. The results indicated that the polarity of single stranded overhangs remained the same regardless of how the DSBs were introduced by Cas9 RNPs.

Discussion

We have demonstrated that mammalian cells are fully capable of carrying out homology directed end repair efficiently without exogenous inhibition of the non-homologous end-joining pathway. The design and delivery of gRNAs, Cas9 nuclease, and donor molecules are critical to achieve high HDR efficiencies. Ideally, in order to achieve high editing efficiency, the double-stranded break induced by Cas9 nuclease should be in close proximity to the edit site, as just a few additional bases further up- or downstream can make a significant difference in editing efficiency. One limitation of the CRISPR system for precise editing is exposed here since the location of a potential DSB site, and consequently the efficiency of donor insertion to the genome, is dictated by the availability of PAM sites relatively near the intended edit. Further, even though a gRNA target site happens to be in the immediate vicinity of the edit locus, it is not guaranteed to have high modification efficiency because the gRNA activity may depend on the nature of the gRNA sequence, chemical modification, as well as its accessibility to the genomic locus. Finally, the chance of off-target cutting for each gRNA must be considered. In this regard, alternate tools such as TALENs mutated to lack the 5'T targeting requirement, or recently potentially *N. gregoryi* Argonaute (REF) have an inherent advantage over CRISPR in they can be programed to target virtually anywhere in the genome with no PAM restrictions.

If the Cas9 RNPs are efficiently delivered to cells for induction of double stranded breaks and the donor molecules are readily available at the time of DNA repair, the HDR pathway can be nearly as efficient as the NHEJ pathway. The HDR frequencies depend on the dose of donor DNA molecules with the optimal delivery concentration being approximately 1 μM. The optimal length of ssDNA donor is approximately 70 to 100 nucleotides, having a 35-50 base homology arm on either side of the edit sequence. The protection of donor DNA with phosphorothioate modification improves HDR efficiency in our model system. The delivery conditions for Cas9 RNPs and donors are also crucial as we observe that sequential delivery of Cas9 RNPs and donor DNA facilitates HDR. This is may be due to the Cas9 protein having non-specific DNA binding activity, leading to decreased transfection efficiency when paired with donor. However, sequential delivery is not applicable to cells that are sensitive to multiple rounds of electroporation, such as iPSC. In iPSC, the co-delivery of Cas9 RNPs and ssDNA donor produced up to 24% HDR efficiency (data not shown). The use of Cas9-expressing cells can be beneficial for genome editing because the delivery of Cas9 nuclease is not necessary, resulting in increased transfection efficiency of gRNA and/or donor DNA. For example, we observed precise genome editing rates of up to 40% in Cas9-expressing iPSCs for a single nucleotide substitution at multiple genomic loci (data not shown). However, extra effort is required to generate the stable cell lines expressing Cas9 nuclease with the added risk for a higher off-target effect.

The donor design and configuration also contribute to the editing efficiency. A recent report showed that asymmetric design of ssDNA donors promoted HDR by overlapping the Cas9 cut site with 36-bases on the PAM-distal side and with a 91-base extension on the PAM-proximal side of the break. A donor DNA complementary to the non-target strand stimulated HDR frequencies up to 2.6-fold greater than those obtained with a donor DNA complementary to the target strand (Richardson et al., Nat. Biotechnol. 34:339-344 (2016)). However, we observe that both the asymmetric PAM strand (corresponding to the non-target strand in Richardson et al., 2016) and non-PAM strand (corresponding to the target strand in Richardson et al., 2016) enhance HDR regardless of the orientation of the cas9 nuclease. Thus, we propose that Cas9 nuclease cleaves and both sides of the double-stranded break are recognized by the DNA repair machinery equally. In this model, a repertoire of cellular proteins involved in DNA repair is recruited to the broken ends to rectify the damaged DNA via either NHEJ (FIG. 12A) or the HDR pathway (FIG. 12, panels B, C, and D). In order for HDR-mediated donor insertion to occur, cellular exonucleases excise the ends from 5' to 3' thereby generating 3' overhangs on either side of the break (Nimonkar, A. V., Ozsoy, A. Z., Genschel, J., Modrich, P., Kowalczykowski, S. C., *Human exonuclease 1 and BLM helicase interact to resect DNA and initiate DNA repair*, PNAS 105(44):16906-16911 (2008)), which can anneal to the 3' end of either a PAM or non-PAM ssDNA donor. In either case, one of the 3' recessive ends of the break will anneal with ssDNA donor and then be extended by DNA polymerase with the 5' end of the ssDNA donor serving as template (FIG. 12B). However, it is unclear how the other 3' recessive end of the break bridges the newly-extended dsDNA and to repair the lesion (Kan, Y., Ruis, B., Hendrickson, E. A., *The Mechanism of Gene Targeting in Human Somatic Cells*, PLOS Genetics 10(4):e1004251 (2014)). It appears that 30-36 nucleotides are sufficient for single stranded DNA annealing at each end. The polarity and spacing of 3' recessive ends are further confirmed by the use of short dsDNA donors with single stranded overhangs. By annealing two single-stranded DNA oligonucleotides, we create different configurations of donor DNA molecules. Interestingly, short dsDNA molecules, ideally with 30 to 36-base single-stranded overhangs at the 3' ends, appear to be used efficiently in the HDR pathway regardless of whether the gRNA targets the top or bottom strand. These results support a model whereby after the DSB is made a common "3' recessed ends" intermediate is formed by the HDR machinery and can be used with many complementary donor DNA molecules containing matching 3' homology arms. This model and associated data favor the design of donor DNAs with the insertion or SNP repair element as close to the cleavage site as possible and 3' protruding single strand homology arms of approximately 30-36 bases for larger donor molecules. For smaller single stranded donor molecules, 30-35 base arms 3' to the insertion/repair cassette and greater than 40 bases on the 5' end seems to be favored.

While the foregoing embodiments have been described in some detail for purposes of clarity and understanding, it will be clear to one skilled in the art from a reading of this disclosure that various changes in form and detail can be made without departing from the true scope of the embodiments disclosed herein. For example, all the techniques, apparatuses, systems and methods described above can be used in various combinations.

What is claimed is:

1. A method for performing homologous recombination, the method comprising:
   (a) generating a double-stranded break in a nucleic acid molecule present inside a cell to produce a cleaved nucleic acid molecule, and
   (b) contacting the cleaved nucleic acid molecule generated in (a) with a partially double-stranded donor nucleic acid molecule,
   wherein the cleaved nucleic acid molecule and the donor nucleic acid molecule each contain matched termini on at least one end,
   wherein the matched termini on at least one end of the cleaved nucleic acid molecule and on at least one end the donor nucleic acid molecule is at least ten nucleotides in length,
   wherein the matched terminus on at least one end of the cleaved nucleic acid molecule is double-stranded and the matched terminus on at least one end of the donor nucleic acid molecule comprises a 3' single-stranded overhang.

2. The method of claim 1, wherein at least one pair of matched termini of the cleaved nucleic acid molecule and the donor nucleic acid molecule share between ten and seventy-five complementary nucleotides.

3. The method of claim 1, wherein the donor nucleic acid molecule contains one or more terminal nuclease resistant groups in at least one strand of at least one terminus.

4. The method of claim 3, wherein the donor nucleic acid molecule contains one or more terminal nuclease resistant groups in both strands of both termini.

5. The method of claim 3, wherein the donor nucleic acid molecule contains a single terminal phosphorothioate linkage in both strands of both termini.

6. The method of claim 3, wherein the donor nucleic acid molecule contains two terminal phosphorothioate linkage in both strands of both termini.

7. The method of claim 1, wherein the donor nucleic acid molecule has asymmetric termini.

8. The method of claim 1, wherein the single-stranded 3' overhang of the donor nucleic acid molecule is from 10 to 95 nucleotides in length.

9. The method of claim 8, wherein the 3' overhang of the donor nucleic acid molecule contains at least one terminal nuclease resistant group.

10. The method of claim 8, wherein the 3' overhang of the donor nucleic acid molecule contains two nuclease resistant groups.

11. The method of claim 9, wherein the nuclease resistant group is a phosphorothioate linkage.

12. The method of claim 1, wherein the donor nucleic acid molecule comprises two single-stranded 3' overhangs, each of which is from 10 to 95 nucleotides in length.

* * * * *

UNITED STATES PATENT AND TRADEMARK OFFICE
CERTIFICATE OF CORRECTION

PATENT NO. : 10,428,327 B2
APPLICATION NO. : 15/605586
DATED : October 1, 2019
INVENTOR(S) : Xiquan Liang, Robert Potter and Namritha Ravinder Page 1 of 1

It is certified that error appears in the above-identified patent and that said Letters Patent is hereby corrected as shown below:

In the Claims

In Claim 6, Column 102, Lines 23-25, change:
"6. The method of claim 3, wherein the donor nucleic acid molecule contains two terminal phosphorothioate linkage in both strands of both termini."

To:
-- 6. The method of claim 3, wherein the donor nucleic acid molecule contains two terminal phosphorothioate linkages in both strands of both termini. --

Signed and Sealed this
Thirtieth Day of June, 2020

Andrei Iancu
*Director of the United States Patent and Trademark Office*